United States Patent [19]

Brown et al.

[11] Patent Number: 5,962,436
[45] Date of Patent: Oct. 5, 1999

[54] FUNGICIDAL CYCLIC AMIDES

[75] Inventors: Richard James Brown, Newark, Del.; Deborah Ann Frasier, Martinez, Calif.; Constance Happersett, Christiana, Del.; Peter Paul Castro, Port Deposit, Md.; Charlene Gross Sternberg, Wilmington, Del.

[73] Assignee: E. I. du Pont de Nemours and Company, Wilmington, Del.

[21] Appl. No.: 08/894,539

[22] PCT Filed: Feb. 14, 1996

[86] PCT No.: PCT/US96/02333

§ 371 Date: Aug. 21, 1997

§ 102(e) Date: Aug. 21, 1997

[87] PCT Pub. No.: WO96/26191

PCT Pub. Date: Aug. 29, 1996

Related U.S. Application Data

[63] Continuation-in-part of application No. 08/393,743, Feb. 24, 1995.

[51] Int. Cl.[6] .......................... A01N 55/10; A01N 55/02; A01N 43/653; C07D 249/12
[52] U.S. Cl. .......................... 514/63; 514/384; 514/385; 514/184; 548/263.6; 548/263.8; 548/264.2; 548/264.6; 548/265.6; 548/266.4; 548/263.2; 548/264.8
[58] Field of Search .......................... 548/263.6, 263.8, 548/264.2, 264.6, 265.6, 266.4, 263.2, 264.8, 103; 514/63, 384, 385, 184

[56] References Cited

U.S. PATENT DOCUMENTS

| | | | |
|---|---|---|---|
| 4,098,896 | 7/1978 | Edwards | 424/269 |
| 5,034,388 | 7/1991 | Clough et al. | 514/247 |
| 5,194,662 | 3/1993 | Brand et al. | 560/35 |
| 5,292,759 | 3/1994 | Brand et al. | 514/339 |
| 5,747,516 | 5/1998 | Brown et al. | 514/359 |

FOREIGN PATENT DOCUMENTS

| | | | |
|---|---|---|---|
| 2 104 806 | 3/1994 | Canada | C07C 251/58 |
| 2 104 806 A1 | 3/1994 | Canada | C07C 251/58 |
| 0 363 818 A1 | 10/1989 | European Pat. Off. | C07D 213/70 |
| 0 398 692 A2 | 5/1990 | European Pat. Off. | C07C 251/40 |
| 0 460 575 A1 | 6/1991 | European Pat. Off. | C07C 251/60 |
| 0 463 488 A1 | 6/1991 | European Pat. Off. | C07C 251/60 |
| 0 508 126 A1 | 3/1992 | European Pat. Off. | C07D 231/32 |
| 44 13 669 A1 | 7/1993 | Germany | C07D 307/60 |
| WO 92/16510 | 10/1992 | WIPO | C07D 231/32 |
| WO 93/07116 | 4/1993 | WIPO | C07C 271/28 |
| WO 93/15046 | 8/1993 | WIPO | C07C 271/28 |
| WO 95/01971 | 1/1995 | WIPO | C07D 307/94 |
| WO 95/14009 | 5/1995 | WIPO | C07D 249/12 |

OTHER PUBLICATIONS

Gury Zvilichovsky, Crystal Structure and Tautomerism in 4–Phenylisoxazoles, *J. Heterocyclic Chem.*, 24, 465–470, Mar.–Apr. 1987.

Gury Zvilichovsky and Mordechai David, Acidity and Alkylation of 4–Phenyl–3,5–dihydroxypyrazole and Its Derivatives, *J. Heterocyclic Chem.*, 25, 1307–1310, Sep.–Oct. 1988.

Michael Davis et al., Hydroxyisothiazoles. II Preparation of Isothiazolin–3–ones and Their Methylated Derivatives from the Oxidation of Cyano–Substituted Ditihoacetate Salts, *Australian J. Chem.*, 30, 1815–1818, Mar. 1977.

*Primary Examiner*—Johann Richter
*Assistant Examiner*—Dominic Keating

[57] ABSTRACT

Cyclic amides, including triazole containing cyclic amides, their N-oxides, agriculturally-suitable salts and compositions, and their methods of use as fungicides.

10 Claims, No Drawings

FUNGICIDAL CYCLIC AMIDES

This application is a national filing under 35 USC 371 of International Application No. PCT/US96/02333 filed Feb. 14, 1996, which is a continuation in part, of U.S. patent application Ser. No. 08/393,743 filed Feb. 24, 1995.

BACKGROUND OF THE INVENTION

This invention relates to certain cyclic amides, their N-oxides, agriculturally-suitable salts and compositions, and methods of their use as fungicides.

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds which are more effective, less costly, less toxic, environmentally safer or have different modes of action.

EP 260,794, EP 363,818, EP 398,692, WO 93/07116, WO 93/15046, EP 463,488, and EP 585,751 disclose certain non-cyclic fungicidal amides. The cyclic amides of this invention are not disclosed therein.

EP 508,126, WO 95/01971, U.S. Pat. No. 4,098,896, and WO 92/16510 disclose certain cyclic amides as fungicides, herbicides or insecticides. The cyclic amides of this invention are not disclosed therein.

J. Heterocyclic Chem., (1987), 24, 465, J. Heterocyclic Chem., (1988), 25, 1307, and Australian J. Chem., (1977), 30 (8), 1815 disclose 4-nitrophenyl isoxazoles (i), phenyl pyrazolones (ii), and aryl isothiazolinones (iii) respectively.

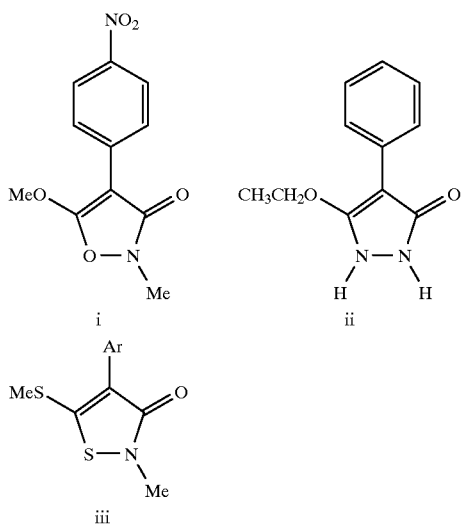

However, no utility as fungicides is alleged and no ortho-substituted compounds of the present invention are disclosed.

SUMMARY OF THE INVENTION

This invention is directed to compounds of Formula I including all geometric and stereoisomers, N-oxides, and agriculturally-suitable salts thereof, agricultural compositions containing them and their use as fungicides:

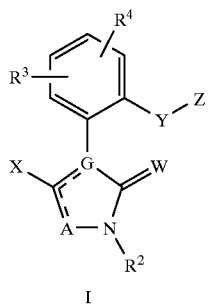

I wherein:
A is O; S; N; $NR^5$; or $CR^{14}$;
G is C or N; provided that when G is C, A is O, S or $NR^5$ and the floating double bond is attached to G; and when G is N, A is N or $CR^{14}$ and the floating double bond is attached to A;
W is O; S; NH; $N(C_1-C_6$ alkyl); or $NO(C_1-C_6$ alkyl);
X is $OR^1$; $S(O)_mR^1$; or halogen;
$R^1$ and $R^5$ are each independently H; $C_1-C_6$ alkyl; $C_1-C_6$ haloalkyl; $C_2-C_6$ alkenyl; $C_2-C_6$ haloalkenyl; $C_2-C_6$ alkynyl; $C_2-C_6$ haloalkynyl; $C_3-C_6$ cycloalkyl; $C_2-C_4$ alkylcarbonyl; or $C_2-C_4$ alkoxycarbonyl;
$R^2$ is H; $C_1-C_6$ alkyl; $C_1-C_6$ haloalkyl; $C_2-C_6$ alkenyl; $C_2-C_6$ haloalkenyl; $C_2-C_6$ alkynyl; $C_2-C_6$ haloalkynyl; $C_3-C_6$ cycloalkyl; $C_2-C_4$ alkylcarbonyl; $C_2-C_4$ alkoxycarbonyl; hydroxy; $C_1-C_2$ alkoxy; or acetyloxy;
$R^3$ and $R^4$ are each independently H; halogen; cyano; nitro; hydroxy; $C_1-C_6$ alkyl; $C_1-C_6$ haloalkyl; $C_2-C_6$ alkenyl; $C_2-C_6$ haloalkenyl; $C_2-C_6$ alkynyl; $C_2-C_6$ haloalkynyl; $C_1-C_6$ alkoxy; $C_1-C_6$ haloalkoxy; $C_2-C_6$ alkenyloxy; $C_2-C_6$ alkynyloxy; $C_1-C_6$ alkylthio; $C_1-C_6$ alkylsulfinyl; $C_1-C_6$ alkylsulfonyl; formyl; $C_2-C_6$ alkylcarbonyl; $C_2-C_6$ alkoxycarbonyl; $NH_2C(O)$; $(C_1-C_4$ alkyl)NHC(O); $(C_1-C_4$ alkyl)$_2$NC(O); $Si(R^{25})_3$; $Ge(R^{25})_3$; $(R^{25})_3Si—C\equiv C—$; or phenyl, phenylethynyl, benzoyl, or phenylsulfonyl each substituted with $R^8$ and optionally substituted with one or more $R^{10}$;
Y is —O—; —S(O)$_n$—; —$NR^6$—; —C(=O)—; —CH$(OR^6)$—; —$CHR^6$—; —$CHR^6CHR^6$—; —$CR^6=CR^6$—; —$C\equiv C$—; —$CHR^6O$—; —$OCHR^6$—; —$CHR^6S(O)_n$—; —$S(O)_nCHR^6$—; —$CHR^6O—N=C(R^7)$—; —$(R^7)C=N—OCH(R^6)$—; —$C(R^7)=N—O$—; —$O—N=C(R^7)$—; —$CHR^6OC(=O)N(R^{15})$—; or a direct bond; and the directionality of the Y linkage is defined such that the moiety depicted on the left side of the linkage is bonded to the phenyl ring and the moiety on the right side of the linkage is bonded to Z;
each $R^6$ is independently H or $C_1-C_3$ alkyl;
$R^7$ is H; $C_1-C_6$ alkyl; $C_1-C_6$ haloalkyl; $C_1-C_6$ alkoxy; $C_1-C_6$ haloalkoxy; $C_1-C_6$ alkylthio; $C_1-C_6$ alkylsulfinyl; $C_1-C_6$ alkylsulfonyl; $C_1-C_6$ haloalkylthio; $C_1-C_6$ haloalkylsulfinyl; $C_1-C_6$ haloalkylsulfonyl; $C_2-C_6$ alkenyl; $C_2-C_6$ haloalkenyl; $C_2-C_6$ alkynyl; $C_2-C_6$ haloalkynyl; $C_3-C_6$ cycloalkyl; $C_2-C_4$ alkylcarbonyl; $C_2-C_4$ alkoxycarbonyl; halogen; cyano; or morpholinyl;
Z is a ring system selected from:
i) 8 to 14-membered fused-bicyclic and fused-tricyclic ring systems which are aromatic or nonaromatic carbocyclic ring systems;

ii) 8 to 14-membered fused-bicyclic and fused-tricyclic ring systems containing one or two nonaromatic rings that each include one or two Q as ring members and one or two ring members independently selected from C(=O) and S(O)$_2$, and any remaining rings as aromatic carbocyclic rings;

iii) N-oxides of 5 to 10-membered monocyclic and fused-bicyclic aromatic heterocyclic ring systems containing at least one nitrogen, each heterocyclic ring system containing 0 to 3 additional heteroatoms independently selected from the group nitrogen, oxygen, and sulfur, provided that each heterocyclic ring system contains no more than 2 oxygens, and no more than 2 sulfurs;

iv) adamantyl;

each ring system of i), ii), iii) and iv) substituted with $R^9$ and optionally substituted with one or more $R^{10}$;

each Q is independently selected from the group —CHR$^{13}$—, —NR$^{13}$—, —O—, and —S(O)$_p$—;

$R^8$ is H; 1–2 halogen; $C_1$–$C_6$ alkyl; $C_1$–$C_6$ haloalkyl; $C_1$–$C_6$ alkoxy; $C_1$–$C_6$ haloalkoxy; $C_2$–$C_6$ alkenyl; $C_2$–$C_6$ haloalkenyl; $C_2$–$C_6$ alkynyl; $C_1$–$C_6$ alkylthio; $C_1$–$C_6$ haloalkylthio; $C_1$–$C_6$ alkylsulfinyl; $C_1$–$C_6$ alkylsulfonyl; $C_3$–$C_6$ cycloalkyl; $C_3$–$C_6$ alkenyloxy; CO$_2$ ($C_1$–$C_6$ alkyl); NH($C_1$–$C_6$ alkyl); N($C_1$–$C_6$ alkyl)$_2$; cyano; nitro; SiR$^{19}$R$^{20}$R$^{21}$; or GeR$^{19}$R$^{20}$R$^{21}$;

$R^9$ is H; 1–2 halogen; $C_1$–$C_6$ alkyl; $C_1$–$C_6$ haloalkyl; $C_1$–$C_6$ alkoxy; $C_1$–$C_6$ haloalkoxy; $C_2$–$C_6$ alkenyl; $C_2$–$C_6$ haloalkenyl; $C_2$–$C_6$ alkynyl; $C_1$–$C_6$ alkylthio; $C_1$–$C_6$ haloalkylthio; $C_1$–$C_6$ alkylsulfinyl; $C_1$–$C_6$ alkylsulfonyl; $C_3$–$C_6$ cycloalkyl; $C_3$–$C_6$ alkenyloxy; CO$_2$ ($C_1$–$C_6$ alkyl); NH($C_1$–$C_6$ alkyl); N($C_1$–$C_6$ alkyl)$_2$; —C(R$^{18}$)=NOR$^{17}$; cyano; nitro; SF$_5$; SiR$^{22}$R$^{23}$R$^{24}$; or GeR$^{22}$R$^{23}$R$^{24}$; or $R^9$ is phenyl, benzyl, benzoyl, phenoxy, pyridinyl, pyridinyloxy, thienyl, thienyloxy, furanyl, pyrimidinyl, or pyrimidinyloxy each optionally substituted with one of $R^{11}$, $R^{12}$, or both $R^{11}$ and $R^{12}$;

each $R^{10}$ is independently halogen; $C_1$–$C_4$ alkyl; $C_1$–$C_4$ haloalkyl; $C_1$–$C_4$ alkoxy; nitro; or cyano; or when $R^9$ and an $R^{10}$ are attached to adjacent atoms on Z, $R^9$ and said adjacently attached $R^{10}$ can be taken together as —OCH$_2$— or —OCH$_2$CH$_2$O—; each CH$_2$ group of said taken together $R^9$ and $R^{10}$ optionally substituted with 1–2 halogen; or when Y and an $R^{10}$ are attached to adjacent atoms on Z and Y is —CHR$^6$O—N=C(R$^7$)— or —O—N=C(R$^7$)—, $R^7$ and said adjacently attached $R^{10}$ can be taken together as —(CH$_2$)$_r$—J— such that J is attached to Z;

J is —CH$_2$—; —CH$_2$CH$_2$—; —OCH$_2$—; —CH$_2$O—; —SCH$_2$—; —CH$_2$S—; —N(R$^{16}$)CH$_2$—; or —CH$_2$N(R$^{16}$)—; each CH$_2$ group of said J optionally substituted with 1 to 2 CH$_3$;

$R^{11}$ and $R^{12}$ are each independently halogen; $C_1$–$C_4$ alkyl; $C_1$–$C_4$ haloalkyl; $C_1$–$C_4$ alkoxy; $C_1$–$C_4$ haloalkoxy; nitro; cyano; Si(R$^{25}$)$_3$; or Ge(R$^{25}$)$_3$;

each $R^{13}$ is independently H; $C_1$–$C_6$ alkyl; $C_1$–$C_6$ haloalkyl; or phenyl optionally substituted with halogen, $C_1$–$C_4$ alkyl, $C_1$–$C_4$ haloalkyl, $C_1$–$C_4$ alkoxy, $C_1$–$C_4$ haloalkoxy, nitro or cyano;

$R^{14}$ is H; halogen; $C_1$–$C_6$ alkyl; $C_1$–$C_6$ haloalkyl; $C_2$–$C_6$ alkenyl; $C_2$–$C_6$ haloalkenyl; $C_2$–$C_6$ alkynyl; $C_2$–$C_6$ haloalkynyl; or $C_3$–$C_6$ cycloalkyl;

$R^{15}$, $R^{16}$, $R^{17}$, and $R^{18}$ are each independently H; $C_1$–$C_3$ alkyl; or phenyl optionally substituted with halogen, $C_1$–$C_4$ alkyl, $C_1$–$C_4$ haloalkyl, $C_1$–$C_4$ alkoxy, $C_1$–$C_4$ haloalkoxy, nitro or cyano;

$R^{19}$, $R^{20}$, $R^{21}$, $R^{22}$, $R^{23}$, and $R^{24}$ are each independently $C_1$–$C_6$ alkyl; $C_2$–$C_6$ alkenyl; $C_1$–$C_4$ alkoxy; or phenyl;

each $R^{25}$ is independently $C_1$–$C_4$ alkyl;

m, n and p are each independently 0, 1 or 2; and r is 0 or 1.

DETAILS OF THE INVENTION

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as vinyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkenyloxy" includes straight-chain or branched alkenyloxy moieties. Examples of "alkenyloxy" include H$_2$C=CHCH$_2$O, (CH$_3$)$_2$C=CHCH$_2$O, (CH$_3$)CH=CHCH$_2$O, (CH$_3$)CH=C(CH$_3$)CH$_2$O and CH$_2$=CHCH$_2$CH$_2$O. "Alkynyloxy" includes straight-chain or branched alkynyloxy moieties. Examples of "alkynyloxy" include HC≡CCH$_2$O, CH$_3$C≡CCH$_2$O and CH$_3$CCH$_2$CH$_2$O. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include CH$_3$S(O), CH$_3$CH$_2$S(O), CH$_3$CH$_2$CH$_2$S(O), (CH$_3$)$_2$CHS(O) and the different butylsulfinyl, pentylsulfinyl and hexylsulfinyl isomers. Examples of "alkylsulfonyl" include CH$_3$S(O)$_2$, CH$_3$CH$_2$S(O)$_2$, CH$_3$CH$_2$CH$_2$S(O)$_2$, (CH$_3$)$_2$CHS(O)$_2$ and the different butylsulfonyl, pentylsulfonyl and hexylsulfonyl isomers. "Cycloalkyl" includes, for example, cyclopropyl, cyclobutyl, cyclopentyl, and cyclohexyl. The term "aromatic carbocyclic ring system" includes fully aromatic carbocycles and carbocycles in which at least one ring of a polycyclic ring system is aromatic (where aromatic indicates that the Hückel rule is satisfied). The term "non-aromatic carbocyclic ring system" denotes fully saturated carbocycles as well as partially or fully unsaturated carbocycles where the Hückel rule is not satisfied by any of the rings in the ring system. The term "aromatic heterocyclic ring system" includes fully aromatic heterocycles and heterocycles in which at least one ring of a polycyclic ring system is aromatic (where aromatic indicates that the Hückel rule is satisfied). The heterocyclic ring systems can be attached through any available carbon or nitrogen by replacement of a hydrogen on said carbon or nitrogen. One skilled in the art will appreciate that not all nitrogen containing heterocycles can form N-oxides since the nitrogen requires an available lone pair for oxidation to the oxide; one skilled in the art will recognize those nitrogen containing heterocycles which can form N-oxides.

The term "halogen", either alone or in compound words such as "haloalkyl", includes fluorine, chlorine, bromine or iodine. The term "1–2 halogen" indicates that one or two of the available positions for that substituent may be halogen which are independently selected. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", and the like, are defined analogously to the term "haloalkyl". Examples of "haloalkenyl" include $(Cl)_2C=CHCH_2$ and $CF_3CH_2CH=CHCH_2$. Examples of "haloalkynyl" include $HC≡CCHCl$, $CF_3C≡C$, $CCl_3C≡C$ and $FCH_2C≡CCH_2$. Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$. Examples of "haloalkylsulfonyl" include $CF_3S(O)_2$, $CCl_3S(O)_2$, $CF_3CH_2S(O)_2$ and $CF_3CF_2S(O)_2$.

The total number of carbon atoms in a substituent group is indicated by the "$C_i$–$C_j$" prefix where i and j are numbers from 1 to 6. For example, $C_1$–$C_3$ alkylsulfonyl designates methylsulfonyl through propylsulfonyl; and $C_2$ alkoxy designates $CH_3CH_2O$. Examples of "alkylcarbonyl" include $C(O)CH_3$, $C(O)CH_2CH_2CH_3$ and $C(O)CH(CH_3)_2$. Examples of "alkoxycarbonyl" include $CH_3OC(=O)$, $CH_3CH_2OC(=O)$, $CH_3CH_2CH_2OC(=O)$, $(CH_3)_2CHOC(=O)$ and the different butoxy- or pentoxycarbonyl isomers. In the above recitations, when a compound of Formula I is comprised of one or more heterocyclic rings, all substituents are attached to these rings through any available carbon or nitrogen by replacement of a hydrogen on said carbon or nitrogen.

When a group contains a substituent which can be hydrogen, for example $R^3$ or $R^9$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula I, N-oxides and agriculturally suitable salts thereof. The compounds of the invention may be present as a mixture of stereoisomers, individual stereoisomers, or as an optically active form.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group such as a phenol.

Preferred compounds for reasons of better activity and/or ease of synthesis are:

Preferred 1. Compounds of Formula I above, and N-oxides and agriculturally-suitable salts thereof, wherein:

W is O;

$R^1$ is $C_1$–$C_3$ alkyl or $C_1$–$C_3$ haloalkyl;

$R^2$ is H; $C_1$–$C_6$ alkyl; $C_1$–$C_6$ haloalkyl; or $C_3$–$C_6$ cycloalkyl;

$R^3$ and $R^4$ are each independently H; halogen; cyano; nitro; $C_1$–$C_6$ alkyl; $C_1$–$C_6$ haloalkyl; $C_1$–$C_6$ alkoxy; $C_1$–$C_6$ haloalkoxy; or $C_1$–$C_6$ alkylthio;

Y is —O—; —CH=CH—; —C≡C—; —CH$_2$O—; —OCH$_2$—; —CH$_2$S(O)$_n$—; —CH$_2$O—N=C(R$^7$)—; —C(R$^7$)=N—O—; —CH$_2$OC(O)NH—; or a direct bond;

$R^7$ is H; $C_1$–$C_6$ alkyl; $C_1$–$C_6$ haloalkyl; $C_1$–$C_6$ alkoxy; $C_2$–$C_6$ alkenyl; $C_2$–$C_6$ alkynyl; $C_3$–$C_6$ cycloalkyl; halogen; or cyano; or when Y and an $R^{10}$ are attached to adjacent atoms on Z and Y is —CH$_2$O—N=C(R$^7$)—, $R^7$ and said adjacently attached $R^{10}$ can be taken together as —(CH$_2$)$_r$—J— such that J is attached to Z;

Z is selected from the group

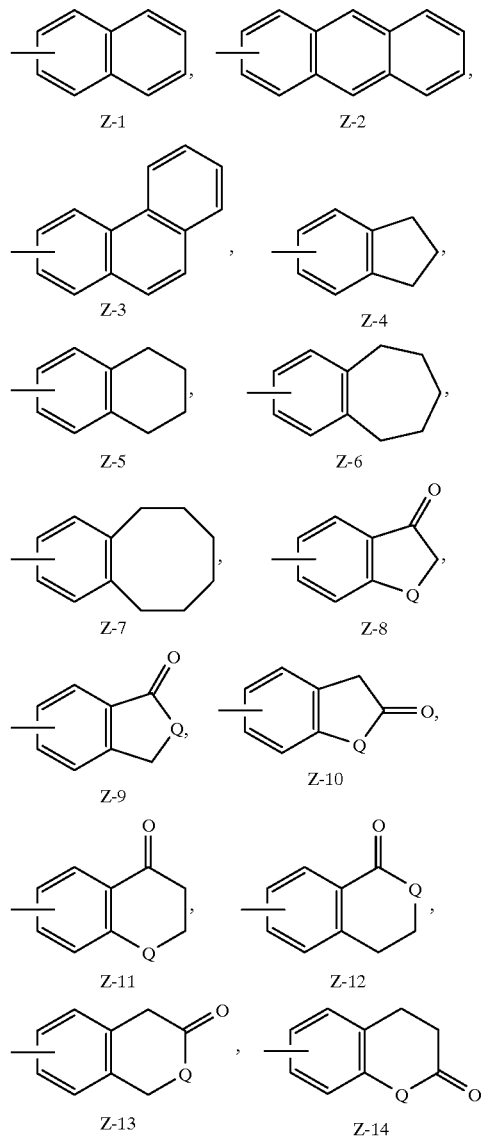

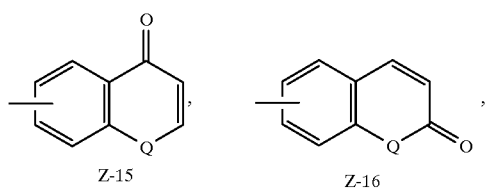
Z-15, Z-16
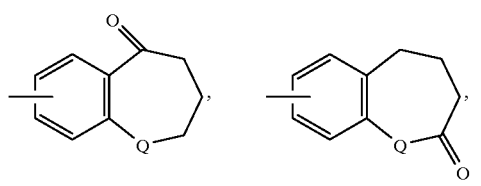
Z-17, Z-18
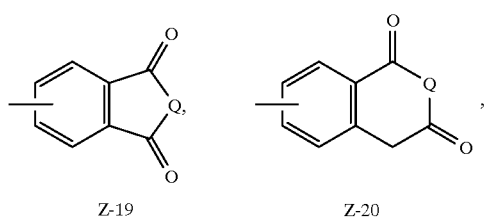
Z-19, Z-20
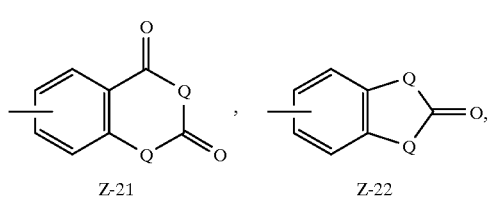
Z-21, Z-22
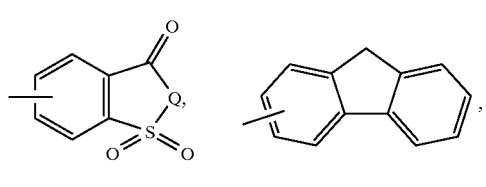
Z-23, Z-24
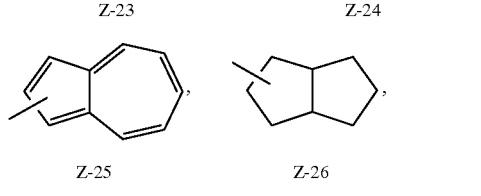
Z-25, Z-26
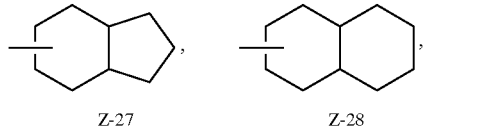
Z-27, Z-28
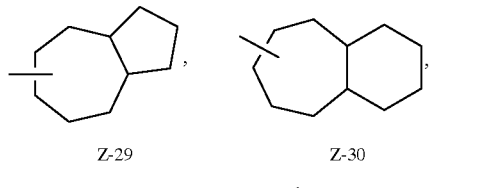
Z-29, Z-30
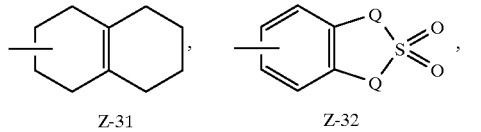
Z-31, Z-32
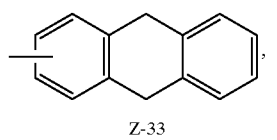
Z-33
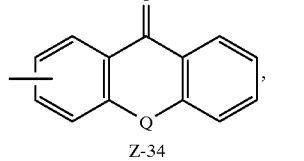
Z-34
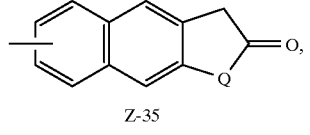
Z-35
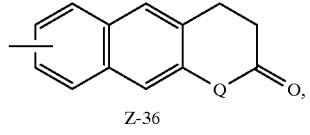
Z-36
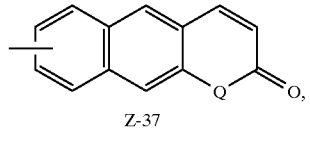
Z-37
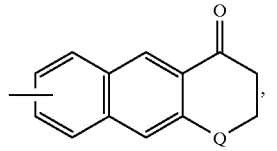
Z-38
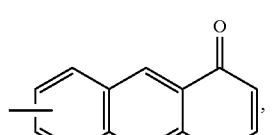
Z-39
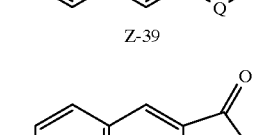
Z-40
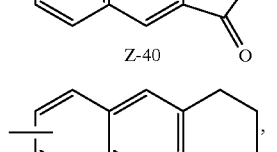
Z-41
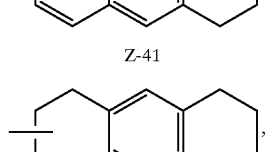
Z-42

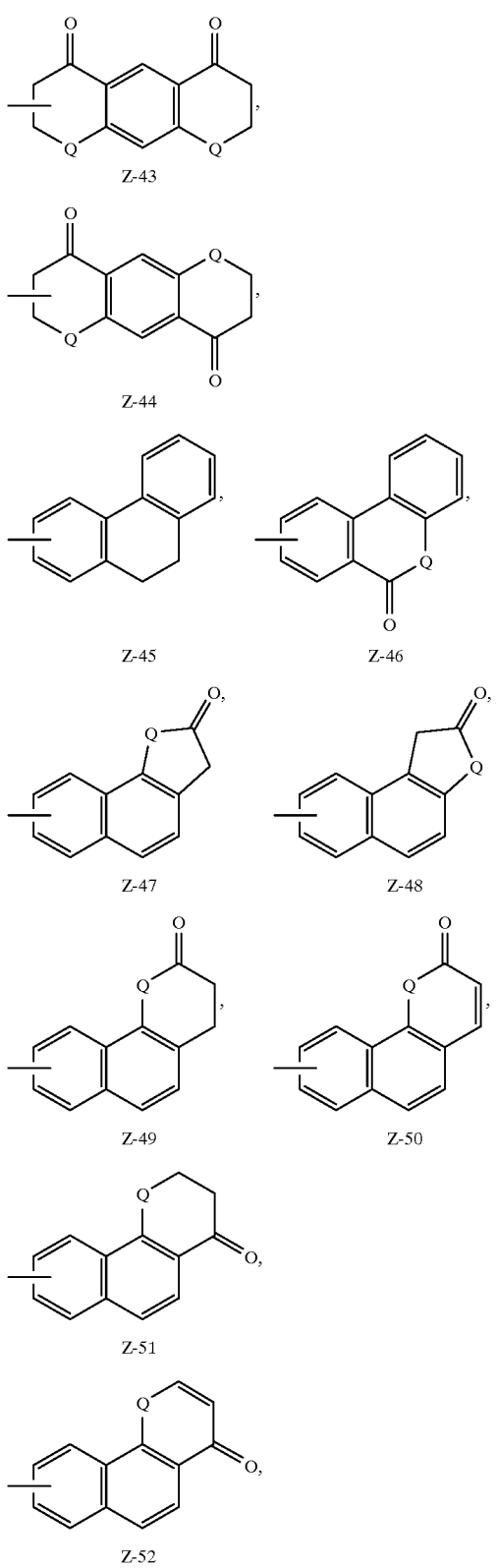
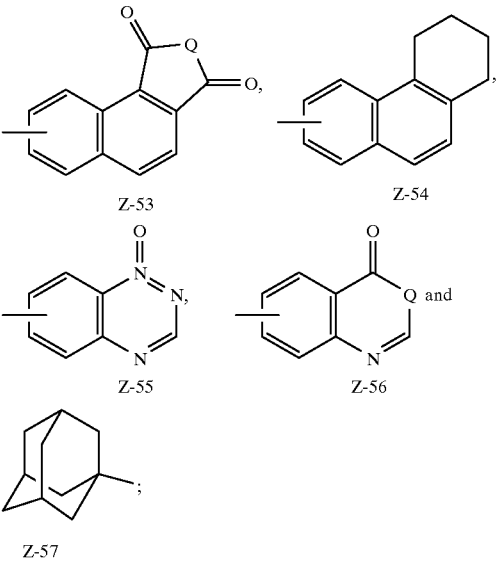

where the point of attachment with Y is selected from any available position on the entire multicyclic ring system, each multicyclic ring system substituted with $R^9$ and optionally substituted with one or more $R^{10}$; and $R^9$ is H; 1–2 halogen; $C_1$–$C_6$ alkyl; $C_1$–$C_6$ haloalkyl; $C_1$–$C_6$ alkoxy; $C_1$–$C_6$ haloalkoxy; $C_1$–$C_6$ alkylthio; cyano; $CO_2(C_1$–$C_6$ alkyl); $NH(C_1$–$C_6$ alkyl); $N(C_1$–$C_6$ alkyl$)_2$; $SiR^{22}R^{23}R^{24}$; or $GeR^{22}R^{23}R^{24}$; or $R^9$ is $C_3$–$C_6$ cycloalkyl, phenyl, phenoxy, pyridinyl, pyridinyloxy, pyrimidinyl, or pyrimidinyloxy, each optionally substituted with one of $R^{11}$, $R^{12}$, or both $R^{11}$ and $R^{12}$.

Preferred 2. Compounds of Preferred 1 wherein:

Z is selected from the group Z-1 to Z-24 and Z-55 to Z-57, each multicyclic ring system substituted with $R^9$ and optionally substituted with one or more $R^{10}$;

$R^7$ is H; $C_1$–$C_6$ alkyl; $C_1$–$C_6$ haloalkyl; $C_1$–$C_6$ alkoxy; $C_2$–$C_6$ alkenyl; $C_2$–$C_6$ alkynyl; cyclopropyl; or cyano; or when Y and an $R^{10}$ are attached to adjacent atoms on Z and Y is —$CH_2O$—N=C($R^7$)—, $R^7$ and said adjacently attached $R^{10}$ can be taken together as —$(CH_2)_r$—J— such that J is attached to Z;

J is —$CH_2$— or —$CH_2CH_2$—; and r is 1.

Preferred 3. Compounds of Preferred 2 wherein:

A is O; N; $NR^5$; or $CR^{14}$;

X is $OR^1$;

$R^1$ is $C_1$–$C_3$ alkyl;

$R^2$ is H or $C_1$–$C_2$ alkyl;

$R^3$ and $R^4$ are independently H; halogen; cyano; methyl; trifluoromethyl; methoxy; trifluoromethoxy; or methylthio;

Y is —O—; —CH=CH—; —$CH_2O$—; —$CH_2O$—N=C($R^7$)—; or —$CH_2OC$(=O)NH—;

$R^7$ is H; $C_1$–$C_3$ alkyl; $C_1$–$C_3$ haloalkyl; $C_1$–$C_3$ alkoxy; or cyclopropyl; and Z is selected from the group Z-1, Z-5, Z-19, Z-21, Z-22, Z-23, Z-24, Z-55, Z-56, and Z-57, each multicyclic ring system substituted with $R^9$ and optionally substituted with one or more $R^{10}$.

Preferred 4. Compounds of Preferred 3 wherein:

A is O or $NR^5$;

G is C;

Y is —O—; —$CH_2O$—; or —$CH_2O$—N=C($R^7$)—; and $R^7$ is H; $C_1$–$C_2$ alkyl; $C_1$–$C_2$ haloalkyl; $C_1$–$C_2$ alkoxy; or cyclopropyl.

Preferred 5. Compounds of Preferred 4 wherein:

$R^1$ is methyl; and $R^2$ is methyl.

Preferred 6. Compounds of Preferred 3 wherein:

A is N or $CR^{14}$;

G is N;

Y is —O—; —$CH_2O$—; or —$CH_2O$—N=C($R^7$)—; and $R^7$ is H; $C_1$–$C_2$ alkyl; $C_1$–$C_2$ haloalkyl; methoxy; or cyclopropyl.

Preferred 7. Compounds of Preferred 6 wherein:

$R^1$ is methyl; and $R^2$ is methyl.

Most preferred are compounds of Preferred 7 selected from the group:

2,4-dihydro-5-methoxy-2-methyl-4-[2-[[[[1-(2-naphthalenyl)ethylidene]amino]oxy]methyl]phenyl]-3H-1,2,4-triazol-3-one;

2,4-dihydro-5-methoxy-2-methyl-4-[2-[[[[1-(5,6,7,8-tetrahydro-2-naphthalenyl)ethylidene]amino]oxy]methyl]phenyl]-3H-1,2,4-triazol-3-one; and 2,4-dihydro-5-methoxy-2-methyl-4-[2-methyl-6-[[[[1-(2-naphthalenyl)ethylidene]amino]oxy]methyl]phenyl]-3H-1,2,4-triazol-3-one.

This invention also relates to fungicidal compositions comprising fungicidally effective amounts of the compounds of the invention and at least one of a surfactant, a solid diluent or a liquid diluent. The preferred compositions of the present invention are those which comprise the above preferred compounds.

This invention also relates to a method for controlling plant diseases caused by fungal plant pathogens comprising applying to the plant or portion thereof, or to the plant seed or seedling, a fungicidally effective amount of the compounds of the invention (e.g., as a composition described herein). The preferred methods of use are those involving the above preferred compounds.

Of note are embodiments where W is O or S; embodiments where $R^1$, $R^2$, and $R^5$ are each independently H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl, $C_3$–$C_6$ cycloalkyl, $C_2$–$C_4$ alkylcarbonyl, or $C_2$–$C_4$ alkoxycarbonyl; embodiments where $R^3$ and $R^4$ are each independently H, halogen, cyano, nitro, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl, $C_1$–$C_6$ alkoxy, $C_1$–$C_6$ haloalkoxy, $C_2$–$C_6$ alkenyloxy, $C_2$–$C_6$ alkynyloxy, or phenyl substituted with $R^8$ and optionally substituted with one or more $R^{10}$; embodiments where $R^3$ and $R^4$ are each independently H, halogen, cyano, nitro, $C_1$–$C_6$ alkyl, $C_1$–$C_6$ haloalkyl, $C_1$–$C_6$ alkoxy, or $C_1$–$C_6$ haloalkoxy; embodiments where $R^3$ and $R^4$ are each H; embodiments where $R^7$ is H, $C_1$–$C_6$ alkyl, $C_1$–$C_6$ haloalkyl, $C_2$–$C_6$ alkenyl, $C_2$–$C_6$ alkynyl, cyclopropyl or cyano; embodiments where $R^7$ is H, $C_1$–$C_3$ alkyl, $C_1$–$C_3$ haloalkyl or cyclopropyl; embodiments where $R^7$ is H, $C_1$–$C_2$ alkyl, $C_1$–$C_2$ haloalkyl or cyclopropyl; embodiments where Z is a multicyclic ring system selected from: i) 8–14-membered fused-bicyclic and fused-tricyclic ring systems which are aromatic or nonaromatic carbocyclic ring systems and ii) 8–14-membered fused-bicyclic and fused-tricyclic ring systems containing one or two nonaromatic rings that each include one or two Q as ring members and one or two ring members independently selected from C(=O) and S(O)$_2$, and any remaining rings as aromatic carbocyclic rings, each multicyclic ring system substituted with $R^9$ and optionally substituted with one or more $R^{10}$; embodiments where Z is selected from the group Z-1 to Z-54, each multicyclic ring system substituted with $R^9$ and optionally substituted with one or more $R^{10}$; embodiments where Z is selected from the group Z-1 to Z-24, each multicyclic ring system substituted with $R^9$ and optionally substituted with one or more $R^{10}$; embodiments where Z is selected from the group Z-1, Z-5, Z-2 1, Z-22, Z-23 and Z-24, each multicyclic ring system substituted with $R^9$ and optionally substituted with one or more $R^{10}$; embodiments where $R^9$ is other than $SF_5$; and embodiments where $R^{19}$, $R^{20}$, $R^{21}$, $R^{22}$, $R^{23}$, and $R^{24}$ are each independently $C_1$–$C_6$ alkyl, $C_1$–$C_4$ alkoxy, or phenyl.

The compounds of Formula I can be prepared by one or more of the following methods and variations as described in Schemes 1–33. The definitions of A, G, W, X, $R^1$–$R^{25}$, Y, Z, Q, J, m, n, p and r in the compounds of Formulae 1–55 below are as defined above in the Summary of the Invention. Compounds of Formulae Ia–In are various subsets of the compounds of Formula I, and all substituents for Formulae Ia–In are as defined above for Formula I.

One skilled in the art will recognize that some compounds of Formula I can exist in one or more tautomeric forms. For example, a compound of Formula I wherein $R^2$ is H may exist as tautomer Ia or Ib, or both Ia and Ib. The present invention comprises all tautomeric forms of compounds of Formula I.

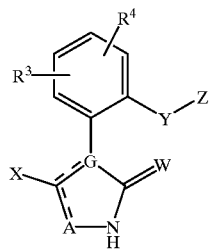

Ia

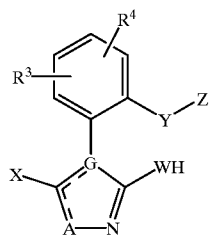

Ib

The compounds of Formula I can be prepared as described below in Procedures 1) to 5). Procedures 1) to 4) describe syntheses involving construction of the amide ring after the formation of the aryl moiety. Procedure 5) describes syntheses of the aryl moiety with the amide ring already in place.

1) Alkylation Procedures

The compounds of Formula I are prepared by treating compounds of Formula 1 with an appropriate alkyl transfer reagent in an inert solvent with or without additional acidic or basic reagents or other reagents (Scheme 1). Suitable solvents are selected from the group consisting of polar aprotic solvents such as acetonitrile, dimethylformamide or dimethyl sulfoxide; ethers such as tetrahydrofuran, dimethoxyethane, or diethyl ether; ketones such as acetone or 2-butanone; hydrocarbons such as toluene or benzene; and halocarbons such as dichloromethane or chloroform.

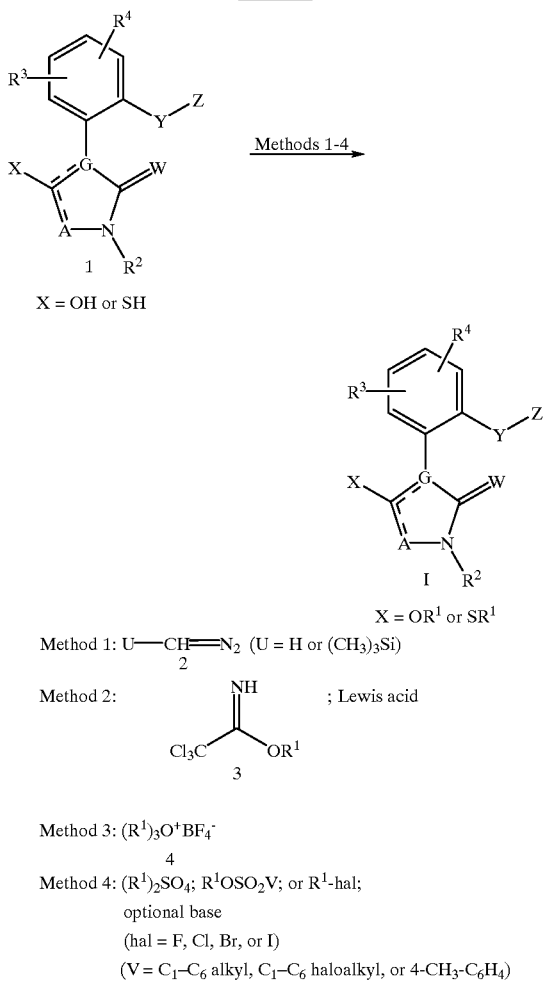

For example, compounds of Formula I can be prepared by the action of diazoalkane reagents of Formula 2 such as diazomethane (U=H) or trimethylsilyldiazomethane (U=(CH$_3$)$_3$Si) on compounds of dicarbonyl compounds of Formula 1 (Method 1). Use of trimethylsilyldiazomethane requires a protic cosolvent such as methanol. For examples of these procedures, see Chem. Pharm. Bull., (1984), 32, 3759.

As indicated in Method 2, compounds of Formula I can also be prepared by contacting carbonyl compounds of Formula 1 with alkyl trichloroacetimidates of Formula 3 and a Lewis acid catalyst. Suitable Lewis acids include trimethylsilyl triflate and tetrafluoroboric acid. The alkyl trichloroacetimidates can be prepared from the appropriate alcohol and trichloroacetonitrile as described in the literature (J. Danklmaier and H. Hönig, Synth. Commun., (1990), 20, 203).

Compounds of Formula I can also be prepared from compounds of Formula 1 by treatment with a trialkyloxonium tetrafluoroborate (i.e., Meerwein's salt) of Formula 4 (Method 3). The use of trialkyloxonium salts as powerful alkylating agents is well known in the art (see U. Schöllkopf, U. Groth, C. Deng, Angew. Chem., Int. Ed. Engl., (1981), 20, 798).

Other alkylating agents which can convert carbonyl compounds of Formula 1 to compounds of Formula I are dialkyl sulfates such as dimethyl sulfate, haloalkyl sulfonates such as methyl trifluoromethanesulfonate, and alkyl halides such as iodomethane and propargyl bromide (Method 4). These alkylations can be conducted with or without additional base. Appropriate bases include alkali metal alkoxides such as potassium tert-butoxide, inorganic bases such as sodium hydride and potassium carbonate, or tertiary amines such as triethylamine, pyridine, 1,8-diazabicyclo[5.4.0]undec-7-ene (DBU), and triethylenediamine. See R. E. Benson, T. L. Cairns, J. Am. Chem. Soc., (1948), 70, 2115 for alkylation examples using agents of this type.

Compounds of Formula 1a (compounds of Formula 1 wherein G=C, W=O and X=OH) can be prepared by condensation of malonates or malonate derivatives of Formula 5 with an ambident nucleophile of Formula 6 (Scheme 2). The nucleophiles of Formula 6 are N-substituted hydroxylamines (HO—NHR$^2$) and substituted hydrazines (HN(R$^5$)—NHR$^2$). Examples of such nucleophiles are N-methylhydroxylamine and methylhydrazine. The malonate esters of Formula 5 can be prepared by methods described hereinafter. The esters of Formula 5 can also be activated by first hydrolyzing the ester to form the corresponding carboxylic acid, and then converting the acid into the acid chloride (T=Cl) using thionyl chloride or oxalyl chloride, or into the acyl imidazole (T=1-imidazolyl) by treating with 1,1'-carbonyldiimidazole.

Compounds of Formula 1aa can be prepared by reaction of nitrile esters of Formula 5b with ambident nucleophiles of Formula 6. See M. Scobie and G. Tennant, J. Chem. Soc., Chem. Comm., (1994), 2451. Alkylation of 1aa with alkyl halides in the presence of base provides compounds of Formula 1ab. Alternatively, treatment of 1aa with alkylamines or alkoxyamines provides compounds of Formula 1ab.

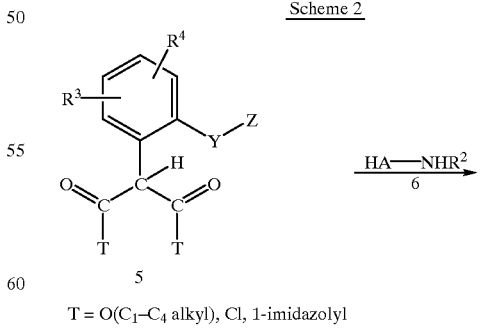

Scheme 2

T = O(C$_1$–C$_4$ alkyl), Cl, 1-imidazolyl

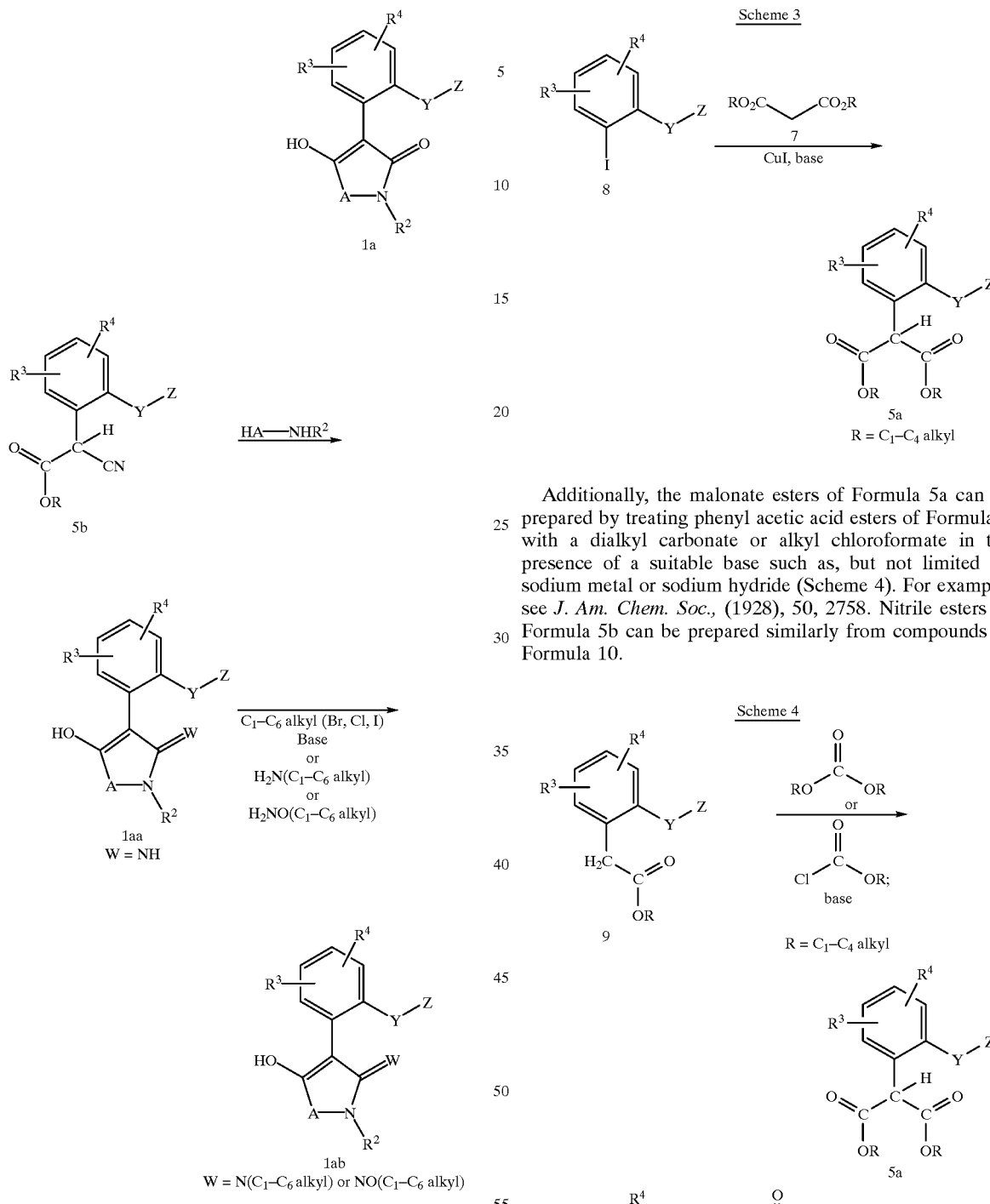

Esters of Formula 5a can be prepared from copper (I)-catalyzed reaction of malonate esters of Formula 7 with substituted halobenzenes of Formula 8 according to methods adapted from A. Osuka, T. Kobayashi and H. Suzuki, *Synthesis,* (1983), 67 and M. S. Malamas, T. C. Hohman, and J. Millen, *J. Med. Chem.,* 1994, 37, 2043–2058, and illustrated in Scheme 3. Nitrile esters of Formula 5b can be prepared similarly from compounds of Formula 10.

Additionally, the malonate esters of Formula 5a can be prepared by treating phenyl acetic acid esters of Formula 9 with a dialkyl carbonate or alkyl chloroformate in the presence of a suitable base such as, but not limited to, sodium metal or sodium hydride (Scheme 4). For example, see *J. Am. Chem. Soc.,* (1928), 50, 2758. Nitrile esters of Formula 5b can be prepared similarly from compounds of Formula 10.

-continued

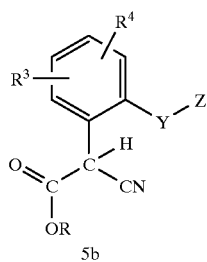

Esters of Formula 9 can be prepared from acid-catalyzed alcoholysis of phenyl acetonitriles of Formula 10 or esterification of phenyl acetic acids of Formula 11 as illustrated in Scheme 5 (see *Org. Synth.*, Coll. Vol. I, (1941), 270).

Scheme 5

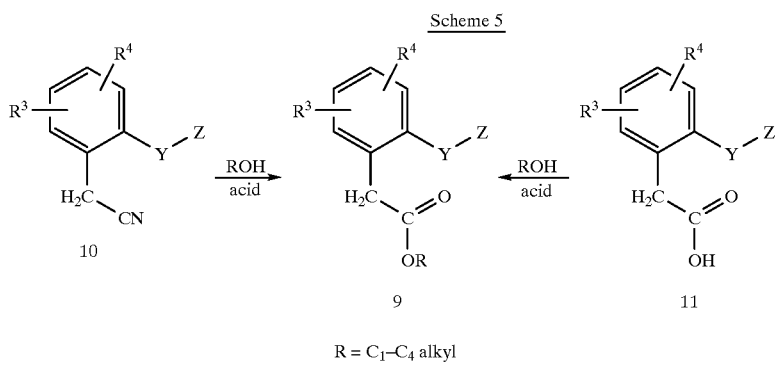

$R = C_1-C_4$ alkyl

Phenyl acetic acid esters of Formula 9a can also be prepared by copper (I)-catalyzed condensation of phenyl halides of Formula 12 with compounds of Formula 13 as described in EP 307,103 and illustrated below in Scheme 6.

Scheme 6

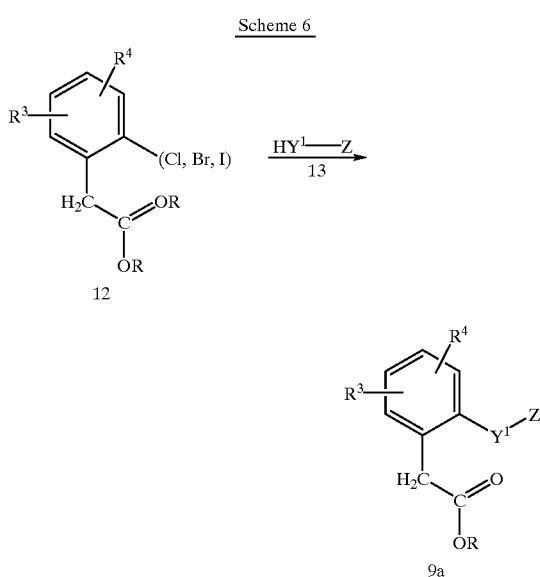

$R = C_1-C_4$ alkyl
$Y^1 = O, S, OCHR^6, SCHR^6, O\!\!-\!\!N\!\!=\!\!C(R^7), NR^6$ Some esters of Formula 9 (Formula 9b) can also be prepared by forming the $Y^2$ bridge using conventional nucleophilic substitution chemistry (Scheme 7). Displacement of an appropriate leaving group (Lg) in electrophiles of Formula 15 or 16 with a nucleophilic ester of Formula 14 affords compounds of Formula 9b. A base, for example sodium hydride, is used to generate the corresponding alkoxide or thioalkoxide of the compound of Formula 14.

Scheme 7

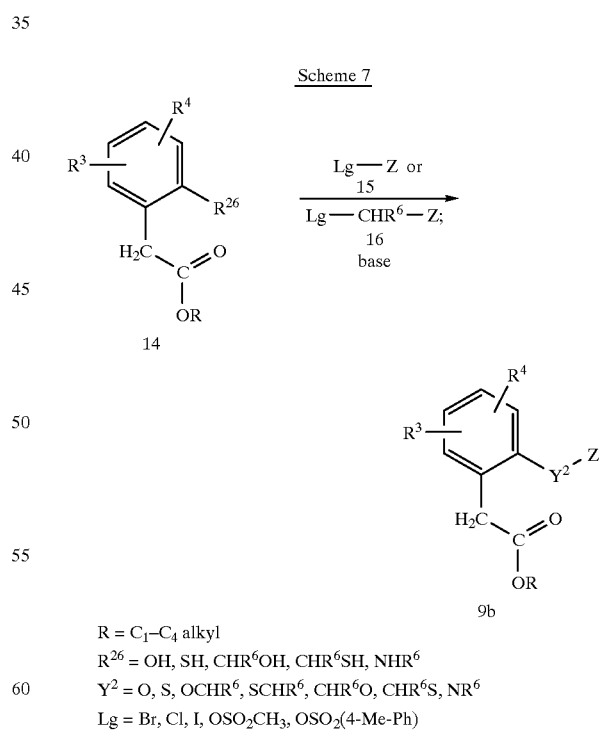

$R = C_1-C_4$ alkyl
$R^{26} = OH, SH, CHR^6OH, CHR^6SH, NHR^6$
$Y^2 = O, S, OCHR^6, SCHR^6, CHR^6O, CHR^6S, NR^6$
$Lg = Br, Cl, I, OSO_2CH_3, OSO_2(4\text{-Me-Ph})$ Some esters of Formula 9 (Formula 9e) can also be prepared by forming the $Y^3$ bridge from substituted hydroxylamine 9d and carbonyl compounds 14a. The hydroxylamine 9d is in turn prepared from esters 9c. This method has been described in EP 600,835 and illustrated in Scheme 8.

Scheme 8

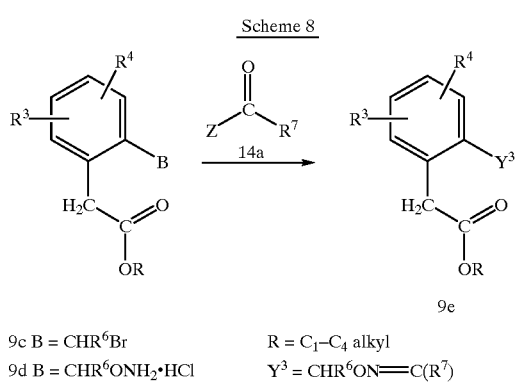

9c B = CHR$^6$Br   R = C$_1$–C$_4$ alkyl
9d B = CHR$^6$ONH$_2$·HCl   Y$^3$ = CHR$^6$ON═C(R$^7$)

2) Displacement and Conjugate Addition/Elimination Procedures

Compounds of Formula I can also be prepared by reaction of Formula 17 compounds with alkali metal alkoxides (R$^1$O-M$^+$) or alkali metal thioalkoxides (R$^1$S-M$^+$) in a suitable solvent (Scheme 9). The leaving group Lg$^1$ in the amides of Formula 17 are any group known in the art to undergo a displacement reaction of this type. Examples of suitable leaving groups include chlorine, bromine, and sulfonyl and sulfonate groups. Examples of suitable inert solvents are dimethylformamide or dimethyl sulfoxide.

Scheme 9

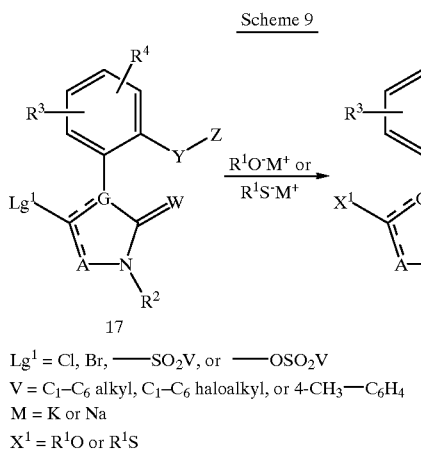

Lg$^1$ = Cl, Br, ──SO$_2$V, or ──OSO$_2$V
V = C$_1$–C$_6$ alkyl, C$_1$–C$_6$ haloalkyl, or 4-CH$_3$─C$_6$H$_4$
M = K or Na
X$^1$ = R$^1$O or R$^1$S Compounds of Formula 17a can be prepared from compounds of Formula 1b (compounds of Formula 1 wherein X is OH) by reaction with halogenating agents such as thionyl chloride or phosphorus oxybromide to form the corresponding β-halo-substituted derivatives (Scheme 10). Alternatively, compounds of Formula 1b can be treated with an alkylsulfonyl halide or haloalkylsulfonyl anhydride, such as methanesulfonyl chloride, p-toluenesulfonyl chloride, and trifluoromethanesulfonyl anhydride, to form the corresponding β-alkylsulfonate of Formula 17a. The reaction with the sulfonyl halides may be performed in the presence of a suitable base (e.g., triethylamine).

Scheme 10

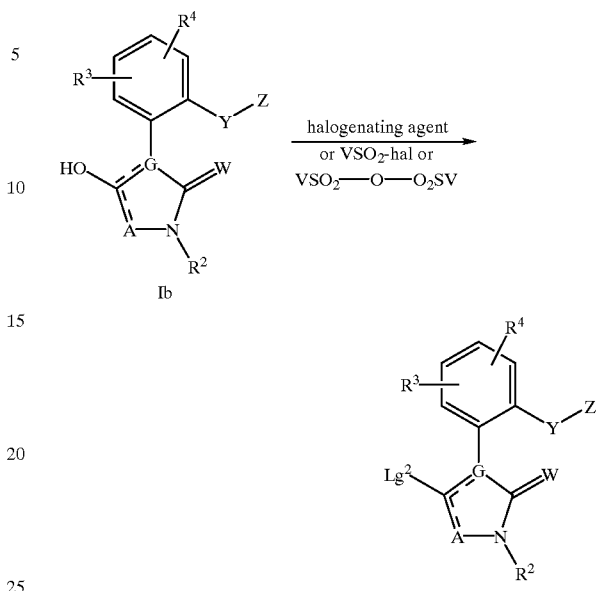

Lg$^2$ = Cl, Br, or ──OSO$_2$V
V = C$_1$–C$_6$ alkyl, C$_1$–C$_6$ haloalkyl, or 4-CH$_3$─C$_6$H$_4$
hal = Br, Cl or F As illustrated in Scheme 11, sulfonyl compounds of Formula 17b can be prepared by oxidation of the corresponding thio compound of Formula 18 using well-known methods for the oxidation of sulfur (see Schrenk, K. In *The Chemistry of Sulphones and Sulphoxides*; Patai, S. et al., Eds.; Wiley: N.Y., 1988). Suitable oxidizing reagents include meta-chloro-peroxybenzoic acid, hydrogen peroxide and Oxone® (KHSO$_5$).

Scheme 11

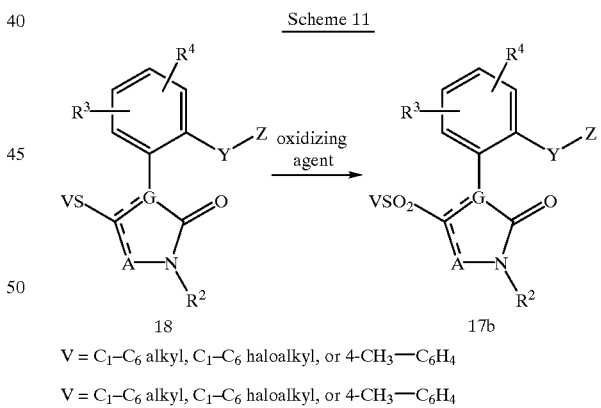

V = C$_1$–C$_6$ alkyl, C$_1$–C$_6$ haloalkyl, or 4-CH$_3$─C$_6$H$_4$
V = C$_1$–C$_6$ alkyl, C$_1$–C$_6$ haloalkyl, or 4-CH$_3$─C$_6$H$_4$ Alternatively, halo-compounds of Formula 17c (compounds of Formula 17a wherein A=N, G=N, and W=O) can be prepared from hydrazides of Formula 19 as illustrated in Scheme 12. When R$^{27}$═C(═S)S(C$_1$–C$_4$ alkyl), the diacyl compound of Formula 19 is treated with excess thionyl halide, for example excess thionyl chloride. The product formed first is the ring-closed compound of Formula 20 which can be isolated or converted in situ to the compound of Formula 17c; see P. Molina, A. Tárraga, A. Espinosa, *Synthesis*, (1989), 923 for a description of this process.

Alternatively, when R$^{27}$=R$^2$ as defined above, the hydrazide of Formula 19 is cyclized with phosgene to form the cyclic urea of Formula 17c wherein hal=Cl. This procedure is described in detail in *J. Org. Chem.*, (1989), 54, 1048.

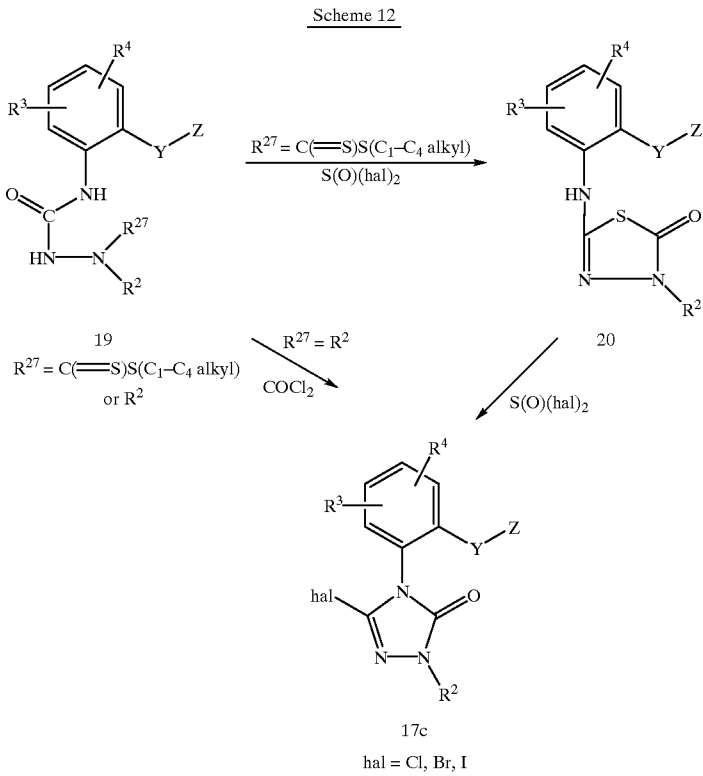

The hydrazides of Formula 19 can be prepared as illustrated in Scheme 13. Condensation of the isocyanate of Formula 21 with the hydrazine of Formula $H_2NNR^2R^{27}$ in an inert solvent such as tetrahydrofuran affords the hydrazide.

Conversion of 22b to 22c can be accomplished by reaction with trialkyl tetrafluoroborates.

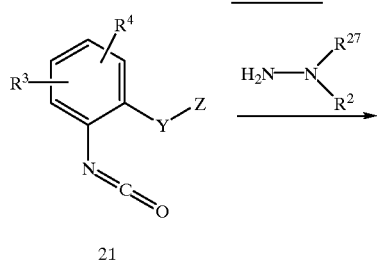

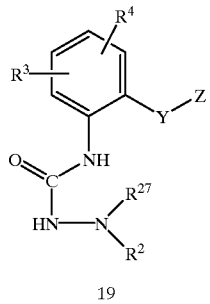

3) Conjugate Addition/Cyclization Procedures

In addition to the methods disclosed above, compounds of Formula I wherein $X=SR^1$ and $G=C$ (Formula Ic) can be prepared by treating a ketene dithioacetal of Formula 22 with an ambident nucleophile of Formula 6 (Scheme 14). The nucleophiles of Formula 6 are described above.

Scheme 14

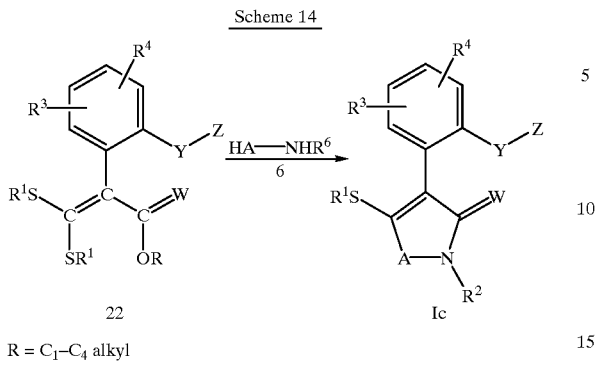

R = $C_1$–$C_4$ alkyl

Ketene dithioacetals of Formula 22a or 22b can be prepared by condensing phenylacetic acid esters of Formula 9 or amides of Formula 9a, respectively, with carbon disulfide in the presence of a suitable base, followed by reaction with two equivalents of an $R^1$-halide, such as iodomethane or propargyl bromide (Scheme 15). Conversion of 22b to 22c can be accomplished by reaction with trialkyl tetrafluoroborates.

Scheme 15

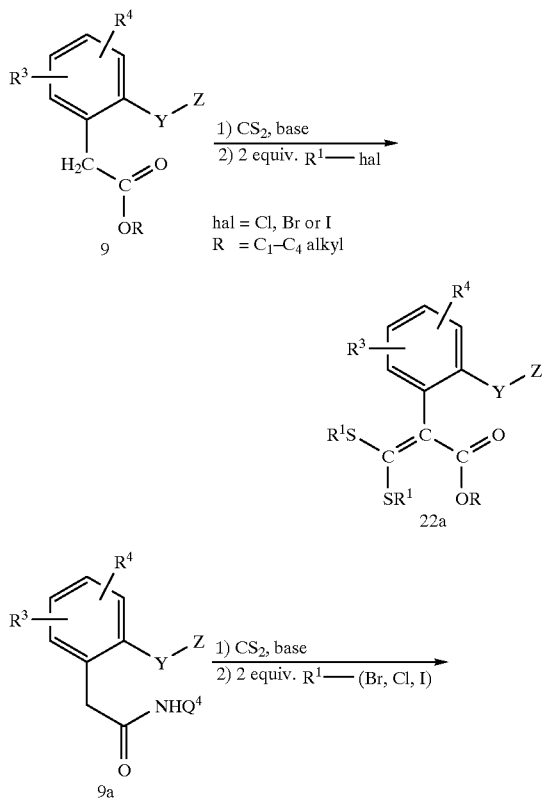

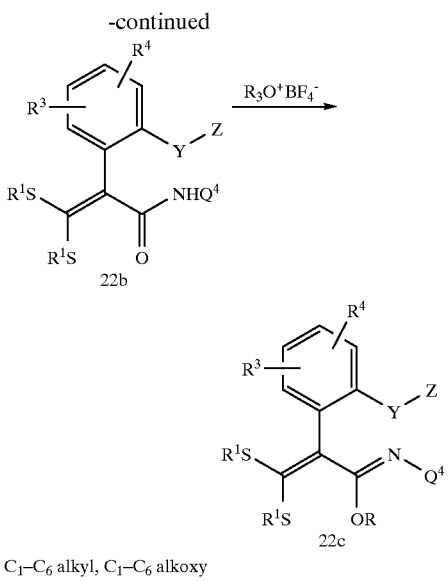

$Q^4$ = H, $C_1$–$C_6$ alkyl, $C_1$–$C_6$ alkoxy

Compounds of Formula 1d (compounds of Formula 1 wherein A=N, G=N) can be prepared by condensation of N-amino-ureas of Formula 23 with a carbonylating agent of Formula 24 (Scheme 16). The carbonylating agents of Formula 24 are carbonyl or thiocarbonyl transfer reagents such as phosgene, thiophosgene, diphosgene (ClC(=O)OCCl$_3$), triphosgene (Cl$_3$COC(=O)OCCl$_3$), N,N'-carbonyldiimidazole, N,N'-thiocarbonyldiimidazole, and 1,1'-carbonyldi(1,2,4-triazole). Alternatively, the compounds of Formula 24 can be alkyl chloroformates or dialkyl carbonates. Some of these carbonylating reactions may require the addition of a base to effect reaction. Appropriate bases include alkali metal alkoxides such as potassium tert-butoxide, inorganic bases such as sodium hydride and potassium carbonate, tertiary amines such as triethylamine and triethylenediamine, pyridine, or 1,8-diazabicyclo[5.4.0]undec-7-ene (DBU). Suitable solvents include polar aprotic solvents such as acetonitrile, dimethylformamide, or dimethyl sulfoxide; ethers such as tetrahydrofuran, dimethoxyethane, or diethyl ether; ketones such as acetone or 2-butanone; hydrocarbons such as toluene or benzene; or halocarbons such as dichloromethane or chloroform. The reaction temperature can vary between 0° C. and 150° C. and the reaction time can be from 1 to 72 hours depending on the choice of base, solvent, temperature, and substrates.

Scheme 16

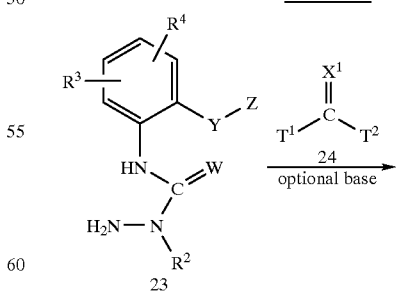

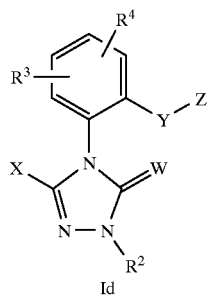

$T^1$ and $T^2$ are independently Cl, $OCCl_3$, $O(C_1-C_4$ alkyl),
1-imidazolyl, 1, 2, 4-triazolyl X = OH or SH $X^1$ = O or S N-Amino-ureas of Formula 23 can be prepared as illustrated in Scheme 17. Treatment of an aniline of Formula 25 with phosgene, thiophosgene, N,N'-carbonyldiimidazole, or N,N'-thiocarbonyldiimidazole produces the isocyanate or isothiocyanate of Formula 26. A base can be added for reactions with phosgene or thiophosgene. Subsequent treatment of the iso(thio)cyanate with an $R^2$-substituted hydrazine produces the N-amino-urea of Formula 23.

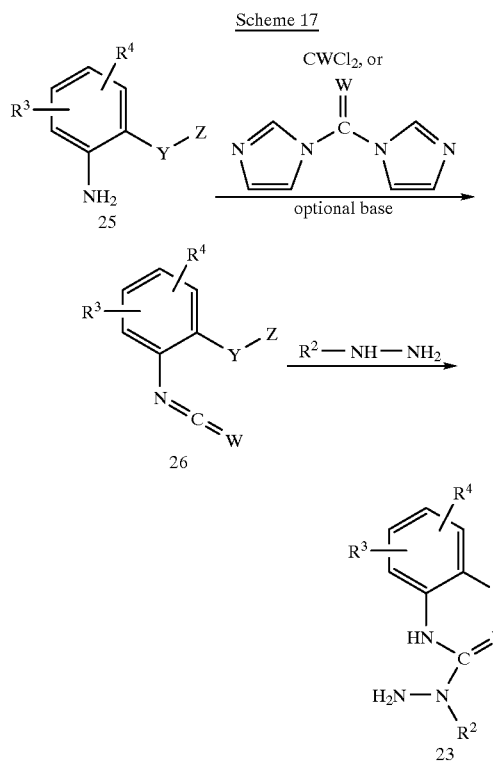

Compounds of Formula 1e (compounds of Formula 1 wherein $A=CR^5$, G=N, and X=O) can be prepared by either method illustrated in Scheme 18. Ureas of Formula 27 are reacted with activated 2-halocarboxylic acid derivatives such as 2-halocarboxylic acid chlorides, 2-halocarboxylic acid esters or 2-haloacyl imidazoles. The initial acylation on the aniline nitrogen is followed by an intramolecular displacement of the 2-halo group to effect cyclization. Base may be added to accelerate the acylation and/or the subsequent cyclization. Suitable bases include triethylamine and sodium hydride. As described above, base may be added to accelerate the reaction and subsequent cyclization to Formula 1b compounds. Carbodiimides 26a can be prepared as shown in Scheme 18, starting with compounds of Formula 26. Alternatively, Formula 1e compounds can be prepared by reaction of Formula 26 isocyanates with Formula 28a esters. As described above, base may be added to accelerate the reaction and subsequent cyclization to Formula 1e compounds. Alternatively, Formula 1b compounds can be prepared by reaction of Formula 26 iso(thio)cyanates or Formula 26a carbodiimides with Formula 28a esters.

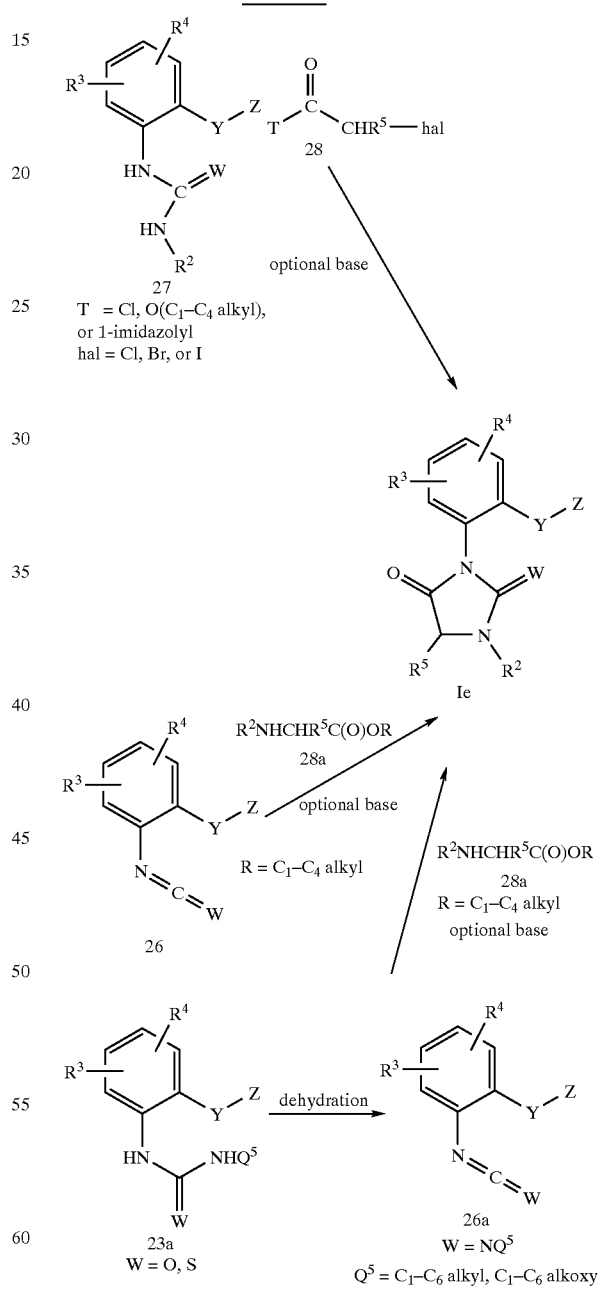

The ureas or amidines of Formula 27 can be prepared by either of the methods illustrated in Scheme 19. The anilines of Formula 25 can be contacted with an isocyanate or isothiocyanate of Formula $R^2N=C=W$ as described above.

Alternatively, an isocyanate or isothiocyanate of Formula 26 or carbodiimide of Formula 26 can be condensed with an amine of Formula $R^2$—$NH_2$ to form the urea or amidine. The anilines and iso(thio)cyanates of Formulae 25 and 26, respectively, are commercially available or prepared by well-known methods. For example, isothiocyanates can be prepared by methods described in *J. Heterocycl. Chem.*, (1990), 27, 407. Isocyanates can be prepared as described in March, J. *Advanced Organic Chemistry;* 3rd ed., John Wiley: New York, (1985), pp 944, 1166.

Scheme 19

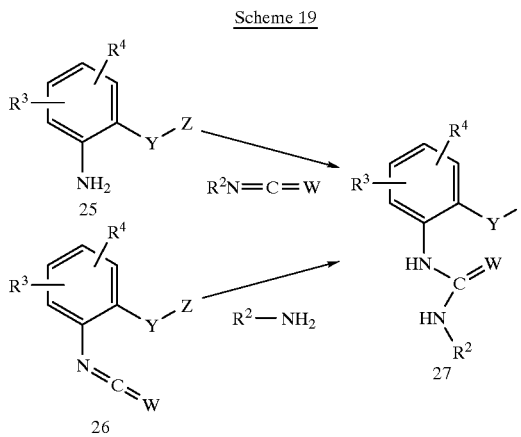

4) Thionation Procedures

Compounds of Formula 1e, compounds of Formula I wherein W=S, can be prepared by treating compounds of Formula Id (I wherein W=O) with thionating reagents such as $P_2S_5$ or Lawesson's reagent (2,4-bis(4-methoxyphenyl)-1,3-dithia-2,4-diphosphetane-2,4-disulfide) as illustrated in Scheme 20 (see *Bull. Soc. Chim. Belg.,* (1978), 87, 229; and *Tetrahedron Lett.,* (1983), 24, 3815).

Scheme 20

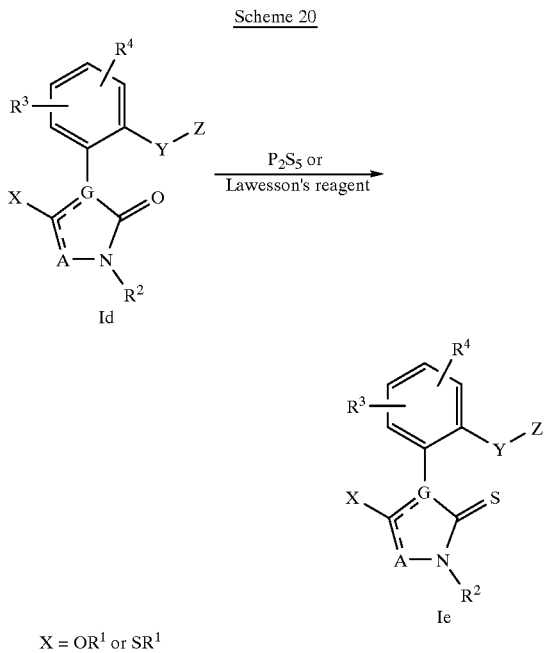

$X = OR^1$ or $SR^1$

Reaction of compounds of Formula Iea with an alkyl halide in the presence of base provides compounds of Formula Ieb, which can be reacted with compounds of Formula $Q^5NH_2$ and then alkylated with $R^2$—(Br, Cl, or I) to provide compounds of Formula Iec.

Scheme 20a

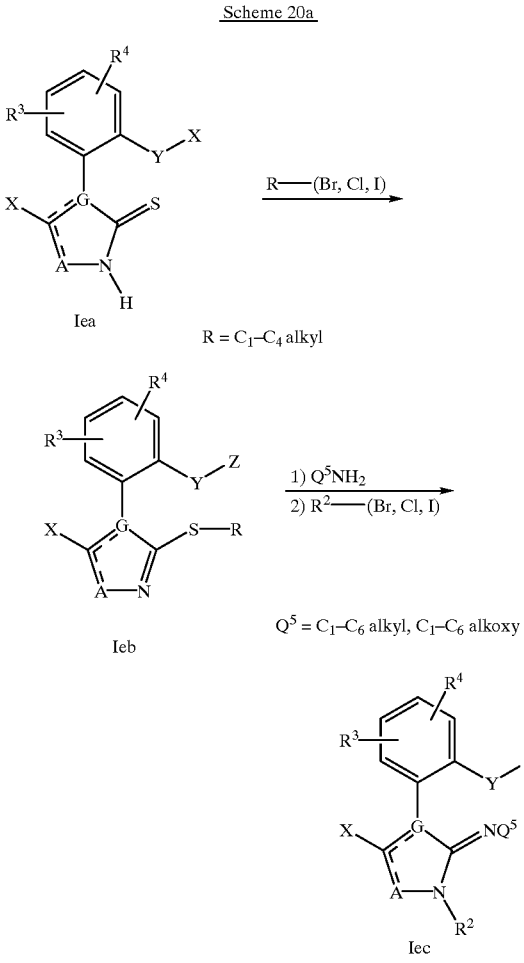

5) Aryl Moiety Synthesis Procedures

Compounds of Formula If (compounds of Formula I wherein Y is $CHR^6O$, $CHR^6S$, or $CHR^6O$—N=$CR^7$) can be prepared by contacting benzyl halides of Formula 29 with various nucleophiles (Scheme 21). The appropriate alcohol or thiol is treated with a base, for example sodium hydride, to form the corresponding alkoxide or thioalkoxide which acts as the nucleophile.

Scheme 21

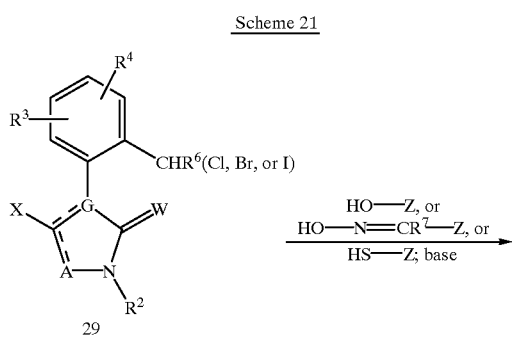

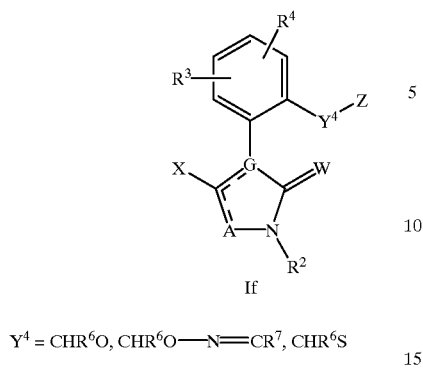

$Y^4 = CHR^6O, CHR^6O—N=CR^7, CHR^6S$

Benzyl halides of Formula 29 can be prepared by radical halogenation of the corresponding alkyl compound (i.e., H instead of halogen in Formula 29), or by acidic cleavage of the corresponding methyl ether (i.e., OMe instead of halogen in Formula 29).

Compounds of Formula I wherein Y is $CR^6=CR^6$ and $CHR^6—CHR^6$ (Formula Ig and Ih, respectively) can be prepared as illustrated in Scheme 22. Treatment of the benzyl halides of Formula 29 with triphenylphosphine or a trialkylphosphite produces the corresponding phosphonium salt (Formula 30) or phosphonate (Formula 31), respectively. Condensation of the phosphorus compound with a base and a carbonyl compound of Formula $Z(R^6)C=O$ affords the olefin of Formula Ig.

Scheme 22

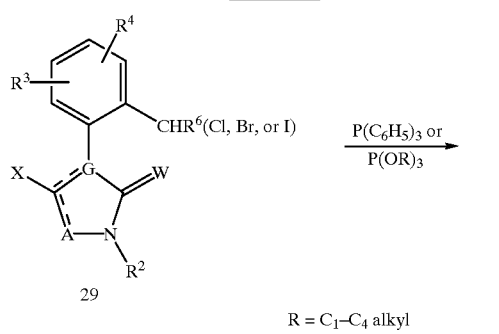

$R = C_1–C_4$ alkyl

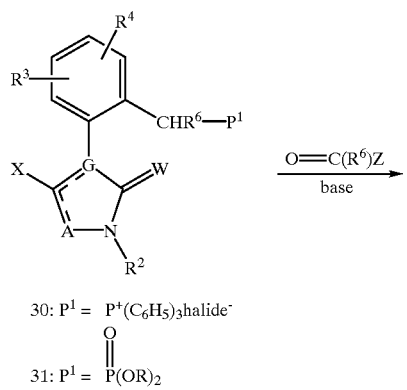

30: $P^1 = P^+(C_6H_5)_3$halide⁻

31: $P^1 = \overset{O}{\underset{\|}{P}}(OR)_2$

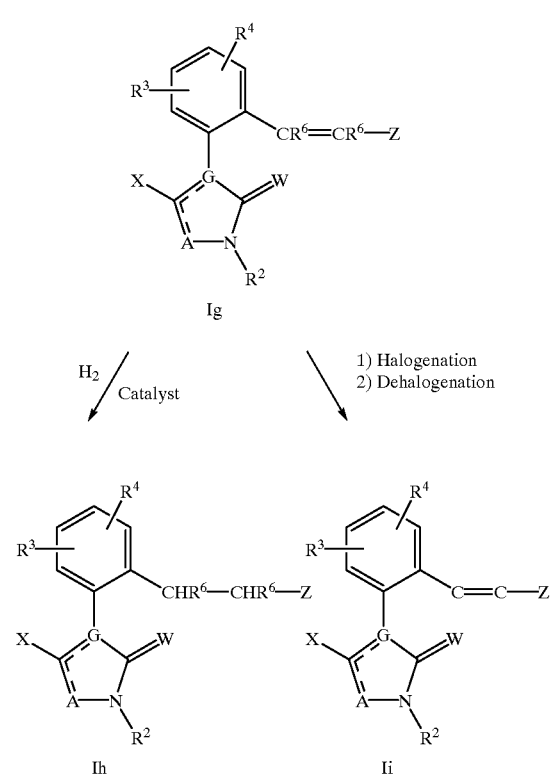

The olefins of Formula Ig can be converted to the saturated compounds of Formula Ih by hydrogenation over a metal catalyst such as palladium on carbon as is well-known in the art (Rylander, *Catalytic Hydrogenation in Organic Synthesis;* Academic: New York, 1979).

Formula Ii alkynes can be prepared by halogenationl/dehalogenation of Formula Ig olefins using procedures well-known in the art (March, J. *Advanced Organic Chemistry;* 3rd ed., John Wiley: New York, (1985), p 924). Additionally, Formula Ii alkynes can be prepared by well-known reaction of aromatic halides with alkyne derivatives in the presence of catalysts such as nickel or palladium (see *J. Organomet. Chem.*, (1975), 93 253–257).

The olefin of Formula Ig can also be prepared by reversing the reactivity of the reactants in the Wittig or Horner-Emmons condensation. For example, 2-alkylphenyl derivatives of Formula 31 can be converted into the corresponding dibromo-compound of Formula 33 as illustrated in Scheme 23 (see *Synthesis,* (1988), 330). The dibromo-compound can be hydrolyzed to the carbonyl compound of Formula 34, which in turn can be condensed with a phosphorus-containing nucleophile of Formula 35 or 36 to afford the olefin of Formula Ig.

Scheme 23

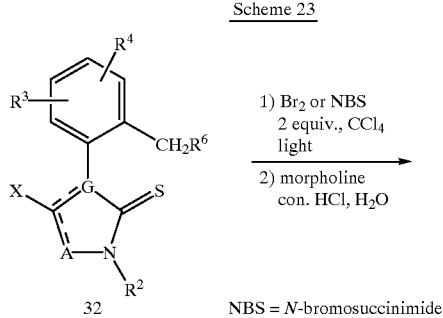

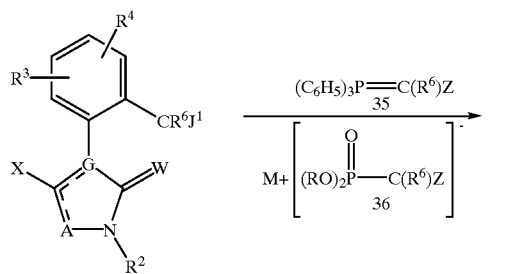

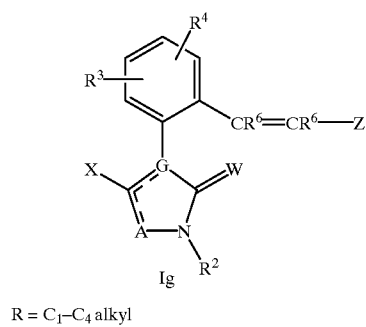

R = $C_1$–$C_4$ alkyl

Oximes of Formula Ij (Formula I wherein Y is C($R^7$)=N—O) can be prepared from carbonyl compounds of Formula 37 by condensation with hydroxylamine, followed by O-alkylation with electrophiles of Formula Z-(Cl, Br, or I) (Scheme 24). Alternatively, the O-substituted hydroxylamine can be condensed with the carbonyl compound of Formula 37 to yield oximes of Formula Ij directly.

Scheme 24

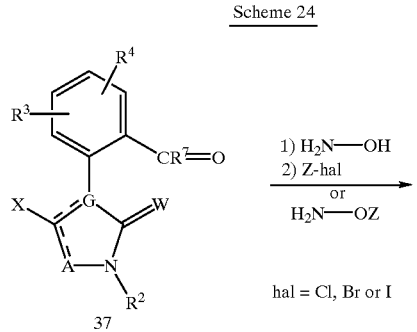

-continued

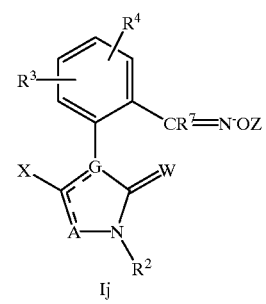

Carbamates of Formula Ik can be prepared by reacting benzyl alcohols of Formula 38 with isocyanates of Formula 39 (Scheme 25). A base such as triethylamine can be added to catalyze the reaction. As shown, carbamates of Formula Ik can be further alkylated to provide the carbamates of Formula Il.

Conversion of compounds of Formula Im to compounds of Formula In is summarized in Scheme 25. Reaction of the secondary amides with silylating agents, such as trimethylsilyl chloride in the presence of base or hexamethyldisilazane in the presence of acid, provides the silylated intermediate which is oxidized in situ with the peroxo-molybdenum compound $MoO_5$•HMPA complexed with pyridine or dimethylformamide. Subsequent hydrolysis with aqueous EDTA (ethylenediaminetetraacetic acid) liberates the hydroxylated amides (see S. A. Martin, P. G. Sammes and R. M. Upton, *J. Chem. Soc., Perkin Trans.* 1, (1979), 2481 and J. H. Rigby and M. Qabar, *J. Org. Chem.,* (1989), 54, 5852). Optional alkylation with $C_1$–$C_2$ alkyl halides in the presence of base or acylation with acetic anhydride can be performed on the hydroxyl amides In where $R^{2'}$=OH.

Scheme 25

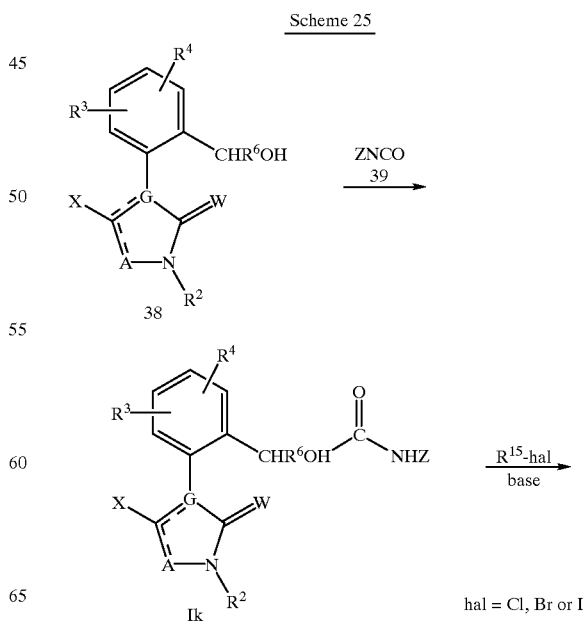

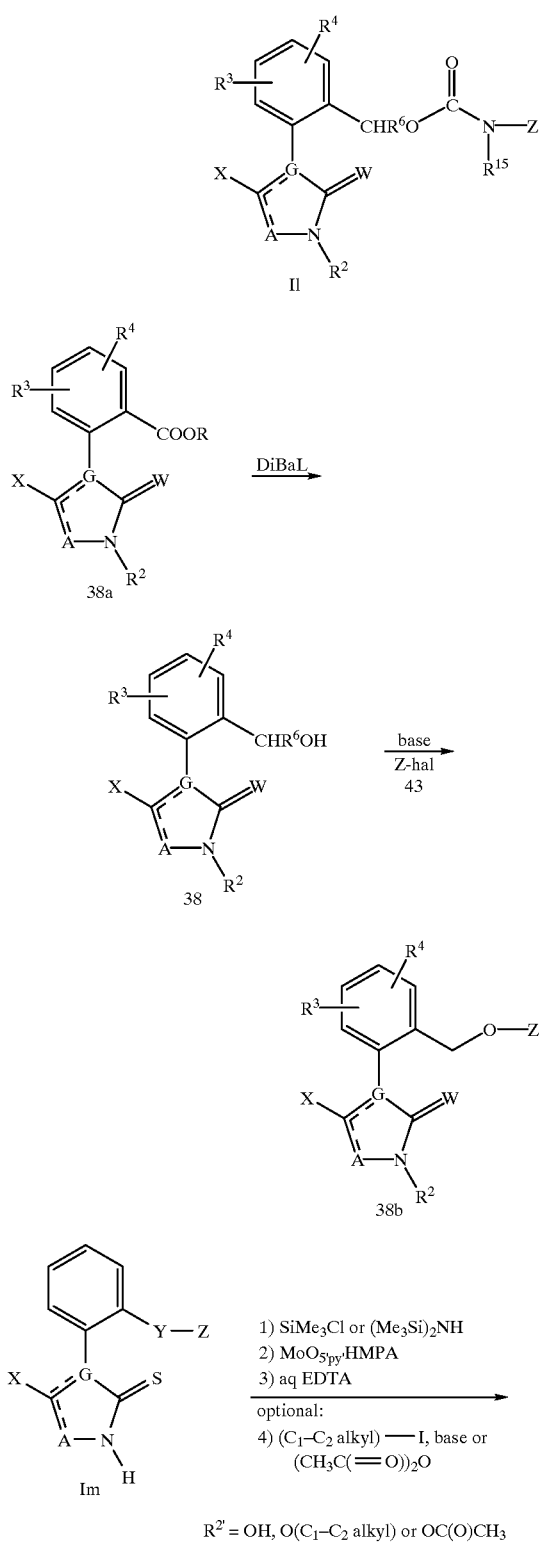

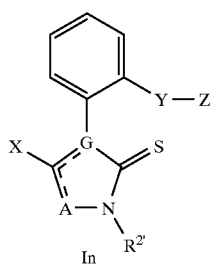

Compounds of Formula 38, where $R^6$=H, can be formed from compounds of Formula 38a by reduction with, for example, diisobutylaluminum hydride (DiBAL). Compounds of Formula 38b can also be formed from compounds of Formula 38, where $R^6$=H, by coupling with compounds of Formula 43 in the presence of base.

The compounds of the present invention are prepared by combinations of reactions as illustrated in the Schemes 1–25 in which Z is a moiety as described in the summary. Preparation of the compounds containing the radical Z as described in the summary, substituted with L (defined as any group attached to Z as depicted in each of the individual schemes) can be accomplished by one skilled in the art by the appropriate combination of reagents and reaction sequences for a particular Z-L. Such reaction sequences can be developed based on known reactions available in the chemical art. For a general reference, see March, J. *Advanced Organic Chemistry;* 3rd ed., John Wiley: New York, (1985) and references therein. See the following paragraphs for some examples of how L is defined in individual schemes, and the preparation of representative Z-L examples.

Compounds of Formula 41 in Scheme 26 can be prepared from compounds of Formula 40 by reaction with hydroxylamine or hydroxylamine salts. See Sandler and Karo, "Organic Functional Group Preparations," Vol. 3 Academic Press, New York, (1972) 372–381 for a review of methods. Compounds of Formula 41 correspond to compounds of Formula 13 in Scheme 6 when $Y^1$=O—N=C($R^7$) and in Scheme 21, reagent HO—N=C$R^7$.

Scheme 26

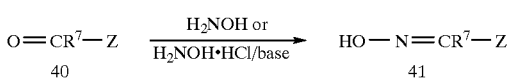

Compounds of Formula 40 can be prepared from compounds of Formula 39a (Scheme 27) by Friedel-Crafts acylation with compounds of Formula 42. (See Olah, G. "Friedel-Crafts and Related Reactions," Interscience, New York (1963–1964) for a general review). Compounds of Formula 40 may also be prepared by reaction of acyl halides, anhydrides, esters, or amides of Formula 45 with organometallic reagents of Formula 44. (See March, J. *Advanced Organic Chemistry;* 3rd ed., John Wiley: New York, (1985), pp 433–435 and references therein.) The organometallic compounds of Formula 44 may be prepared by reductive metallation or halogen-metal exchange of a halogen-containing compound of Formula 43 using, for example, magnesium or an organolithium reagent, or by deprotonation of compounds of Formula 39a using a strong base such as a lithioamide or an organolithium reagent, followed by transmetallation. Compound 40 corresponds to Compound 14a in Scheme 8, while compound 40a corresponds to O=C($R^6$)Z in Scheme 22.

Scheme 27

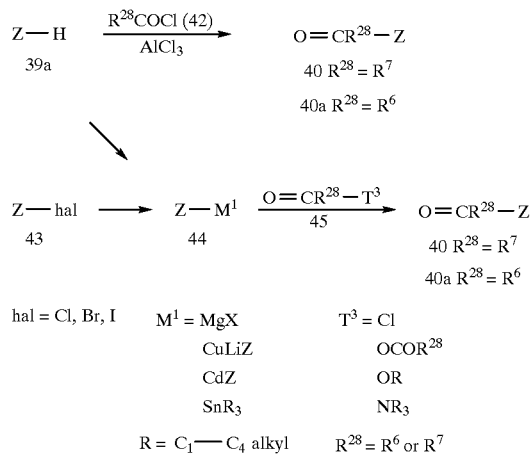

Compounds of Formula 43 may be prepared by reaction of compounds of Formula 39a (Scheme 28) with, for example, bromine or chlorine, with or without additional catalysts, under free-radical or aromatic electrophilic halogenation conditions, depending on the nature of Z. Alternative sources of halogen, such as N-halosuccinimides, tert-butyl hypohalites or $SO_2Cl_2$, may also be used. (See March, J. *Advanced Organic Chemistry;* 3rd ed., John Wiley: New York, (1985), pp 476–479, 620–626, and references therein.) For a review of free-radical halogenation, see Huyser, in Patai," The Chemistry of the Carbon-Halogen Bond," Part 1, Wiley, N.Y. (1973) pp 549–607. For electrophilic substitutions, see de la Mare, "Electrophilic Halogenation," Cambridge University Press, London (1976). Compounds of Formula 43 correspond to compounds of Formula 15 in Scheme 7 where Lg=Br, Cl, or I and reagent Z-hal in Scheme 24. Compounds of Formula 47 can be prepared from compounds of Formula 46 by similar procedures. Compounds of Formula 47 correspond to compounds of Formula 16 in Scheme 7 where Lg=Br, Cl, or I. Compounds of Formula 35 or 36 in Scheme 23 can be prepared by reaction of compounds of Formula 47 with triphenylphosphine or trialkyl phosphites, respectively, followed by deprotonation with base. See Cadogen, "Organophosphorus Reagents in Organic Synthesis," Academic Press, New York (1979) for a general treatise on these reagents.

Scheme 28

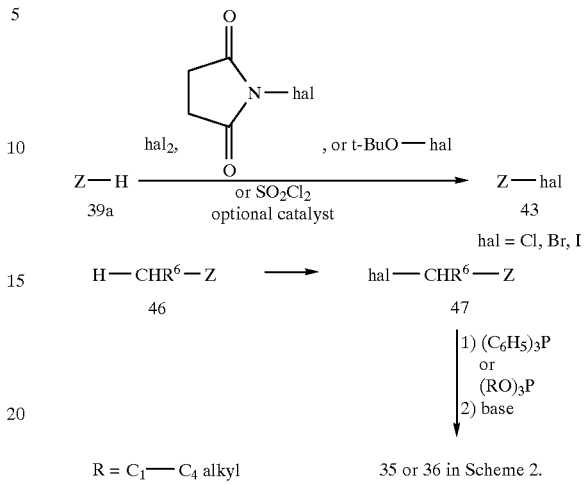

Compounds of Formula 48 can be prepared from compounds of Formula 40b by treatment with peracids such as perbenzoic or peracetic acid, or with other peroxy compounds in the presence of an acid catalysts, followed by hydrolysis of the resultant ester. For a review, see Plesnicar, in Trahanovsky, "Oxidation in Organic Chemistry, pt. C", Academic Press, New York (1978) pp 254–267. Formula 48 corresponds to Formula 13 in Scheme 6 when $Y^1$=O and reagent HO-Z in Scheme 21. Compounds of Formula 52 can be prepared from compounds of Formula 48 by conversion to the dialkylthiocarbamates of Formula 50 followed by rearrangement to Formula 51 and subsequent hydrolysis. See M. S. Newman and H. A. Karnes, *J. Org. Chem.* (1966), 31, 3980–4. Formula 52 corresponds to Formula 13 in Scheme 6 when $Y^1$=S and reagent HS-Z in Scheme 21.

Scheme 29

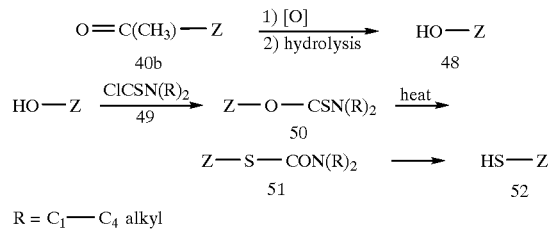

Compounds of Formula 53 can be converted to compounds of Formulae 43, 48 or 52 via the diazonium compounds 54, by treatment with nitrous acid followed by subsequent reaction (Scheme 30). See reviews by Hegarty, pt. 2, pp 511–91 and Schank, pt. 2, pp 645–657, in Patai, "The Chemistry of Diazonium and Diazo Groups," Wiley, N.Y. (1978). Treatment of Formula 54 compounds with cuprous halides or iodide ions yield compounds of Formula 43. Treatment of Formula 54 compounds with cuprous oxide in the presence of excess cupric nitrate provides compounds of Formula 48. (Cohen, Dietz, and Miser, *J. Org. Chem,* (1977), 42, 2053). Treatment of Formula 54 compounds with $(S_2)^{-2}$ yields compounds of Formula 52.

Scheme 30

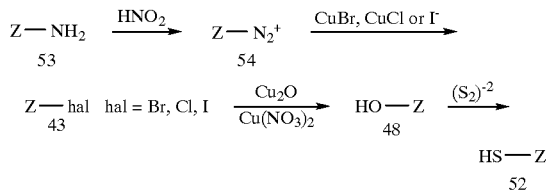

Compounds of Formula 53 can be prepared from compounds of Formula 39a by nitration, followed by reduction (Scheme 31). A wide variety of nitrating agents is available (see Schofield, "Aromatic Nitration," Cambridge University Press, Cambridge (1980)). Reduction of nitro compounds can be accomplished in a number of ways (see March, J. *Advanced Organic Chemistry;* 3rd ed., John Wiley: New York, (1985), pp 1103–4 and references therein). Formula 53 corresponds to Formula 13 in Scheme 6 when $Y^1=NR^6$ and $R^6=H$.

Scheme 31

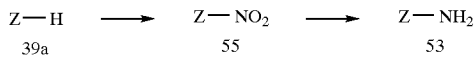

Compounds of Formula 40b can be prepared from compounds of Formula 48 by forming the triflate, followed by palladium-catalyzed arylation of butyl vinyl ether, and treatment with acid to form the corresponding aryl methyl ketones. (Cabri, W., Ilaria, C., Bedeschi, A., *J. Org. Chem.,* (1990), 55, 3654).

Scheme 32

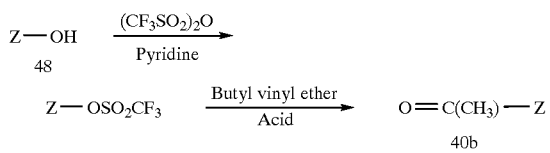

Compounds of Formula 40b can be prepared from compounds of Formula 40c by forming the cyano-carbonate. Further conversion to the ketone is performed by alkylating with sodium hydride, followed by deprotection with dilute base. (Au, A. T., *Synthetic Communications,* (1984), 14, 743).

Scheme 33

-continued

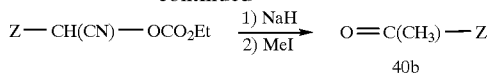

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: N.Y. 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in Schemes 1–33 in an order other than that implied by the particular sequence presented to prepare the compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s=singlet, d=doublet, t=triplet, q=quartet, m=multiplet, dd=doublet of doublets, br s=broad singlet, AB q="AB" quartet.

EXAMPLE 1

Step A: Preparation of methyl (2-bromomethyl) benzeneacetate

Methyl o-tolylacetate (24 g), N-bromosuccinimide (27.2 g) and benzoyl peroxide (about 50 mg) were mixed in 200 mL of carbon tetrachloride and heated to reflux with a high-intensity light source for 1.5 h. After cooling, the precipitate was removed by filtration and the filtrate concentrated in vacuo to yield 36 g (about 100% yield) of the title compound of Step A as an amber oil. $^1$H NMR (CDCl$_3$): δ 7.34 (m,1H), 7.26 (m,2H), 7.16 (m,1H), 4.57 (s,2H), 3.80 (s,2H), 3.69 (s,3H).

Step B: Preparation of methyl 2-[[(benzoylamino)oxy] methyl]benzeneacetate

Benzohydroxamic acid (17 g) and potassium carbonate (18.7 g) were suspended in 200 mL of acetonitrile and the mixture was stirred at 60° C. for 30 minutes. A solution of 28 g of the title compound of Step A in 100 mL of acetonitrile was added dropwise over 0.5 h. The mixture was stirred at 60° C. for 3 h and then cooled to room temperature overnight. Heating was resumed for an additional 4 h. The mixture was cooled and filtered. The filtrate was concentrated in vacuo. The residue was taken up in 200 mL of ethyl acetate and washed with 100 mL of 6% aqueous potassium carbonate solution. The aqueous wash was extracted with 100 mL of ethyl acetate. The combined organic phases were washed with 100 mL of water. The organic phase was dried (MgSO$_4$), filtered and concentrated in vacuo to yield 31.5 g (93% yield) of the title compound of Step B as an orange oil. $^1$H NMR (CDCl$_3$): δ 9.09 (br s,1H), 7.60 (m,2H), 7.47 (m,1H), 7.37 (m,3H), 7.29 (m,3H), 5.14 (s,2H), 3.88 (s,2H), 3.71 (s,3H).

Step C: Preparation of methyl 2-[(aminooxy)methyl] benzeneacetate hydrochloride

To a solution of HCl in methanol (prepared by adding 20 mL of acetyl chloride slowly to 200 mL of methanol) was added the title compound of Step B (31.5 g). The mixture was heated to 60° C. for 1.5 h. The solvent was removed in vacuo. The residue was taken up in 100 mL of diethyl ether and stirred at room temperature for 30 minutes. The ether was decanted off and the solid was taken up in 100 mL of tetrahydrofuran and heated to about 50° C. The mixture was then cooled in an ice water bath and the solid was collected by filtration to provide 11.5 g (47% yield) of the title compound of Step C as a white solid melting at 169–170° C.

Step D: Preparation of methyl 2-[[[[1-(2-naphthalenyl) ethylidene]amino]oxy]methyl]benzeneacetate 2'-acetonaphthone (1.02 g) and the title compound of Step C (1.39 g) were dissolved in 40 mL of pyridine. The solution was heated to 90° C. for 3 h, and then was cooled to room temperature overnight. The pyridine was removed in vacuo and the residue was taken up in 40 mL of 1N HCl solution and extracted with ethyl acetate (3×50 mL) The combined organic layers were dried (MgSO$_4$), filtered and concentrated in vacuo to yield 2.2 g (about 100% yield) of the title compound of Step D as an amber oil. $^1$H NMR (CDCl$_3$): δ 7.99 (d,1H), 7.86 (m,4H), 7.48 (m,3H), 7.31 (m,3H), 5.33 (s,2H), 3.85 (s,2H), 3.68 (s,3H), 2.34 (s,3H).

Step E: Preparation of dimethyl [2-[[[[1-(2-naphthalenyl) ethylidene]amino]oxy]methyl]phenyl]propanedioate The title compound of Step D (2.1 g) was dissolved in 10 mL of dimethyl carbonate. A slurry of 480 mg of sodium hydride (60% oil dispersion) in 10 mL of tetrahydrofuran was added and the mixture was heated to reflux for 2 h. The mixture was cooled, quenched with 15 mL of 1N HCl solution and extracted with ethyl acetate (3×25 mL). The combined organic layers were dried (MgSO$_4$), filtered and concentrated in vacuo to yield 2.6 g of crude product, the title compound of Step E, as an amber oil. $^1$H NMR (CDCl$_3$): δ 7.99 (br s,1H), 7.85 (m,4H), 7.3–7.6 (m,6H), 5.33 (s,2H), 5.27 (s,1H), 3.73 (s,6H), 2.31 (s,3H).

Step F: Preparation of 5-methoxy-2-methyl-4-[2-[[[[1-(2-naphthalenyl)ethylidene]amino]oxy]methyl]phenyl]-3(2H)-isoxazole N-methylhydroxylamine hydrochloride (1.5 g) was dissolved in 25 mL of methanol. A solution of 2.02 g of potassium hydroxide dissolved in 25 mL of methanol was added with ice bath cooling. After 15 minutes, the precipitated potassium chloride was removed by filtration. To the filtrate was added a solution of 2.4 g of the title compound of Step E in 10 mL of methanol. The resulting mixture was stirred at room temperature overnight. The mixture was diluted with water, acidified with HCl and extracted with methylene chloride (3×30 mL). The combined organic layers were dried (MgSO$_4$), filtered and concentrated in vacuo to yield 2.35 g of amber oil which was dissolved in 30 mL of toluene and 3 mL of methanol. A 10% solution of trimethylsilyldiazomethane in hexane (4 mL) was added dropwise and the solution was stirred at room temperature for 4 h. The solvents were removed in vacuo and the residue was purified by flash chromatography (1:1 hexane:ethyl acetate as eluant). The second eluting component was collected to yield 670 mg (28% yield) of the title compound of Step F, a compound of the invention, as an amber oil. $^1$H NMR (CDCl$_3$): δ 7.97 (d,1H), 7.83 (m,4H), 7.56 (t,1H), 7.47 (m,2H), 7.35 (m,3H), 5.33 (s,2H), 3.93 (s,3H), 3.43 (s,3H), 2.34 (s,3H).

EXAMPLE 2

Step A: Preparation of 2,2-dimethyl-N-(2-methylphenyl) hydrazinecarboxamide o-Tolyl isocyanate (10.0 g) was dissolved in 75 mL of toluene under nitrogen. The solution was cooled to 5° C. and to this was slowly added a solution of 1,1-dimethylhydrazine (5.7 mL) in toluene. After addition, the ice-bath was removed and the resulting slurry was allowed to stir an additional 10 minutes. The solid was filtered off and rinsed successively with hexane, a small amount of 20% diethyl ether/hexane, and then hexanes again. This afforded 11.1 g (77%) of the title compound of Step A. $^1$H NMR (CDCl$_3$): δ 8.1 (br s,1H), 7.94 (d,1H), 7.21–7.15 (m,3H), 6.99 (t,1H), 5.23 (br s,1H), 2.63 (s,6H), 2.27 (s,3H).

Step B: Preparation of 5-chloro-2,4-dihydro-2-methyl-4-(2-methylphenyl)-3H-1,2,4-triazol-3-one To a solution of 11.1 g of the title compound of Step A dissolved in 600 mL of methylene chloride under nitrogen was added 17.1 g of triphosgene. The solution was heated at reflux overnight, cooled, and then concentrated under reduced pressure. The resulting residue was dissolved in ethyl acetate, washed with water and then washed with saturated aqueous NaCl. The organic phase was dried (MgSO$_4$), filtered, and concentrated under reduced pressure. The residue was purified by flash chromatography (30–50% ethyl acetate/hexanes as eluent) to afford 8.25 g (64% yield) of the title compound of Step B. $^1$H NMR (CDCl$_3$): δ 7.42–7.30 (m,3H), 7.17 (d,1H), 3.54 (s,3H), 2.22 (s,3H).

Step C: Preparation of 2,4-dihydro-5-methoxy-2-methyl-4-(2-methylphenyl)-3H-1,2,4-triazol-3-one 8.25 g of the title compound of Step B was dissolved in 80 mL of 1:1 dimethoxyethane/methanol under N$_2$. 14.0 mL of sodium methoxide (30% solution in methanol) was added and the solution was heated at reflux for 3 h. The mixture was allowed to cool, diluted with ethyl acetate, washed with water, and then washed with saturated aqueous NaCl. The combined organic extracts were dried (MgSO$_4$), filtered, and concentrated under reduced pressure. The residue was purified by flash chromatography (50–70% ethyl acetate/hexanes as eluent) and triturated with 50% diethyl ether/hexanes to afford 6.7 g of the title compound of Step C (95% pure). $^1$H NMR (CDCl$_3$): δ 7.35–7.27 (m,3H), 7.18 (d,1H), 3.94 (s,3H), 3.46 (s,3H), 2.22 (s,3H).

Step D: Preparation of 4-[2-(bromomethyl)phenyl]-2,4-dihydro-5-methoxy-2-methyl-3H-1,2,4-triazol-3-one To a solution/suspension of 6.7 g of the title compound of Step C dissolved in 95 mL of carbon tetrachloride under N$_2$ was added N-bromosuccinimide (6.53 g) followed by a catalytic amount of benzoyl peroxide. The solution was heated at reflux for 2 h. Another 1.63 g of N-bromosuccinimide and a catalytic amount of benzoyl peroxide were added and the solution was heated at reflux for an hour. After cooling, methylene chloride was added and the organic layer was washed successively with water, 0.1 N sodium thiosulfate solution, and then saturated aqueous NaCl. The combined organic extracts were dried (MgSO$_4$), filtered, and concentrated under reduced pressure. The residue was purified by flash chromatography (3–10% diethyl ether/methylene chloride as eluent) to afford 3.12 g of the title compound of Step D. $^1$H NMR (CDCl$_3$): δ 7.5 (m,1H), 7.44 (m,2H), 7.22 (m,1H), 4.60 (d,1H), 4.36 (d,1H), 3.96 (s,3H), 3.47 (s,3H).

Step E: Preparation of 2,4-dihydro-5-methoxy-2-methyl-4-[2-[[[[1-(2-naphthalenyl)ethylidene]amino]oxy]methyl]phenyl]-3H-1,2,4-triazol-3-one To a solution of 0.56 g (3.02 mmol) of 1-(2-naphthalenyl)ethanone oxime in 10 mL of DMF was added 0.13 g (3.28 mmol) of NaH. 0.75 (2.52 mmol) of the title compound of Step D was then added to the reaction and the mixture was stirred at room temperature for 3 h. The reaction mixture was washed successively with water and saturated NaCl and then extracted with ethyl acetate. The combined organic extracts were dried over magnesium sulfate, filtered, and concentrated. The crude product was purified by flash chromatography on silica gel using 60% ethyl acetate/hexane as eluent to give 0.80 g (79% yield) of the title compound of Step E, a compound of the invention, as a solid melting at 91–94° C.

EXAMPLE 3

Step A: Preparation of N-[2-(bromomethyl)phenyl]-2,2-dimethylhydrazinecarboxamide A solution of o-tolyl isocyanate (50.4 g) and 75.2 g of N-bromosuccinimide in 800 mL of carbon tetrachloride was heated to reflux. Benzoyl peroxide (1.1 g) was added and the mixture was heated to reflux for 1.5 hours. The solution was cooled to room temperature and the precipitate was removed by filtration. The filtrate was concentrated in vacuo and redissolved in 500 mL of toluene and cooled to 5° C. 1,1-Dimethyl hydrazine (30 mL) in 20 mL of toluene was added dropwise. The reaction mixture was stirred at room temperature overnight. The precipitated solid was collected by filtration and redissolved in 1 L of dichloromethane. The organic solution was washed with 500 mL of water and then with 500 mL of saturated aqueous sodium chloride solution. The organic phase was dried (MgSO$_4$), filtered and concentrated to give 58 g (56% yield) of the title compound of Step A as a beige solid. $^1$NMR (CDCl$_3$): δ 8.6 (br s,1H), 8.00 (d,1H), 7.30 (m,2H), 7.04 (t,1H), 5.70 (br s,1H), 4.52 (s,2H), 2.67 (s,6H). The material was used in the next step without further characterization.

Step B: Preparation of 5-chloro4-[2-(chloromethyl)phenyl]-2,4-dihydro-2-methyl-3H-1,2,4-triazol-3-one The title compound of Step A (58 g) was dissolved in 800 mL of dichloromethane and 86 g of triphosgene was added in one portion. A slight exotherm was observed, then the mixture was heated to reflux overnight. The reaction mixture was cooled and the solvent removed in vacuo. The resulting solid was dissolved in 1 L of ethyl acetate and washed with 500 mL of water, 500 mL of saturated aqueous sodium bicarbonate, and then 500 mL of saturated aqueous sodium chloride solution. The organic phase was dried (MgSO$_4$), filtered and concentrated to give a dark oil which solidified on standing. The solid was triturated in 2:1 hexane:n-butyl chloride to yield 32 g of a beige solid. Recrystallization of this solid from 150 mL of hot methanol yielded 21 g of the title compound of Step B as a white, fluffy solid melting at 122–124° C. A second crop was obtained from recrystallization of the mother liquors. $^1$NMR (CDCl$_3$): δ 7.45–7.6 (m,3H), 7.25 (m,1H), 4.68 (d,1H), 4.46 (d,1H), 3.56 (s,3H). Approximately 10% of 4-[2-(bromomethyl)phenyl]-5-chloro-2,4-dihydro-2-methyl-3H-1,2,4-triazol-3-one was observed in the $^1$NMR spectrum.

Step C Preparation of 1-(5,6,7,8-tetrahydro-2-naphthalenyl) ethanone oxime

To a solution of 6-acetyltetralin (5.0 g, 29 mmol) in methanol (30 mL) under a nitrogen atmosphere was added hydroxylamine hydrochloride (2.18 g, 32 mmol) and sodium acetate (2.59 g, 32 mmol) and the resulting mixture was stirred overnight. The reaction mixture was concentrated under reduced pressure and the residue was taken up in diethyl ether and washed with water and then with saturated sodium chloride solution. The organic phase was dried (MgSO$_4$) and concentrated under reduced pressure to afford an oil which solidified. The solid was pulverized and rinsed with hexanes to afford the title compound of Step C (3.85 g) as an off-white solid. $^1$H NMR (CDCl$_3$): δ 9.1 (br s,1H), 7.33 (m,2H), 7.07 (d,1H), 2.78 (m,4H), 2.27 (s,3H), 1.79 (m,4H).

Step D: Preparation of 5-chloro-2,4-dihydro-2-methyl-4-[2-[[[[1-(5,6,7,8-tetrahydro-2-naphthalenyl)ethylidene]amino]oxy]methyl]phenyl]-3H-1,2,4-triazol-3-one To a solution of the title compound of Step C (700 mg, 3.7 mmol) in dimethylformamide (10 mL) was added sodium hydride as a 60% oil dispersion (160 mg) followed by the title compound of Step B. The mixture was stirred at room temperature for 4 h and then was diluted with ethyl acetate. The solution was washed with water and then saturated sodium chloride solution. The organic phase was dried (MgSO$_4$) and concentrated under reduced pressure to afford an oil. Chromatography of this oil on silica gel with 20–30% ethyl acetate in hexanes afforded 1.0 g of the title compound of Step D, a compound of the invention, as an oil which solidified on standing. $^1$H NMR (CDCl$_3$): δ 7.68 (m,7H), 5.2 (m,2H), 3.47 (s,3H), 2.75 (m,4H), 2.15 (s,3H), 1.78 (m,4H). This material was used in the preparation of Example 4 without further characterization.

EXAMPLE 4

Preparation of 2,4-dihydro-5-methoxy-2-methyl-4-[2-[[[[1-(5,6,7,8-tetrahydro-2-naphthalenyl)ethylidene]amino]oxy]methyl]phenyl]-3H-1,2,4-triazol-3-one To a solution of the title compound of Step D in Example 3 (1.0 g, 2,4 mmol) in dimethoxyethane (2.5 mL) was added sodium methoxide as a 30% solution in methanol (1.4 mL, 7.3 mmol) and the resulting mixture was heated to reflux for 1 h. The mixture was allowed to cool to room temperature overnight and then was heated to reflux an additional 1.5 h. The mixture was cooled to room temperature and diluted with ethyl acetate and washed with water and then saturated sodium chloride solution. The organic phase was dried (MgSO$_4$) and concentrated under reduced pressure to afford an oil. Chromatography of this oil on silica gel with 50–60% ethyl acetate in hexanes afforded 550 mg of the title compound of Example 4, a compound of the invention, as an oil which, on standing, formed a solid melting at 106–109° C.

EXAMPLE 5

Step A: Preparation of methyl 2-amino-3-methylbenzoate

To a solution of 2-amino-3-methylbenzoic acid (25.0 g, 165 mmol) in p-dioxane (43 mL) under a nitrogen atmosphere was added diphosgene (20 mL, 165 mmol) and the resulting solution was stirred at 60° C. overnight. After cooling to room temperature, the mixture was filtered and the precipitate was rinsed with hexanes and dried in vacuo to afford 28.49 g of an off white solid. Without further characterization, this material was suspended in dry dimethylformamide (320 mL) and methanol (11.7 mL). 4-Dimethylaminopyridine (3.9 g) was added to this suspension and the resulting solution was stirred at 60° C. for 2 days. The cooled reaction mixture was diluted with saturated sodium bicarbonate solution and saturated ammonium chloride solution and extracted three times with ethyl acetate. The combined organic phases were dried (MgSO$_4$) and concentrated under reduced pressure to yield the title compound of Step A (25.40 g) as an oil. $^1$H NMR (CDCl$_3$): δ 7.73 (d, 1H), 7.10 (d, 1H), 6.52 (dd,1H), 5.85 (br s,2H), 3.80 (s,3H), 2.07 (s,3H). This material was used in Step B without further characterization.

Step B: Preparation of methyl 2-[[(2,2-dimethylhydrazino)carbonyl]amino]-3-methylbenzoate To a solution of the title compound of Step A (25.4 g, 154 mmol) in p-dioxane (500 mL) under a nitrogen atmosphere was added diphosgene (22.3 mL, 184 mmol), followed by triethylamine (25.6 mL, 184 mmol). A white precipitate formed, and the resulting mixture was heated to 60° C. overnight. The mixture was cooled to room temperature and filtered. The precipitate was washed with diethyl ether and the combined filtrates were concentrated under reduced pressure to afford an oil (30.97 g) which, without further characterization, was dissolved in toluene (400 mL). To this solution at 0° C. under a nitrogen atmosphere was added 1,1-dimethylhydrazine (12.3 mL, 162 mmol) and the resulting milky suspension was stirred at 0° C. for 30 min. The precipitate was collected by filtration and washed with hexanes to afford the title compound of Step B (25.57 g) as a beige solid. $^1$H NMR (CDCl$_3$): δ 9.22 (br s,1H), 7.75 (d,1H), 7.40 (d,1H), 7.14 (t,1H), 5.32 (br s,1H), 3.88 (s,3H), 2.66 (s,6H), 2.35 (s,3H).

Step C: Preparation of methyl 2-(3-chloro-1,5-dihydro-1-methyl-5-oxo-4H-1,2,4-triazol-4-yl)-3-methylbenzoate Into a solution of triphosgene (51.5 g, 174 mmol) in ethyl acetate (500 mL) heated to 75° C. was pumped a slurry of the title compound of Step B (15.57 g, 62 mmol) in ethyl acetate (100 mL) over 40 min. The mixture was held at 75° C. during the entire addition and then for an additional 2 h. The mixture was cooled to room temperature and stirred overnight. The reaction mixture was poured into saturated sodium bicarbonate solution and back-extracted with ethyl acetate. The combined organic phases were dried (MgSO$_4$) and concentrated under reduced pressure to afford the title compound of Step C (14.59 g) as an off white solid. $^1$H NMR (CDCl$_3$): δ 8.01 (dd,1H), 7.58 (d,1H), 7.50 (t,1H), 3.82 (s,3H), 3.56 (s,3H), 2.28 (s,3H).

Step D: Preparation of 5-chloro-2,4-dihydro-4-[2-(hydroxymethyl)-6-methylphenyl]-2-methyl-3H-1,2,4-triazol-3-one To a solution of the title compound of Step C (7.0 g, 24.8 mmol) in dichloromethane (60 mL) cooled to −78° C. under a nitrogen atmosphere was added a 1 Molar solution of DIBAL (diisobutylaluminum hydride) in dichloromethane (62 mL, 62 mmol). After the addition was complete, the reaction mixture was allowed to warm to room temperature for 1 h. An additional portion of 1 Molar solution of DIBAL in dichloromethane (31 mL) was added at −78° C. and the mixture warmed to room temperature for 1 h. The reaction was quenched with 1 N HCl and extracted three times with dichloromethane. The combined organic phases were washed with saturated ammonium chloride solution, dried (MgSO$_4$) and concentrated under reduced pressure. The residue was triturated to afford 4.4 g of the title compound of Step D as a solid. $^1$H NMR (CDCl$_3$): δ 7.44 (apparent d,2H), 7.33 (t,1H), 4.46 (m,2H), 3.57 (s,3H), 2.66 m,1H), 2.18 (s,3H).

Step E: Preparation of 4-[2-(bromomethyl)-6-methylphenyl]-5-chloro-2,4-dihydro-2-methyl-3H-1,2,4-triazol-3-one To a solution of the title compound of Step D (3.0 g, 12 mmol) in dichloromethane (56 mL) cooled to 0° C. under a nitrogen atmosphere was added triphenylphosphine (3.72 g, 14 mmol) followed by carbon tetrabromide (5.9 g, 18 mmol). The mixture was allowed to warm to room temperature and was stirred for 2 h. The mixture was concentrated under reduced pressure and the residue was purified by flash chromatography (2:1 hexanes:ethyl acetate) to afford 3.19 g of the title compound of Step E as a light yellow powder. $^1$H NMR (CDCl$_3$): δ 7.3–7.39 (m,3H), 4.35 (AB q,2H), 3.56 (s,3H), 2.16 (s,3H).

Step F: Preparation of 2,4-dihydro-5-methoxy-2-methyl4-[2-methyl-6-[[[[1-(2-naphthalenyl)ethylidene]amino]oxy]methyl]phenyl]-3H-1,2,4-triazol-3-one To a solution of 1-(2-naphthalenyl)ethanone oxime (492 mg, 2.65 mmol) in tetrahydrofuran (7.5 mL) cooled to 0° C. under a nitrogen atmosphere was added 95% NaH (69 mg, 2.88 mmol) and the mixture was stirred for 20 min. The title compound of Step E (700 mg, 2.21 mmol) was then added to the reaction and the mixture was stirred at room temperature for 3 h. Sodium methoxide as a 30% solution in methanol (1.3 mL, 6.63 mmol) was added and the reaction mixture was heated to reflux for 10 h. The reaction mixture was cooled to room temperature, diluted with ethyl acetate and washed with saturated ammonium chloride. The organic phase was dried (magnesium sulfate) and concentrated under reduced pressure. The crude product was purified by flash chromatography on silica gel (25% ethyl acetate in hexanes as eluent) to give 306 mg of the title compound of Step F, a compound of the invention, as a golden oil. $^1$H NMR (CDCl$_3$): δ 2.19 (s,3H), 2.32 (s,3H), 3.41 (s,3H), 3.89 (s,3H), 5.21 (AB q,2H), 7.30 (d,1H), 7.36–7.5 (m,4H), 7.8 (m,4H), 7.97 (s,1H).

EXAMPLE 6

Step A: Preparation of methyl 2-[[(2,2-dimethylhydrazino)carbonyl]amino]benzoate To a solution of 300 mL of toluene containing 50 g of 2-methoxycarbonylphenyl isocyanate at 0° C. under a nitrogen atmosphere was added dropwise 21.44 mL of 1,1-dimethylhydrazine. The reaction mixture was allowed to warm to room temperature and stirred overnight. The mixture was then cooled to approximately 0° C., filtered, and the solid was rinsed with hexane to give 61.5 g of the title compound of Step A as a white solid.

Step B: Preparation of methyl 2-(3-chloro-1,5-dihydro-1-methyl-5-oxo4H-1,2,4-triazol-4-yl)benzoate To a solution containing 61.5 g of the title compound of Step A dissolved in 1300 mL of dichloromethane under a nitrogen atmosphere was added 154 g of triphosgene portionwise with external cooling to maintain the reaction temperature at 0–20° C. The reaction mixture was then heated at reflux for approximately 24 h and then was cooled to 0° C. The reaction mixture was poured into water. The organic layer was separated and washed with water and saturated aqueous sodium chloride. The organic layer was then dried over magnesium sulfate, filtered and the filtrate was then evaporated to obtain 35.49 g of a white solid. This solid was purified by column chromatography on silica gel eluting with 2:1 hexane/ethyl acetate. Collection and evaporation of the fractions containing only the most polar component (according to thin layer chromatography on silica gel, 1:1 hexane/ethyl acetate mixture as the development solvent) yielded 12.2 g of the title compound of Step B as a white solid.

Step C: Preparation of methyl 2-(1,5-dihydro-3-methoxy-1-methyl-5-oxo-4H-1,2,4-triazol-4-yl)benzoate To a solution containing 10 g of the title compound of Step B dissolved in 110 mL of 1,2-dimethoxyethane and 50 mL of methanol under a nitrogen atmosphere was added dropwise 21.4 L of 30% sodium methoxide. The reaction mixture was stirred at room temperature for approximately 24 h, then heated to 40° C. for 1 h, then heated to 50° C. for 4 h, and finally cooled to 0° C. The reaction was poured into a saturated aqueous solution of ammonium chloride. The organic layer was separated and washed with saturated aqueous ammonium chloride. The organic layer was then dried over magnesium sulfate and filtered, and the filtrate was then evaporated to obtain 7.74 g of the title compound of Step C as a white solid.

Step D: Preparation of 2,4-dihydro-4-[2-(hydroxymethyl) phenyl]-5-methoxy-2-methyl-3H-1,2,4-triazol-3-one To a solution containing 6 g of the title compound of Step C dissolved in 120 mL of dichloromethane and cooled to −78° C. under a nitrogen atmosphere was added 68.4 mL of 1.0 M of diisobutylaluminum hydride. The reaction was stirred at −78° C. for 1 h, then was allowed to warm to room temperature and was stirred overnight. The reaction was then cooled to −78° C. and 10 mL of acetone was added dropwise. To this mixture at −78° C. was added 10 mL of 1N sodium hydroxide dropwise. The reaction mixture was allowed to warm to room temperature and was then poured into water, and the resulting mixture was extracted with dichloromethane. The organic extracts were washed with saturated aqueous sodium chloride, dried over magnesium sulfate and filtered. The filtrate was then evaporated to obtain 4.15 g of the title compound of Step D as a white solid melting at 117°–127° C. $^1$H NMR (400 MHz, CDCl$_3$): δ 3.472 (s,3H), 3.969 (m,4H), 4.4–4.56 (m,2H), 7.19 (d,1H), 7.423 (t,1H), 7.485 (t,1H), 7.547 (d,1H).

Step E: Preparation of 2,4-dihydro-5-methoxy-4-[2-[(7-methoxy-1,2,4-benzotriazin-3-yl)oxy]phenyl]-2-methyl-3H-1,2,4-triazol-3-one N-oxide To a solution of 25 mL of N,N-dimethylformamide containing 0.11 g of the title compound of Step D under a nitrogen atmosphere was added 0.17 g of potassium carbonate and 0.11 g of 3-chloro-7-methoxy-1,2,4-benzotriazine 1-oxide. The reaction mixture was stirred at room temperature for approximately 24 h, and was then poured into water and extracted with dichloromethane. The organic extracts were washed with water and saturated aqueous sodium chloride. The organic layer was dried over magnesium sulfate, filtered and the filtrate was then evaporated to obtain a yellow oil. The yellow oil was crystallized from 1-chlorobutane/hexane to yield 0.11 g of the title compound of Step E, a compound of the invention, as a yellow solid melting at 191–192° C. $^1$H NMR (400 MHz, CDCl$_3$): δ 3.250 (s,3H), 3.827 (s,3H), 3.964 (s,3H), 7.4–7.52 (m,5H), 7.65 (d,1H), 7.723 (d,1H).

EXAMPLE 7

Step A: Preparation of 2-(2-nitrophenoxy)naphthalene

To a stirred solution of 2-hydroxynaphthalene (5 g, 34.7 mmol) in anhydrous tetrahydrofuran was added 2-fluoronitrobenzene (4.90 g, 34.7 mmol) at room temperature. The resultant mixture was heated at reflux overnight. After cooling to room temperature, the reaction mixture was concentrated under reduced pressure, the residue was diluted with water, the resulting mixture was extracted twice with methylene chloride and the combined extracts were dried (MgSO$_4$). The resultant organic layer was concentrated under reduced pressure to yield 9.2 g of the title compound of Step A as an oil. R$_f$ 0.45 (silica gel, 4:1 hexane-ethyl acetate).

Step B: Preparation of 2-(2-naphthalenyloxy)benzenamine

A solution of the title compound of Step A (9.2 g, 34.7 mmol) and 10 mL water in 100 mL acetic acid was heated to 65° C. on a steam bath. Then the steam bath was removed and iron powder (6.4 g, 115 mmol) was added in portions so as to not allow the reaction temperature to exceed 90° C. After complete addition of the iron powder, the reaction mixture was heated at 85° C. for 5 minutes, cooled to room temperature, diluted with methylene chloride and filtered through Celite®. The filtrate was washed once with water, then twice with saturated aqueous sodium bicarbonate, dried (MgSO$_4$), and the organic solution was concentrated under reduced pressure to yield 7.6 g of the title compound of Step B as an oil. $^1$H NMR (CDCl$_3$, 300 MHz): δ 3.8 (br s,2H), 6.7–6.8 (m,1H), 6.9 (m,1H), 6.95 (m,1H), 7.0 (m,1H), 7.2–7.3 (m,2H), 7.3–7.5 (m,2H), 7.6–7.7 (m,1H), 7.8 (m,2H).

Step C: Preparation of 2-(2-isocyanatophenoxy)naphthalene

To a solution of the title compound of Step B (7.6 g, 32.3 mmol) in 150 mL of toluene was added trichloromethyl orthoformate (6.40 g, 32.3 mmol) at room temperature. The resultant mixture was then heated at reflux overnight. The reaction mixture was then concentrated under reduced pressure to yield the title compound of Step C as an oil which was then used entirely in Step D.

Step D: Preparation of 2,2-dimethyl-N-[2-(2-naphthalenyloxy)phenyl]hydrazinecarboxamide The title compound of Step C was dissolved in 100 mL of dry tetrahydrofuran and cooled to 0° C. Then 1,1-dimethylhydrazine (2.3 g, 38.2 mmol) was added at 0° C. The resultant mixture was stirred at room temperature overnight. The reaction mixture was concentrated under reduced pressure, diluted with water, extracted twice with methylene chloride and the combined extracts were dried (MgSO$_4$). The organic solution was then concentrated under reduced pressure to yield the title compound of Step D as a brown solid which was carried on entirely in Step E.

Step E: Preparation of 5-chloro-2,4-dihydro-2-methyl-4-[2-(2-naphthalenyloxy)phenyl]-3H-1,2,4-triazol-3-one The title compound of Step D was dissolved in 250 mL of methylene chloride. To this solution was added triphosgene (9.44 g, 31.8 mmol) in portions over 10 minutes. The resultant mixture was heated at reflux overnight. The reaction mixture was cooled to room temperature and concentrated under reduced pressure. The crude residue was then diluted with water, the resulting mixture was extracted twice with methylene chloride and the combined extracts were dried (MgSO$_4$). The organic solution was then concentrated under reduce pressure to give 10.7 g of the title compound of Step E, a compound of the invention, as a tan solid melting at 147–150° C. $^1$H NMR(CDCl$_3$, 300 MHz): δ 3.41 (s,3H), 7.05 (m,1H), 7.20 (m,1H), 7.3–7.5 (m,6H), 7.7 (m,1H), 7.8 (m,2H).

EXAMPLE 8

Preparation of 2,4-dihydro-5-methoxy-2-methyl-4-[2-(2-naphthalenyloxy)phenyl]-3H-1,2,4-triazol-3-one To a solution of the title compound of Step D in Example 7 (10.7 g, 31.7 mmol) in 150 mL methanol was added sodium methoxide (4.89 g, 90.6 mmol) at room temperature in portions. The resultant mixture was refluxed for 7 h, cooled to room temperature and concentrated under reduced pressure. The residue was diluted with 1N HCl, extracted twice with methylene chloride and the combined extracts were dried (MgSO$_4$). The organic solution was then concentrated under reduced pressure to give a tan solid which was chromatographed on silica gel with 1:1 hexane-ethyl acetate as the eluent to afford 6.5 g of the title compound of Example 8, a compound of the invention, as an oil. $^1$H NMR(CDCl$_3$, 300 MHz): δ 3.34 (s,3H), 3.82 (s,3H), 7.05 (m,1H), 7.21 (m,2H), 7.36–7.50 (m,5H), 7.71 (d,1H), 7.81 (d,2H).

By the procedures described herein together with methods known in the art, the following compounds of Tables 1 to 7 can be prepared. The following abbreviations are used in the Tables which follow: t=tertiary, Me=methyl, Bu=butyl, Ph=phenyl, nap=naphthalenyl, OMe=methoxy, OPh=phenoxy, SMe=methylthio, CN=cyano, and TMS=trimethylsilyl.

TABLE 1

Compounds of Formula I where A=N, G=N, W=O, X=OMe, R²=Me, R³=R⁴=H, Z=2-nap, the floating double bond is attached to A, and

| R⁹ | R⁹ | R⁹ | R⁹ | R⁹ |
|---|---|---|---|---|
| Y=CH₂ON=C(Me) | | | | |
| H | 6-Me | 6-OMe | 6-Br | 6-OH |
| 5-Br | 1-Br | 4-Me | 4-Cl | 6-CF₃ |
| 5-Me | 6-TMS | 6-C≡CH | 7-OCF₃ | 4-CF₃ |
| 8-Me | 6-Ph | 5-CN | 4-t-Bu | 6-OPh |
| 3-Me | 6-SF₅ | | | |
| Y=CH₂O | | | | |
| H | 6-Me | 6-OMe | 6-Br | 6-OH |
| 5-Br | 1-Br | 4-Me | 4-Cl | 6-CF₃ |
| 5-Me | 6-TMS | 6-C≡CH | 7-OCF₃ | 4-CF₃ |
| 8-Me | 6-Ph | 5-CN | 4-t-Bu | 6-OPh |
| 3-Me | 6-SF₅ | | | |

TABLE 2

Compounds of Formula I where A=O, G=C, W=O, X=OMe, R²=Me, R³=R⁴=H, Z=2-nap, the floating double bond is attached to G, and

| R⁹ | R⁹ | R⁹ | R⁹ | R⁹ |
|---|---|---|---|---|
| Y=CH₂ON=C(Me) | | | | |
| H | 6-Me | 6-OMe | 6-Br | 6-OH |
| 5-Br | 1-Br | 4-Me | 4-Cl | 6-CF₃ |
| 5-Me | 6-TMS | 6-C≡CH | 7-OCF₃ | 4-CF₃ |
| 8-Me | 6-Ph | 5-CN | 4-t-Bu | 6-OPh |
| 3-Me | 6-SF₅ | | | |
| Y=CH₂O | | | | |
| H | 6-Me | 6-OMe | 6-Br | 6-OH |
| 5-Br | 1-Br | 4-Me | 4-Cl | 6-CF₃ |
| 5-Me | 6-TMS | 6-C≡CH | 7-OCF₃ | 4-CF₃ |
| 8-Me | 6-Ph | 5-CN | 4-t-Bu | 6-OPh |
| 3-Me | 6-SF₅ | | | |

TABLE 3

Formula I where A=N, G=N, W=O, X=OMe, R²=Me, R³=R⁴=H, the floating double bond is attached to A, and

| Z | Z | Z |
|---|---|---|

Y = CH₂ON=C(Me)

TABLE 3-continued
Formula I where A=N, G=N, W=O, X=OMe, $R^2$=Me, $R^3$=$R^4$=H, the floating double bond is attached to A, and
| Z | Z | Z |
|---|---|---|
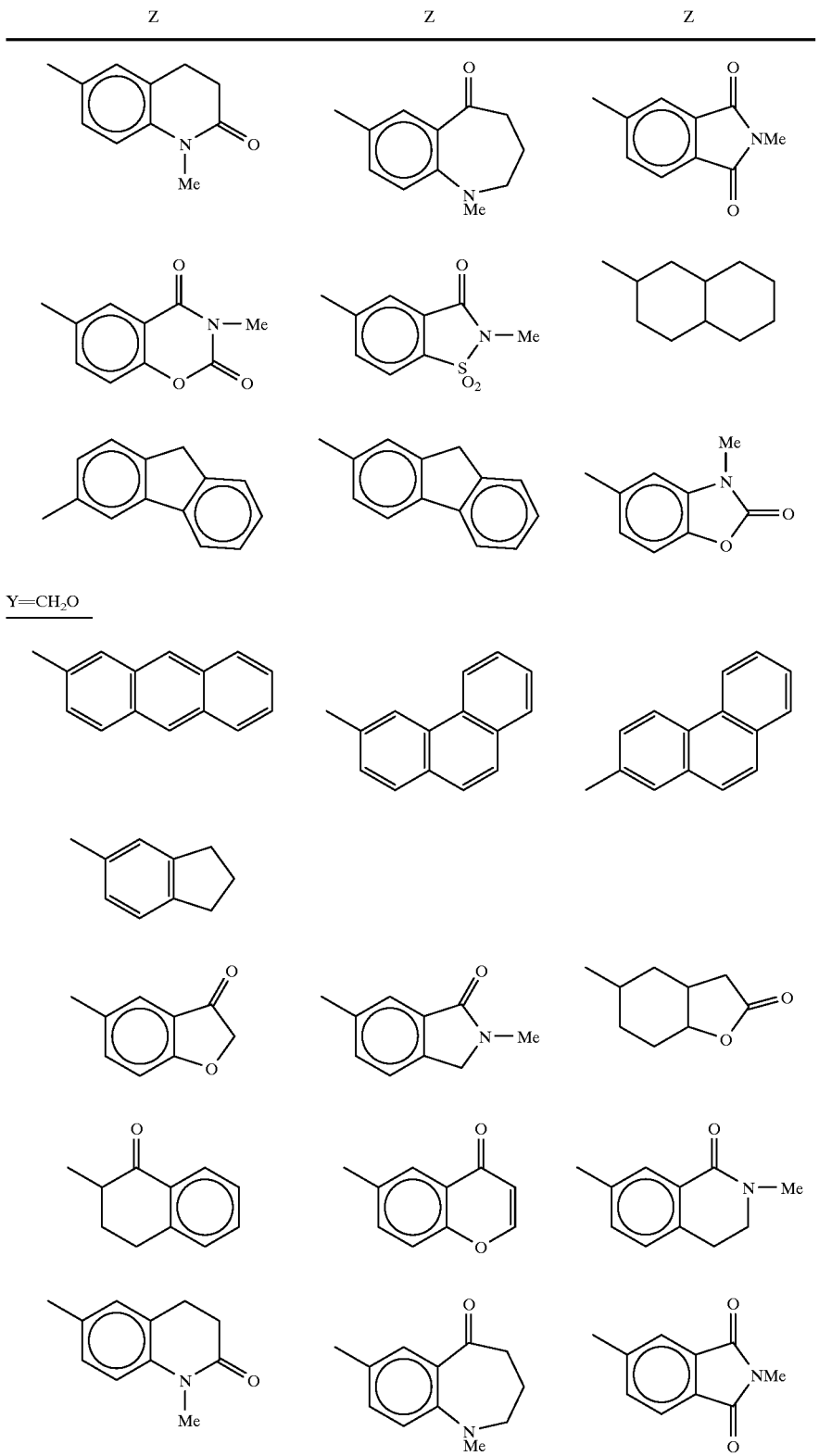
Y=$CH_2$O TABLE 3-continued
Formula I where A=N, G=N, W=O, X=OMe, R²=Me,
R³=R⁴=H, the floating double bond is attached to A, and
| Z | Z | Z |
|---|---|---|
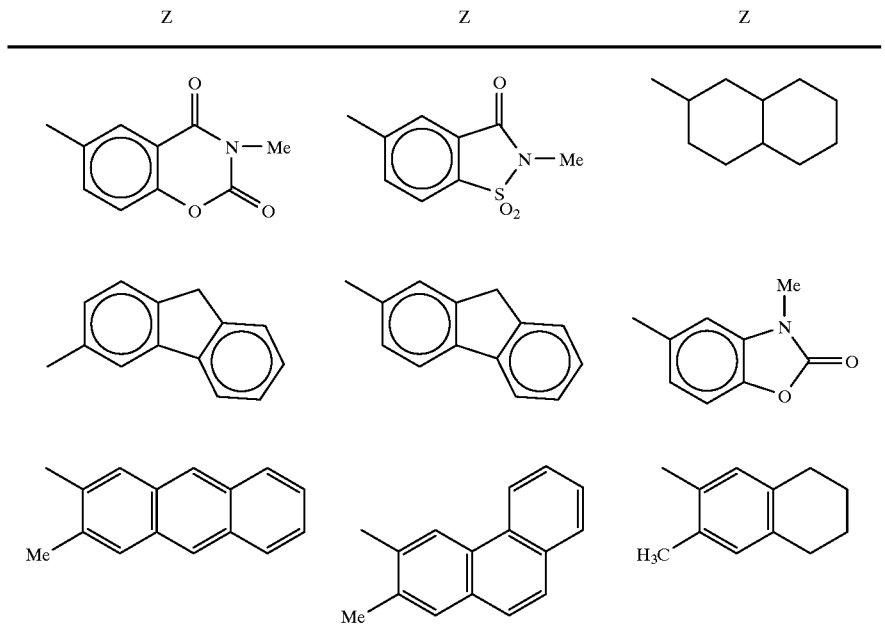
TABLE 4
Compounds of Formula I where A=O, G=C, W=O, X=OMe,
R²=Me, R³=R⁴=H, the floating double bond is attached to G, and
| Z | Z | Z |
|---|---|---|
Y=CH₂ON=C(Me)
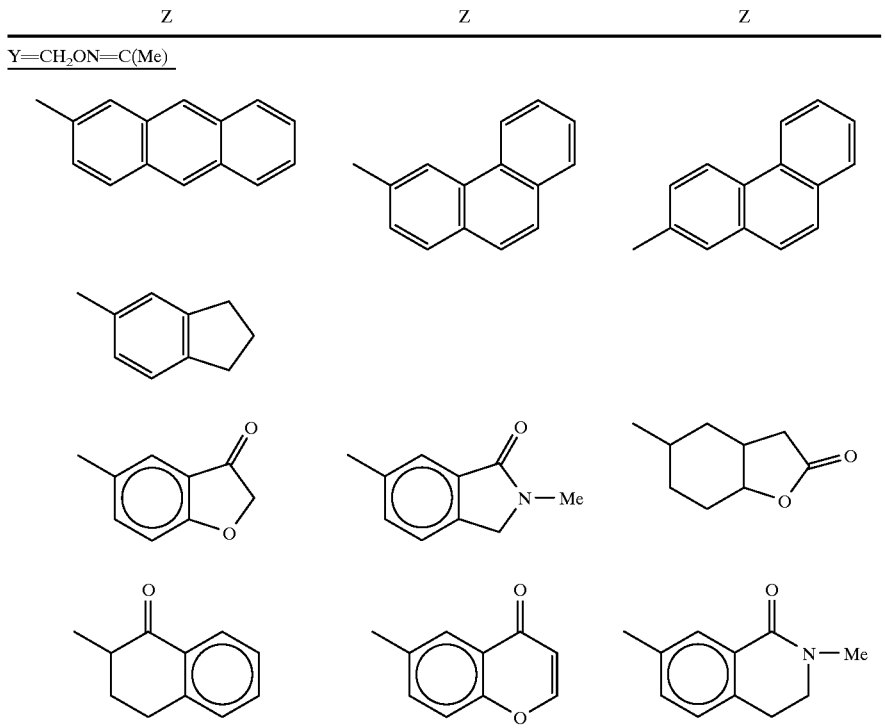

TABLE 4-continued
Compounds of Formula I where A=O, G=C, W=O, X=OMe,
R²=Me, R³=R⁴=H, the floating double bond is attached to G, and
| Z | Z | Z |
| --- | --- | --- |
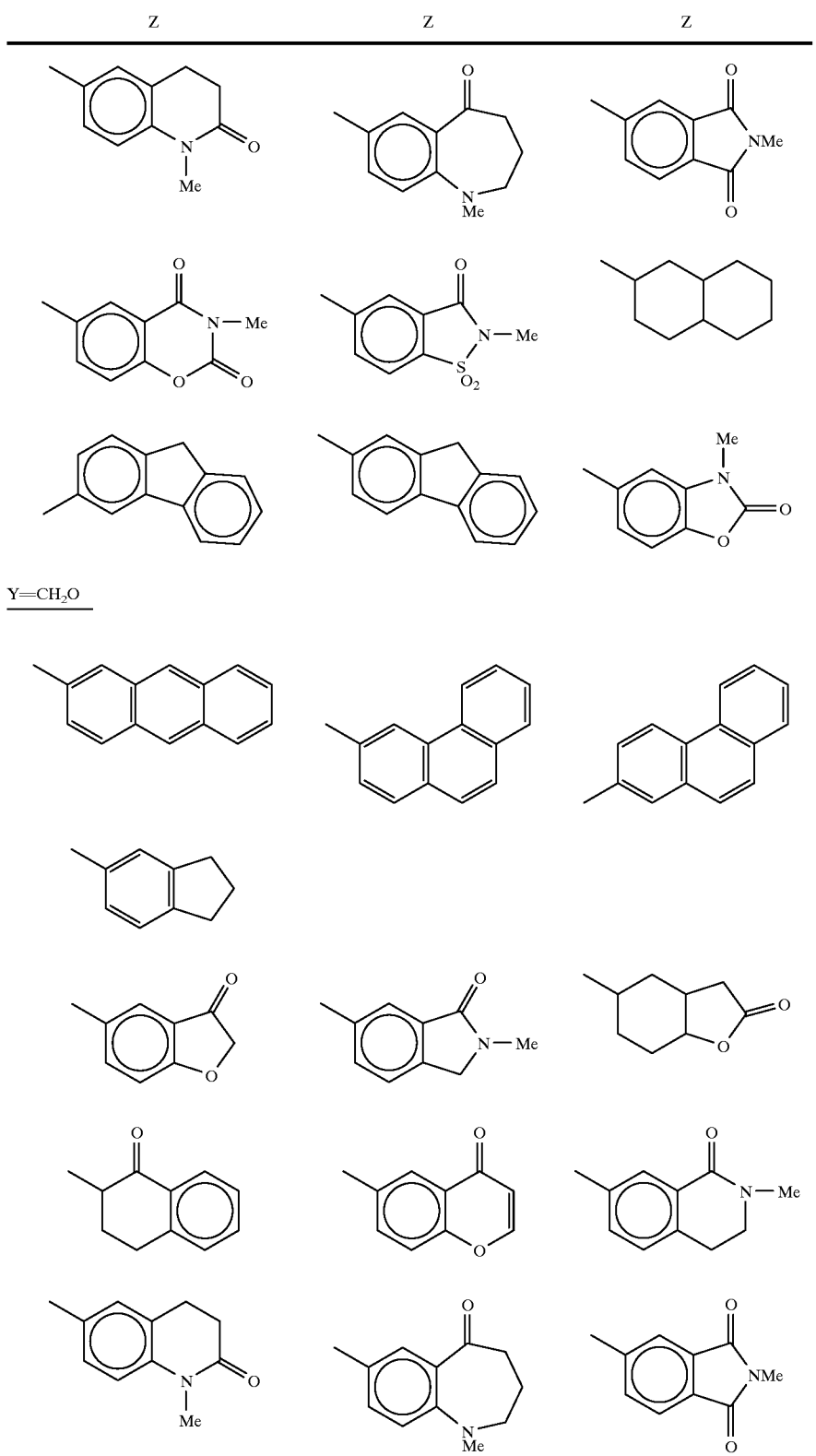
Y=CH₂O TABLE 4-continued Compounds of Formula I where A=O, G=C, W=O, X=OMe, R²=Me, R³=R⁴=H, the floating double bond is attached to G, and

| Z | Z | Z |
|---|---|---|
| (structure) | (structure) | (structure) |

TABLE 5

Compounds of Formula I where A=N, G=N, W=O, X=OMe, R²=Me, Z=2-nap, the floating double bond is attached to A, and

| R³ | R⁴ | R³ | R⁴ |
|---|---|---|---|
| Y=CH₂ON=C(Me) | | | |
| 6-OMe | H | 3-F | H |
| 4-OMe | H | 4-SMe | H |
| 6-F | H | 6-SMe | H |
| 5-Cl | H | 3-CN | H |
| 6-Me | H | 6-CN | H |
| 4-Me | H | 3-OCF₃ | H |
| 3-Me | H | 6-I | H |
| 3-SMe | H | 4-Me | 6-Me |
| 4-Br | H | 3-Me | 6-Me |
| 4-C≡CH | H | 3-CF₃ | 5-CF₃ |
| 5-CF₃ | H | 4-OMe | 5,6-di-OMe |
| 3-CF₃ | H | 4,5-OCH₂O— | |
| Y=CH₂O | | | |
| 6-OMe | H | 3-F | H |
| 4-OMe | H | 4-SMe | H |
| 6-F | H | 6-SMe | H |
| 5-Cl | H | 3-CN | H |
| 6-Me | H | 6-CN | H |
| 4-Me | H | 3-OCF₃ | H |
| 3-Me | H | 6-I | H |
| 3-SMe | H | 4-Me | 6-Me |
| 4-Br | H | 3-Me | 6-Me |
| 4-C≡CH | H | 3-CF₃ | 5-CF₃ |
| 5-CF₃ | H | 4-OMe | 5,6-di-OMe |
| 3-CF₃ | H | 4,5-OCH₂O— | |

TABLE 6

Compounds of Formula I where A=O, G=C, W=O, X=OMe, R²=Me, Z=2-nap, the floating double bond is attached to G, and

| R³ | R⁴ | R³ | R⁴ |
|---|---|---|---|
| Y=CH₂ON=C(Me) | | | |
| 6-OMe | R | 3-F | H |
| 4-OMe | H | 4-SMe | H |
| 6-F | H | 6-SMe | H |
| 5-Cl | H | 3-CN | H |
| 6-Me | H | 6-CN | H |
| 4-Me | H | 3-OCF₃ | H |
| 3-Me | H | 6-I | H |
| 3-SMe | H | 4-Me | 6-Me |
| 4-Br | H | 3-Me | 6-Me |
| 4-C≡CH | H | 3-CF₃ | 5-CF₃ |
| 5-CF₃ | H | 4-OMe | 5,6-di-OMe |
| 3-CF₃ | H | 4,5-OCH₂O— | |
| Y=CH₂O | | | |
| 6-OMe | H | 3-F | H |
| 4-OMe | H | 4-SMe | H |
| 6-F | H | 6-SMe | H |
| 5-Cl | H | 3-CN | H |
| 6-Me | H | 6-CN | H |
| 4-Me | H | 3-OCF₃ | H |
| 3-Me | H | 6-I | H |
| 3-SMe | H | 4-Me | 6-Me |
| 4-Br | H | 3-Me | 6-Me |
| 4-C≡CH | H | 3-CF₃ | 5-CF₃ |
| 5-CF₃ | H | 4-OMe | 5,6-di-OMe |
| 3-CF₃ | H | 4,5-OCH₂O— | |

TABLE 7

Compounds of Formula I where A=N, G=N, W=O, X=OMe, R²=Me, Z=5,6,7,8-tetrahydro-2-nap, the floating double bond is attached to A, and

| R³ | R⁴ | R³ | R⁴ |
|---|---|---|---|
| Y=CH₂ON=C(Me) | | | |
| 6-OMe | H | 3-F | H |
| 4-OMe | H | 4-SMe | H |
| 6-F | H | 6-SMe | H |
| 5-Cl | H | 3-CN | H |
| 6-Me | H | 6-CN | H |
| 4-Me | H | 3-OCF₃ | H |
| 3-Me | H | 6-I | H |
| 3-SMe | H | 4-Me | 6-Me |
| 4-Br | H | 3-Me | 6-Me |
| 4-C≡CH | H | 3-CF₃ | 5-CF₃ |
| 5-CF₃ | H | 4-OMe | 5,6-di-OMe |
| 3-CF₃ | H | | 4,5-OCH₂O— |
| Y=CH₂O | | | |
| 6-OMe | H | 3-F | H |
| 4-OMe | H | 4-SMe | H |
| 6-F | H | 6-SMe | H |
| 5-Cl | H | 3-CN | H |
| 6-Me | H | 6-CN | H |
| 4-Me | H | 3-OCF₃ | H |
| 3-Me | H | 6-I | H |
| 3-SMe | H | 4-Me | 6-Me |
| 4-Br | H | 3-Me | 6-Me |
| 4-C≡CH | H | 3-CF₃ | 5-CF₃ |
| 5-CF₃ | H | 4-OMe | 5,6-di-OMe |
| 3-CF₃ | H | | 4,5-OCH₂O— |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, N.Y., 1950. *McCutcheon 's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147–48, *Perry's Chemical Engineer's Handbook*, 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299, 566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook*, 8th Ed., Blackwell Scientific Publications, Oxford, 1989.

In the following Examples, all percentages are by weight and all formulations are prepared in conventional ways. Compound numbers refer to compounds in Index Tables A–F.

Example A

Wettable Powder

| | |
|---|---|
| Compound 7 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example B

Granule

| | |
|---|---|
| Compound 7 | 10.0% |
| attapulgite granules (low volatile matter, 0.71/0.30 mm; U.S.S. No. 25-50 sieves) | 90.0%. |

Example C

Extruded Pellet

| | |
|---|---|
| Compound 7 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example D

Emulsifiable Concentrate

| | |
|---|---|
| Compound 7 | 20.0% |
| blend of oil soluble sulfonates and polyoxyethylene ethers | 10.0% |
| isophorone | 70.0%. |

The compounds of this invention are useful as plant disease control agents. The present invention therefore further comprises a method for controlling plant diseases caused by fungal plant pathogens comprising applying to the plant or portion thereof to be protected, or to the plant seed or seedling to be protected, an effective amount of a compound of the invention or a fungicidal composition containing said compound. The compounds and compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, vegetable, field, cereal, and fruit crops. These pathogens include *Plasmopara viticola, Phytophthora infestans, Peronospora tabacina, Pseudoperonospora cubensis, Pythium aphanidermatum, Alternaria brassicae, Septoria nodorum, Septoria tritici, Cercosporidium personatum, Cercospora arachidicola, Pseudocercosporella herpotrichoides, Cercospora beticola, Botrytis cinerea, Monilinia fructicola, Pyricularia oryzae, Podosphaera leucotricha, Venturia inaequalis, Erysiphe graminis, Uncinula necatur, Puccinia recondita, Puccinia graminis, Hemileia vastatrix, Puccinia striiformis, Puccinia arachidis, Rhizoctonia solani, Sphaerotheca fuliginea, Fusarium oxysporum, Verticillium dahliae, Pythium aphanidermatum, Phytophthora megasperma, Sclerotinia sclerotiorum, Sclerotium rolfsii, Erysiphe polygoni, Pyrenophora teres, Gaeumannomyces graminis, Rynchosporium secalis, Fusarium roseum, Bremia lactucae* and other genera and species closely related to these pathogens.

Compounds of this invention can also be mixed with one or more other insecticides, fungicides, nematocides, bactericides, acaricides, growth regulators, chemosterilants, semiochemicals, repellents, attractants, pheromones, feeding stimulants or other biologically active compounds to form a multi-component pesticide giving an even broader spectrum of agricultural protection. Examples of such agricultural protectants with which compounds of this invention can be formulated are: insecticides such as abamectin, acephate, azinphos-methyl, bifenthrin, buprofezin, carbofuran, chlorpyrifos, chlorpyrifos-methyl, cyfluthrin, beta-cyfluthrin, deltamethrin, diafenthiuron, diazinon, diflubenzuron, dimethoate, esfenvalerate, fenpropathrin, fenvalerate, fipronil, flucythrinate, tau-fluvalinate, fonophos, imidacloprid, isofenphos, malathion, metaldehyde, methamidophos, methidathion, methomyl, methoprene, methoxychlor, monocrotophos, oxamyl, parathion, parathion-methyl, permethrin, phorate, phosalone, phosmet, phosphamidon, pirimicarb, profenofos, rotenone, sulprofos, tebufenozide, tefluthrin, terbufos, tetrachlorvinphos, thiodicarb, tralomethrin, trichlorfon and triflumuron; fungicides such as azoxystrobin (ICIA5504), benomyl, blasticidin-S, Bordeaux mixture (tribasic copper sulfate), bromuconazole, captafol, captan, carbendazim, chloroneb, chlorothalonil, copper oxychloride, copper salts, cymoxanil, cyproconazole, cyprodinil (CGA 219417), diclomezine, dicloran, difenoconazole, dimethomorph, diniconazole, diniconazole-M, dodine, edifenphos, epoxyconazole (BAS 480F), fenarimol, fenbuconazole, fenpiclonil, fenpropidin, fenpropimorph, fluquinconazole, flusilazole, flutolanil, flutriafol, folpet, fosetyl-aluminum, furalaxyl, hexaconazole, ipconazole, iprobenfos, iprodione, isoprothiolane, kasugamycin, kresoxim-methyl (BAS 490F), mancozeb, maneb, mepronil, metalaxyl, metconazole, myclobutanil, neo-asozin (ferric methanearsonate), oxadixyl, penconazole, pencycuron, probenazole, prochloraz, propiconazole, pyrifenox, pyroquilon, sulfur, tebuconazole, tetraconazole, thiabendazole, thiophanate-methyl, thiram, triadimefon, triadimenol, tricyclazole, triticonazole, uniconazole, validamycin and vinclozolin; nematocides such as aldoxycarb and fenarniphos; bactericides such as streptomycin; acaricides such as amitraz, chinomethionat, chlorobenzilate, cyhexatin, dicofol, dienochlor, fenazaquin, fenbutatin oxide, fenpropathrin, fenpyroximate, hexythiazox, propargite, pyridaben and tebufenpyrad; and biological agents such as *Bacillus thuringiensis, Bacillus thuringiensis* delta endotoxin, baculovirus, and entomopathogenic bacteria, virus and fungi.

In certain instances, combinations with other fungicides having a similar spectrum of control but a different mode of action will be particularly advantageous for resistance management.

Preferred are mixtures of a compound of the invention with a fungicide selected from the group cyproconazole, cyprodinil (CGA 219417), epoxyconazole (BAS 480F), fenpropidin, fenpropimorph, flusilazole and tebuconazole. Specifically preferred mixtures (compound numbers refer to compounds in Index Tables A–F) are selected from the group: compound 1 and cyproconazole; compound 1 and cyprodinil (CGA 219417); compound 1 and epoxyconazole (BAS 480F); compound 1 and fenpropidin; compound 1 and fenpropimorph; compound 1 and flusilazole; compound 1 and tebuconazole; compound 7 and cyproconazole; compound 7 and cyprodinil (CGA 219417); compound 7 and epoxyconazole (BAS 480F); compound 7 and fenpropidin; compound 7 and fenpropimorph; compound 7 and flusilazole; compound 7 and tebuconazole; compound 10 and cyproconazole; compound 10 and cyprodinil (CGA 219417); compound 10 and epoxyconazole (BAS 480F); compound 10 and fenpropidin; compound 10 and fenpropimorph; compound 10 and flusilazole; and compound 10 and tebuconazole.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to the seed to protect the seed and seedling.

Rates of application for these compounds can be influenced by many factors of the environment and should be determined under actual use conditions. Foliage can normally be protected when treated at a rate of from less than 1 g/ha to 5,000 g/ha of active ingredient. Seed and seedlings can normally be protected when seed is treated at a rate of from 0.1 to 10 g per kilogram of seed.

The following TESTS demonstrate the control efficacy of compounds of this invention on specific pathogens. The pathogen control protection afforded by the compounds is not limited, however, to these species. See Index Tables A–F for compound descriptions. The following abbreviations are used in the Index Tables which follow: n=normal, Me=methyl, Pr=propyl, Bu=butyl, MeO=methoxy.

INDEX TABLE B

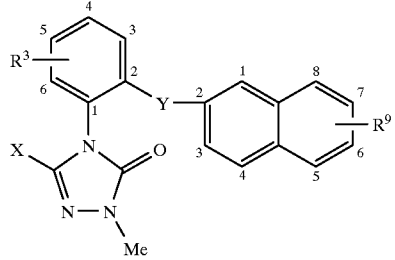

| Compd No. | X | $R^3$ | $R^9$ | Y | m.p. (°C.) |
|---|---|---|---|---|---|
| 9 | MeO | H | H | —CH$_2$ON=C(OMe)— | oil* |
| 10 (Ex. 5) | MeO | 6-Me | H | —CH$_2$ON=C(Me)— | oil* |
| 11 (Ex. 7) | Cl | H | H | —O— | 147–150 |
| 12 (Ex. 8) | MeO | H | H | —O— | oil* |
| 13 | MeO | H | 7-MeO | —O— | oil* |

INDEX TABLE A

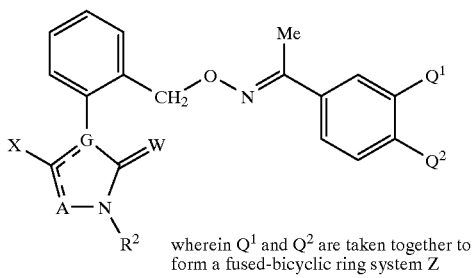

wherein $Q^1$ and $Q^2$ are taken together to form a fused-bicyclic ring system Z

| Compd No. | G | A | W | X | $R^2$ | $Q^1$-$Q^2$ | m.p. (°C.) |
|---|---|---|---|---|---|---|---|
| 1 (Ex. 2) | N | N | O | MeO | Me | CH=CH—CH=CH | 91–94 |
| 2 (Ex. 1) | C | O | O | MeO | Me | CH=CH—CH=CH | oil* |
| 3 | C | O | O | MeO | Me | CH=CH—C(Me)=CH | oil* |
| 4 | C | O | O | MeO | Me | CH=CH—C(OMe)=CH | oil* |
| 5 | C | O | O | MeO | Me | CH=CH—C(Br)=CH | oil* |
| 6 | C | O | O | MeO | Me | (CH$_2$)$_4$ | oil* |
| 7 (Ex. 4) | N | N | O | MeO | Me | (CH$_2$)$_4$ | 106–109 |
| 8 | N | N | O | MeO | Me | C(CH$_3$)$_2$(CH$_2$)$_2$C(CH$_3$)$_2$ | oil* |

INDEX TABLE C

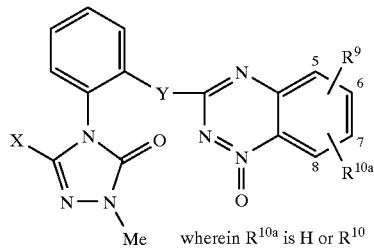

wherein R<sup>10a</sup> is H or R<sup>10</sup>

| Compd No. | X | R⁹ | R¹⁰ᵃ | Y | m.p. (°C.) |
|---|---|---|---|---|---|
| 14 | Cl | H | H | —CH₂O— | 159–162 |
| 15 | Cl | 5-Me | 7-Me | —CH₂O— | 204–209 |
| 16 | Cl | 6-Cl | H | —CH₂O— | 175–181 |
| 17 | MeO | 5-Me | 7-Me | —CH₂O— | 187–197 |
| 18 | MeO | 6-Br | 7-Me | —CH₂O— | 205–209 |
| 19 | MeO | 5-Me | H | —CH₂O— | 205–208 |
| 20 | MeO | 5-Me | 6-Me | —CH₂O— | 210–214 |
| 21 | MeO | 5-Me | 7-Me | —O— | 210–216 |
| 22 | MeO | 7-MeO | H | —O— | 191–192 |
| 23 | MeO | 7-Cl | H | —CH₂O— | 225–229 |
| 24 | MeO | 7-MeO | H | —CH₂O— | 207–210 |
| 25 | MeO | 6-Me | 7-Me | —O— | 218–219 |
| 26 | MeO | 5-Me | H | —O— | 195–199 |
| 27 | MeO | 6-Br | 7-Me | —O— | 187–189 |

INDEX TABLE D

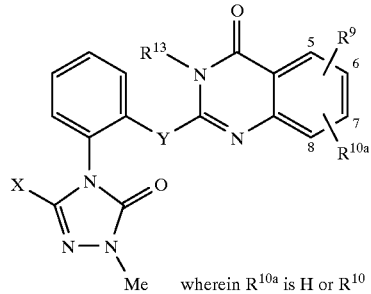

wherein R$^{10a}$ is H or R$^{10}$

| Compd No. | X | R¹³ | R⁹ | R¹⁰ᵃ | Y | m.p. (°C.) |
|---|---|---|---|---|---|---|
| 28 | MeO | n-Bu | 6-I | 8-I | —CH₂O— | 166–169 |
| 29 | MeO | n-Pr | 6-Br | 8-Br | —CH₂O— | 160–163 |
| 30 | MeO | Me | 6-I | H | —CH₂O— | 200–204 |
| 31 | MeO | n-Bu | 6-I | 8-I | —O— | 165–167 |

INDEX TABLE E

| Compd No. | Structure | m.p. (°C.) |
|---|---|---|
| 32 | (structure shown) | oil* |

*See Index Table F for ¹H NMR data.

INDEX TABLE F

| Cmpd No. | ¹H NMR Data (CDCl₃ solution unless indicated otherwise)ᵃ |
|---|---|
| 2 | δ 2.34 (s, 3H), 3.43 (s, 3H), 3.93 (s, 3H), 5.33 (s, 2H), 7.35 (m, 3H), 7.47 (m, 2H), 7.56 (t, 1H), 7.83 (m, 4H), 7.97 (d, 1H). |
| 3 | δ 2.34 (s, 3H), 2.51 (s, 3H), 3.44 (d, 3H), 3.94 (d, 3H), 5.32 (s, 2H), 7.35 (m, 4H), 7.565 (m, 2H), 7.71 (m, 2H), 7.83 (m, 1H), 7.93 (s, 1H). |
| 4 | δ 2.33 (s, 3H), 3.43 (s, 3H), 3.91 (s, 3H), 3.93 (s, 3H), 5.32 (s, 2H), 7.13 (m, 2H), 7.35 (m, 3H), 7.56 (m, 1H), 7.70 (m, 1H), 7.75 (m, 1H), 7.83 (m, 1H), 7.905 (s, 1H). |
| 5 | δ 2.33 (s, 3H), 3.44 (s, 3H), 3.95 (s, 3H), 5.33 (s, 2H), 7.35 (m, 3H), 7.55 (m, 2H), 7.70 (t, 2H), 7.925 (m, 3H). |
| 6 | δ 1.78 (m, 4H), 2.21 (s, 3H), 2.75 (d, 4H), 3.43 (s, 3H), 3.92 (s, 3H), 5.26 (s, 2H), 7.01 (m, 1H), 7.20 (m, 1H), 7.32 (m, 5H), 7.52 (m, 1H). |
| 8 | δ 1.26 (m, 12H), 1.68 (s, 4H), 2.18 (s, 3H), 3.41 (s, 3H), 3.89 (s, 3H), 5.20 (d, 1H), 5.23 (d, 1H), 7.25 (m, 2H), 7.3–7.5 (m, 4H). |
| 9 | δ 3.41 (s, 3H), 3.88 (s, 3H), 4.02 (s, 3H), 5.17 (AB q, 2H), 7.25 (m, 1H), 7.46 (m, 4H), 7.64 (m, 1H), 7.8 (m, 4H), 8.12 (s, 1H). |
| 10 | δ 2.19 (s, 3H), 2.32 (s, 3H), 3.41 (s, 3H), 3.89 (s, 3H), 5.21 (AB q, 2H), 7.30 (d, 1H), 7.36–7.5 (m, 4H), 7.8 (m, 4H), 7.97 (s, 1H). |
| 12 | δ 3.34 (s, 3H), 3.82 (s, 3H), 7.05 (m, 1H), 7.21 (m, 2H), 7.36–7.50 (m, 5H), 7.71 (d, 1H), 7.81 (d, 2H). |
| 13 | δ 3.35 (s, 3H), 3.84 (s, 3H), 3.88 (s, 3H), 7.0 (m, 4H), 7.2 (m, 2H), 7.4 (m, 2H), 7.71 (dd, 2H), 8.03 (s, 1H). |

INDEX TABLE F-continued

| Cmpd No. | ¹H NMR Data (CDCl₃ solution unless indicated otherwise)[a] |
|---|---|
| 32 | δ 1.6–1.8 (m, 13H), 2.0–2.1 (m, 5H), 3.44 (s, 3H), 3.94 (s, 3H), 5.09 (s, 2H), 7.32 (m, 3H), 7.48 (m, 1H). |

[a]¹H NMR data are in ppm downfield from tetramethylsilane. Couplings are designated by
(s)-singlet,
(d)-doublet,
(t)-triplet,
(q)-quartet,
(m)-multiplet,
AB q = "AB" quartet.

BIOLOGICAL EXAMPLES OF THE INVENTION

Test compounds were first dissolved in acetone in an amount equal to 3% of the final volume and then suspended at a concentration of 200 ppm in purified water containing 250 ppm of the surfactant Trem® 014 (polyhydric alcohol esters). The resulting test suspensions were then used in the following tests. Spraying these 200 ppm test suspensions to the point of run-off on the test plants is the equivalent of a rate of 500 g/ha.

TEST A

The test suspension was sprayed to the point of run-off on wheat seedlings. The following day the seedlings were inoculated with a spore dust of *Erysiphe graminis* f sp. tritici, (the causal agent of wheat powdery mildew) and incubated in a growth chamber at 20° C. for 7 days, after which disease ratings were made.

TEST B

The test suspension was sprayed to the point of run-off on wheat seedlings. The following day the seedlings were inoculated with a spore suspension of *Puccinia recondita* (the causal agent of wheat leaf rust) and incubated in a saturated atmosphere at 20° C. for 24 h, and then moved to a growth chamber at 20° C. for 6 days, after which disease ratings were made.

TEST C

The test suspension was sprayed to the point of run-off on rice seedlings. The following day the seedlings were inoculated with a spore suspension of *Pyricularia oryzae* (the causal agent of rice blast) and incubated in a saturated atmosphere at 27° C. for 24 h, and then moved to a growth chamber at 30° C. for 5 days, after which disease ratings were made.

TEST D

The test suspension was sprayed to the point of run-off on tomato seedlings. The following day the seedlings were inoculated with a spore suspension of *Phytophthora infestans* (the causal agent of potato and tomato late blight) and incubated in a saturated atmosphere at 20° C. for 24 h, and then moved to a growth chamber at 20° C. for 5 days, after which disease ratings were made.

TEST E

The test suspension was sprayed to the point of run-off on grape seedlings. The following day the seedlings were inoculated with a spore suspension of *Plasmopara viticola* (the causal agent of grape downy mildew) and incubated in a saturated atmosphere at 20° C. for 24 h, moved to a growth chamber at 20° C. for 6 days, and then incubated in a saturated atmosphere at 20° C. for 24 h, after which disease ratings were made.

TEST F

The test suspension was sprayed to the point of run-off on cucumber seedlings. The following day the seedlings were inoculated with a spore suspension of *Botrytis cinerea* (the causal agent of gray mold on many crops) and incubated in a saturated atmosphere at 20° C. for 48 h, and moved to a growth chamber at 20° C. for 5 days, after which disease ratings were made.

Results for Tests A–F are given in Table A. In the table, a rating of 100 indicates 100% disease control and a rating of 0 indicates no disease control (relative to the controls). A dash (-) indicates no test results.

TABLE A

| Cmpd No. | Test A | Test B | Test C | Test D | Test E | Test F |
|---|---|---|---|---|---|---|
| 1 | 98 | 100 | 94 | 97 | 100* | 18 |
| 2 | 89 | 100 | 74 | 92 | 82* | 0 |
| 3 | 98 | 93 | 53 | 93 | 72* | 91 |
| 4 | 99 | 81 | 32 | 75 | 37* | 60 |
| 5 | 95 | 99 | 51 | 92 | 86* | 68 |
| 6 | 98* | 100 | 94 | 92 | 89* | 80 |
| 7 | 95 | 100 | 74 | 63 | 100* | 0 |
| 8 | 87 | 100 | 91 | 26 | 87* | 49 |
| 9 | 99 | 99 | 91 | 100 | 99* | 64 |
| 10 | 86 | 99 | 85 | 94** | 100* | 0 |
| 11 | 89 | 86 | 0 | 12 | — | 0 |
| 12 | 50 | 94 | 0 | 57 | 23* | 0 |
| 13 | 63 | 67 | 85 | 82 | — | 0 |
| 14 | 0 | 20 | 0 | 91 | — | 64 |
| 15 | 0 | 0 | 0 | 96 | 0* | 0 |
| 16 | 0 | 20 | 0 | 71 | 0* | 0 |
| 17 | 98 | 93 | 0 | 24 | 16* | 32 |
| 18 | 92 | 85 | 0 | 93 | 100** | 0 |
| 19 | 62 | 85 | 0 | 0 | — | 0 |
| 20 | 98 | 86 | 0 | 18 | 10* | 0 |
| 21 | 61 | 94 | 0 | 92 | 100* | 0 |
| 22 | 77 | 94 | 0 | 85 | 1* | 43 |
| 23 | 92 | 68 | 0 | 60 | 20* | 0 |
| 24 | 60 | 93 | 0 | 63 | 8* | 32 |
| 25 | 95 | 93 | 0 | 92 | — | 0 |
| 26 | 97 | 100 | 73 | 100 | — | 0 |
| 27 | 91 | 97 | 30 | 84 | — | 0 |
| 28 | 73 | 85 | 0 | 0 | — | 82 |
| 29 | 73 | 85 | 53 | 25 | 16* | 0 |
| 30 | 90 | 93 | 53 | 0 | 28* | 45 |
| 31 | 61 | 68 | 0 | 41 | 1* | 0 |
| 32 | 69 | 100 | 0 | 25 | 55* | 41 |

*The compound was sprayed at a concentration of 10 ppm.
**The compound was sprayed at a concentration of 40 ppm.

What is claimed is:

1. A compound selected from Formula I, N-oxides and agriculturally-suitable salts thereof,

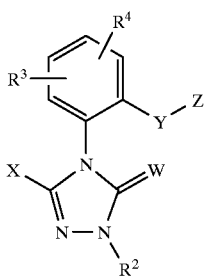

wherein:

W is O; S; NH; N(C$_1$–C$_6$ alkyl); or NO(C$_1$–C$_6$ alkyl);

X is OR$^1$; S(O)$_m$R$^1$; or halogen;

R$^1$ is H; C$_1$–C$_6$ alkyl; C$_1$–C$_6$ haloalkyl; C$_2$–C$_6$ alkenyl; C$_2$–C$_6$ haloalkenyl; C$_2$–C$_6$ alkynyl; C$_2$–C$_6$ haloalkynyl; C$_3$–C$_6$ cycloalkyl; C$_2$–C$_4$ alkylcarbonyl; or C$_2$–C$_4$ alkoxycarbonyl;

R$^2$ is H; C$_1$–C$_6$ alkyl; C$_1$–C$_6$ haloalkyl; C$_2$–C$_6$ alkenyl; C$_2$–C$_6$ haloalkenyl; C$_2$–C$_6$ alkynyl; C$_2$–C$_6$ haloalkynyl; C$_3$–C$_6$ cycloalkyl; C$_2$–C$_4$ alkylcarbonyl; C$_2$–C$_4$ alkoxycarbonyl; hydroxy; C$_1$–C$_2$ alkoxy; or acetyloxy;

R$^3$ and R$^4$ are each independently H; halogen; cyano; nitro; hydroxy; C$_1$–C$_6$ alkyl; C$_1$–C$_6$ haloalkyl; C$_2$–C$_6$ alkenyl; C$_2$–C$_6$ haloalkenyl; C$_2$–C$_6$ alkynyl; C$_2$–C$_6$ haloalkynyl; C$_1$–C$_6$ alkoxy; C$_1$–C$_6$ haloalkoxy; C$_2$–C$_6$ alkenyloxy; C$_2$–C$_6$ alkynyloxy; C$_1$–C$_6$ alkylthio; C$_1$–C$_6$ alkylsulfinyl; C$_1$–C$_6$ alkylsulfonyl; formyl; C$_2$–C$_6$ alkylcarbonyl; C$_2$–C$_6$ alkoxycarbonyl; NH$_2$C(O); (C$_1$–C$_4$ alkyl)NHC(O); (C$_1$–C$_4$ alkyl)$_2$NC(O); Si(R$^{25}$)$_3$; Ge(R$^{25}$)$_3$; (R$^{25}$)$_3$Si—C≡C—; or phenyl, phenylethynyl, benzoyl, or phenylsulfonyl each substituted with R$^8$ and optionally substituted with one or more R$^{10}$;

Y is —O—; —S(O)$_n$—; —NR$^6$—; —C(=O)—; —CH(OR$^6$)—; —CHR$^6$—; —CHR$^6$CHR$^6$—; —CR$^6$=CR$^6$—; —C≡C—; —CHR$^6$O—; —OCHR$^6$—; —CHR$^6$S(O)$_n$—; —S(O)$_n$CHR$^6$—; —CHR$^6$O—N=C(R$^7$)—; —(R$^7$)C=N—OCH(R$^6$)—; —C(R$^7$)=N—O—; —O—N=C(R$^7$)—; —CHR$^6$OC(=O)N(R$^{15}$)—; or a direct bond; and the directionality of the Y linkage is defined such that the moiety depicted on the left side of the linkage is bonded to the phenyl ring and the moiety on the right side of the linkage is bonded to Z;

each R$^6$ is independently H or C$_1$–C$_3$ alkyl;

R$^7$ is H; C$_1$–C$_6$ alkyl; C$_1$–C$_6$ haloalkyl; C$_1$–C$_6$ alkoxy; C$_1$–C$_6$ haloalkoxy; C$_1$–C$_6$ alkylthio; C$_1$–C$_6$ alkylsulfinyl; C$_1$–C$_6$ alkylsulfonyl; C$_1$–C$_6$ haloalkylthio; C$_1$–C$_6$ haloalkylsulfinyl; C$_1$–C$_6$ haloalkylsulfonyl; C$_2$–C$_6$ alkenyl; C$_2$–C$_6$ haloalkenyl; C$_2$–C$_6$ alkynyl; C$_2$–C$_6$ haloalkynyl; C$_3$–C$_6$ cycloalkyl; C$_2$–C$_4$ alkylcarbonyl; C$_2$–C$_4$ alkoxycarbonyl; halogen; cyano; or morpholinyl;

Z is a ring system selected from:

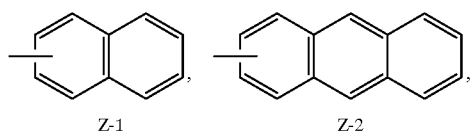

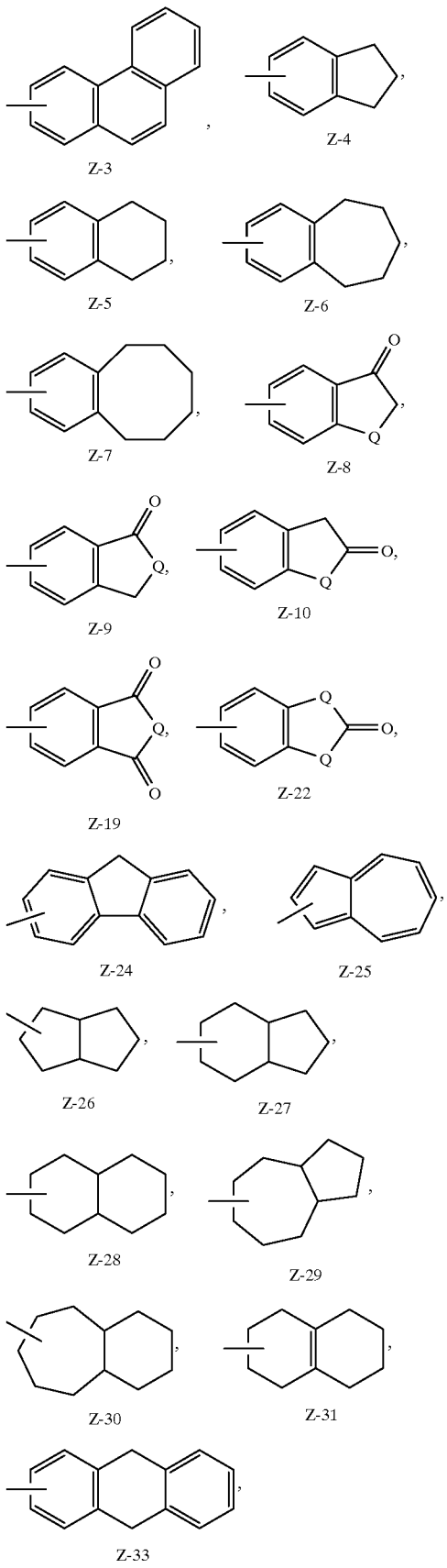

-continued

Z-35

Z-40

Z-41

Z-42

Z-45

Z-47

Z-48

Z-53

Z-54 and Z-57 where the point of attachment with Y is selected from any available position on the entire multicyclic ring system, each multicyclic ring system substituted with $R^9$ and optionally substituted with one or more $R^{10}$;

each Q is independently selected from the group —CHR$^{13}$—, —NR$^{13}$—, —O—, and —S(O)$_p$—;

$R^8$ is H; 1–2 halogen; $C_1$–$C_6$ alkyl; $C_1$–$C_6$ haloalkyl; $C_1$–$C_6$ alkoxy; $C_1$–$C_6$ haloalkoxy; $C_2$–$C_6$ alkenyl; $C_2$–$C_6$ haloalkenyl; $C_2$–$C_6$ alkynyl; $C_1$–$C_6$ alkylthio; $C_1$–$C_6$ haloalkylthio; $C_1$–$C_6$ alkylsulfinyl; $C_1$–$C_6$ alkylsulfonyl; $C_3$–$C_6$ cycloalkyl; $C_3$–$C_6$ alkenyloxy; $CO_2$ ($C_1$–$C_6$ alkyl); NH($C_1$–$C_6$ alkyl); N($C_1$–$C_6$ alkyl)$_2$; cyano; nitro; SiR$^{19}$R$^{20}$R$^{21}$; or GeR$^{19}$R$^{20}$R$^{21}$;

$R^9$ is H; 1–2 halogen; $C_1$–$C_6$ alkyl; $C_1$–$C_6$ haloalkyl; $C_1$–$C_6$ alkoxy; $C_1$–$C_6$ haloalkoxy; $C_2$–$C_6$ alkenyl; $C_2$–$C_6$ haloalkenyl; $C_2$–$C_6$ alkynyl; $C_1$–$C_6$ alkylthio; $C_1$–$C_6$ haloalkylthio; $C_1$–$C_6$ alkylsulfinyl; $C_1$–$C_6$ alkylsulfonyl; $C_3$–$C_6$ cycloalkyl; $C_3$–$C_6$ alkenyloxy; $CO_2$ ($C_1$–$C_6$ alkyl); NH($C_1$–$C_6$ alkyl); N($C_1$–$C_6$ alkyl)$_2$; —C(R$^{18}$)=NOR$^{17}$; cyano; nitro; SF$_5$; SiR$^{22}$R$^{23}$R$^{24}$; or GeR$^{22}$R$^{23}$R$^{24}$; or $R^9$ is phenyl, benzyl, benzoyl, phenoxy, pyridinyl, pyridinyloxy, thienyl, thienyloxy, furanyl, pyrimidinyl, or pyrimidinyloxy each optionally substituted with one of $R^{11}$, $R^{12}$, or both $R^{11}$ and $R^{12}$;

each $R^{10}$ is independently halogen; $C_1$–$C_4$ alkyl; $C_1$–$C_4$ haloalkyl; $C_1$–$C_4$ alkoxy; nitro; or cyano; or when $R^9$ and an $R^{10}$ are attached to adjacent atoms on Z, $R^9$ and said adjacently attached $R^{10}$ can be taken together as —OCH$_2$O— or —OCH$_2$CH$_2$O—; each CH$_2$ group of said taken together $R^9$ and $R^{10}$ optionally substituted with 1–2 halogen; or when Y and an $R^{10}$ are attached to adjacent atoms on Z and Y is —CHR$^6$O—N=C(R$^7$)— or —O—N=C(R$^7$)—, $R^7$ and said adjacently attached $R^{10}$ can be taken together as —(CH$_2$)$_r$—J— such that J is attached to Z;

J is —CH$_2$—; —CH$_2$CH$_2$—; —OCH$_2$—; —CH$_2$O—; —SCH$_2$—; —CH$_2$S—; —N(R$^{16}$)CH$_2$—; or —CH$_2$N(R$^{16}$)—; each CH$_2$ group of said J optionally substituted with 1 to 2 CH$_3$;

$R^{11}$ and $R^{12}$ are each independently halogen; $C_1$–$C_4$ alkyl; $C_1$–$C_4$ haloalkyl; $C_1$–$C_4$ alkoxy; $C_1$–$C_4$ haloalkoxy; nitro; cyano; Si(R$^{25}$)$_3$; or Ge(R$^{25}$)$_3$;

each $R^{13}$ is independently H; $C_1$–$C_6$ alkyl; $C_1$–$C_6$ haloalkyl; or phenyl optionally substituted with halogen, $C_1$–$C_4$ alkyl, $C_1$–$C_4$ haloalkyl, $C_1$–$C_4$ alkoxy, $C_1$–$C_4$ haloalkoxy, nitro or cyano;

$R^{15}$, $R^{16}$, $R^{17}$, and $R^{18}$ are each independently H; $C_1$–$C_3$ alkyl; or phenyl optionally substituted with halogen, $C_1$–$C_4$ alkyl, $C_1$–$C_4$ haloalkyl, $C_1$–$C_4$ alkoxy, $C_1$–$C_4$ haloalkoxy, nitro or cyano;

$R^{19}$, $R^{20}$, $R^{21}$, $R^{22}$, $R^{23}$, and $R^{24}$ are each independently $C_1$–$C_6$ alkyl; $C_2$–$C_6$ alkenyl; $C_1$–$C_4$ alkoxy; or phenyl;

each $R^{25}$ is independently $C_1$–$C_4$ alkyl;

m, n and p are each independently 0, 1 or 2; and r is 0 or 1.

2. A compound of claim 1 wherein

W is O;

$R^1$ is $C_1$–$C_3$ alkyl or $C_1$–$C_3$ haloalkyl;

$R^2$ is H; $C_1$–$C_6$ alkyl; $C_1$–$C_6$ haloalkyl; or $C_3$–$C_6$ cycloalkyl;

$R^3$ and $R^4$ are each independently H; halogen; cyano; nitro; $C_1$–$C_6$ alkyl; $C_1$–$C_6$ haloalkyl; $C_1$–$C_6$ alkoxy; $C_1$–$C_6$ haloalkoxy; or $C_1$–$C_6$ alkylthio;

Y is —O—; —CH=CH—; —C≡C—; —CH$_2$O—; —OCH$_2$—; —CH$_2$S(O)$_n$—; —CH$_2$O—N=C(R$^7$)—; —C(R$^7$)=N—O—; —CH$_2$OC(O)NH—; or a direct bond;

$R^7$ is H; $C_1$–$C_6$ alkyl; $C_1$–$C_6$ haloalkyl; $C_1$–$C_6$ alkoxy; $C_2$–$C_6$ alkenyl; $C_2$–$C_6$ alkynyl; $C_3$–$C_6$ cycloalkyl; halogen; or cyano; or when Y and an $R^{10}$ are attached to adjacent atoms on Z and Y is —CH$_2$O—N=C(R$^7$)—, $R^7$ and said adjacently attached $R^{10}$ can be taken together as —(CH$_2$)$_r$—J— such that J is attached to Z; and $R^9$ is H; 1–2 halogen; $C_1$–$C_6$ alkyl; $C_1$–$C_6$ haloalkyl; $C_1$–$C_6$ alkoxy; $C_1$–$C_6$ haloalkoxy; $C_1$–$C_6$ alkylthio; cyano; CO$_2$($C_1$–$C_6$ alkyl); NH($C_1$–$C_6$ alkyl); N($C_1$–$C_6$ alkyl)$_2$; SiR$^{22}$R$^{23}$R$^{24}$; or GeR$^{22}$R$^{23}$R$^{24}$; or $R^9$ is $C_3$–$C_6$ cycloalkyl, phenyl, phenoxy, pyridinyl, pyridinyloxy, pyrimidinyl, or pyrimidinyloxy, each optionally substituted with one of $R^{11}$, $R^{12}$, or both $R^{11}$ and $R^{12}$.

3. A compound of claim 2 wherein

Z is selected from the group Z-1 to Z-10, Z-19, Z-22, Z-24 and Z-57, each multicyclic ring system substituted with $R^9$ and optionally substituted with one or more $R^{10}$;

$R^7$ is H; $C_1$–$C_6$ alkyl; $C_1$–$C_6$ haloalkyl; $C_1$–$C_6$ alkoxy; $C_2$–$C_6$ alkenyl; $C_2$–$C_6$ alkynyl; cyclopropyl; or cyano; or when Y and an $R^{10}$ are attached to adjacent atoms on Z and Y is —CH$_2$O—N=C($R^7$)—, $R^7$ and said adjacently attached $R^{10}$ can be taken together as —(CH$_2$)$_r$—J— such that J is attached to Z;

J is —CH$_2$— or —CH$_2$CH$_2$—; and r is 1.

4. A compound of claim 3 wherein

X is OR$^1$;

$R^1$ is $C_1$–$C_3$ alkyl;

$R^2$ is H or $C_1$–$C_2$ alkyl;

$R^3$ and $R^4$ are independently H; halogen; cyano; methyl; trifluoromethyl; methoxy; trifluoromethoxy; or methylthio;

Y is —O—; —CH=CH—; —CH$_2$O—; —CH$_2$O—N=C($R^7$)—; or —CH$_2$OC(=O)NH—;

$R^7$ is H; $C_1$–$C_3$ alkyl; $C_1$–$C_3$ haloalkyl; $C_1$–$C_3$ alkoxy; or cyclopropyl; and Z is selected from the group Z-1, Z-5, Z-19, Z-22, Z-24, and Z-57, each multicyclic ring system substituted with $R^9$ and optionally substituted with one or more $R^{10}$.

5. A compound of claim 4 wherein

Y is —O—; —CH$_2$O—; or —CH$_2$O—N=C($R^7$)—; and $R^7$ is H; $C_1$–$C_2$ alkyl; $C_1$–$C_2$ haloalkyl; methoxy; or cyclopropyl.

6. A compound of claim 5 wherein $R^1$ is methyl; and $R^2$ is methyl.

7. A fungicidal composition comprising a fingicidally effective amount of a compound of claim 1 and at least one of a surfactant, a solid diluent or a liquid diluent.

8. A method for controlling plant diseases caused by fungal plant pathogens comprising applying to the plant or a portion thereof, or to the plant seed or seedling, a fingicidally effective amount of a compound of claim 1.

9. A compound selected from Formula I, N-oxides and agriculturally-suitable salts thereof,

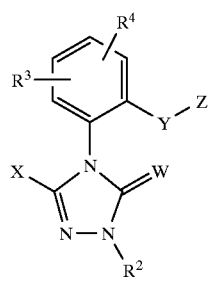

I wherein:

W is O or S;

X is OR$^1$; S(O)$_m$R$^1$; or halogen;

$R^1$ is H; $C_1$–$C_6$ alkyl; $C_1$–$C_6$ haloalkyl; $C_2$–$C_6$ alkenyl; $C_2$–$C_6$ haloalkenyl; $C_2$–$C_6$ alkynyl; $C_2$–$C_6$ haloalkynyl; $C_3$–$C_6$ cycloalkyl; $C_2$–$C_4$ alkylcarbonyl; or $C_2$–$C_4$ alkoxycarbonyl;

$R^2$ is H; $C_1$–$C_6$ alkyl; $C_1$–$C_6$ haloalkyl; $C_2$–$C_6$ alkenyl; $C_2$–$C_6$ haloalkenyl; $C_2$–$C_6$ alkynyl; $C_2$–$C_6$ haloalkynyl; $C_3$–$C_6$ cycloalkyl; $C_2$–$C_4$ alkylcarbonyl; or $C_2$–$C_4$ alkoxycarbonyl;

$R^3$ and $R^4$ are each independently H; halogen; cyano; nitro; hydroxy; $C_1$–$C_6$ alkyl; $C_1$–$C_6$ haloalkyl; $C_2$–$C_6$ alkenyl; $C_2$–$C_6$ haloalkenyl; $C_2$–$C_6$ alkynyl; $C_2$–$C_6$ haloalkynyl; $C_1$–$C_6$ alkoxy; $C_1$–$C_6$ haloalkoxy; $C_2$–$C_6$ alkenyloxy; $C_2$–$C_6$ alkynyloxy; or phenyl substituted with $R^8$ and optionally substituted with one or more $R^{10}$;

Y is —O—; —S(O)$_n$—; —NR$^6$—; —C(=O)—; —CH(OR$^6$)—; —CHR$^6$—; —CHR$^6$CHR$^6$—; —CR$^6$=CR$^6$—; —C≡C—; —CHR$^6$O—; —OCHR$^6$—; —CHR$^6$S(O)$_n$—; —S(O)$_n$CHR$^6$—; —CHR$^6$O—N=C(R$^7$)—; —(R$^7$)C=N—OCH(R$^6$)—; —C(R$^7$)=N—O—; —O—N=C(R$^7$)—; —CHR$^6$OC(=O)N(R$^{15}$)—; or a direct bond; and the directionality of the Y linkage is defined such that the moiety depicted on the left side of the linkage is bonded to the phenyl ring and the moiety on the right side of the linkage is bonded to Z;

each $R^6$ is independently H or $C_1$–$C_3$ alkyl;

$R^7$ is H; $C_1$–$C_6$ alkyl; $C_1$–$C_6$ haloalkyl; $C_1$–$C_6$ alkoxy; $C_1$–$C_6$ haloalkoxy; $C_1$–$C_6$ alkylthio; $C_1$–$C_6$ alkylsulfinyl; $C_1$–$C_6$ alkylsulfonyl; $C_1$–$C_6$ haloalkylthio; $C_1$–$C_6$ haloalkylsulfinyl; $C_1$–$C_6$ haloalkylsulfonyl; $C_2$–$C_6$ alkenyl; $C_2$–$C_6$ haloalkenyl; $C_2$–$C_6$ alkynyl; $C_2$–$C_6$ haloalkynyl; $C_3$–$C_6$ cycloalkyl; $C_2$–$C_4$ alkylcarbonyl; $C_2$–$C_4$ alkoxycarbonyl; halogen; cyano; or morpholinyl;

Z is a ring system selected from:

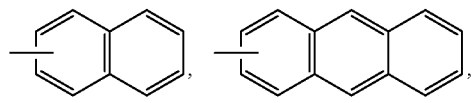

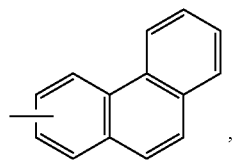 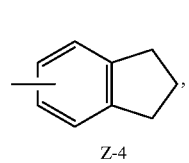

Z-3, Z-4

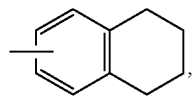 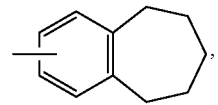

Z-5, Z-6

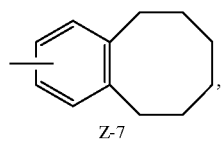 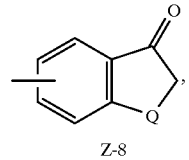

Z-7, Z-8

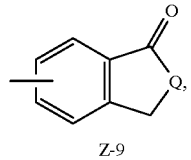 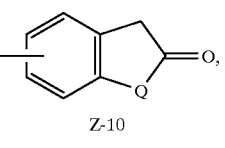

Z-9, Z-10

-continued

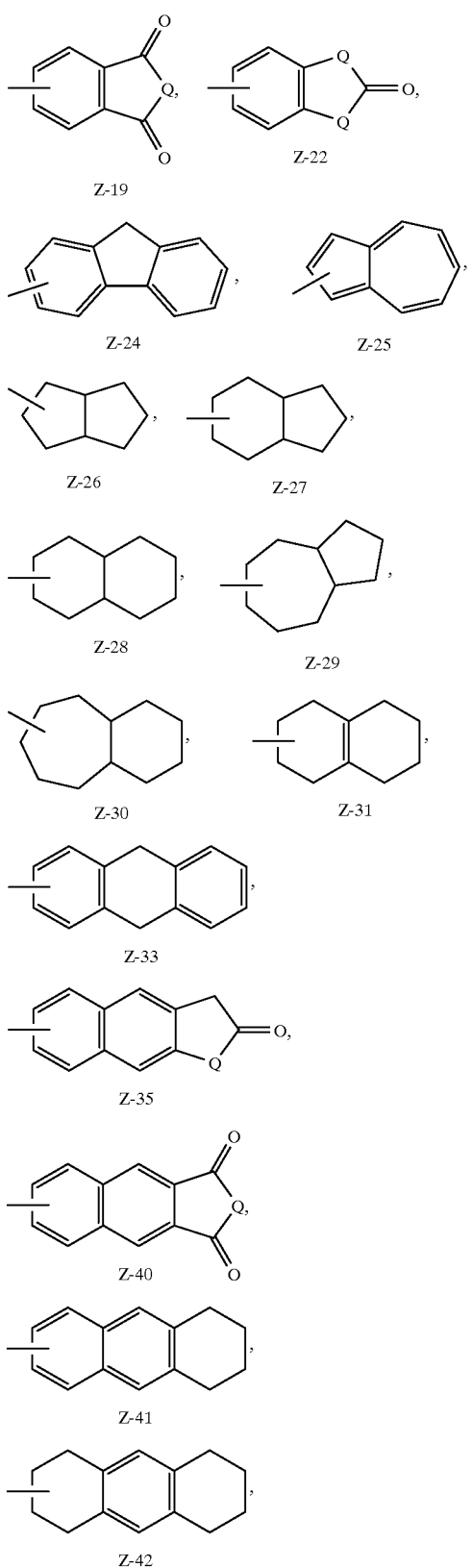

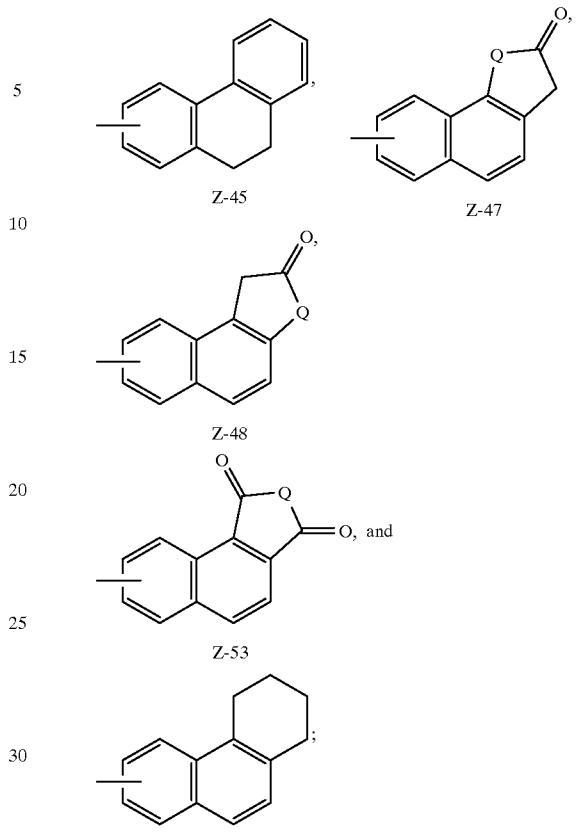

where the point of attachment with Y is selected from any available position on the entire multicyclic ring system, each multicyclic ring system substituted with $R^9$ and optionally substituted with one or more $R^{10}$;

each Q is independently selected from the group —$CHR^{13}$—, —$NR^{13}$—, —O—, and —$S(O)_p$—;

$R^8$ is H; 1–2 halogen; $C_1$–$C_6$ alkyl; $C_1$–$C_6$ haloalkyl; $C_1$–$C_6$ alkoxy; $C_1$–$C_6$ haloalkoxy; $C_2$–$C_6$ alkenyl; $C_2$–$C_6$ haloalkenyl; $C_2$–$C_6$ alkynyl; $C_1$–$C_6$ alkylthio; $C_1$–$C_6$ haloalkylthio; $C_1$–$C_6$ alkylsulfinyl; $C_1$–$C_6$ alkylsulfonyl; $C_3$–$C_6$ cycloalkyl; $C_3$–$C_6$ alkenyloxy; $CO_2$ ($C_1$–$C_6$ alkyl); NH($C_1$–$C_6$ alkyl); N($C_1$–$C_6$ alkyl)$_2$; cyano; nitro; $SiR^{19}R^{20}R^{21}$; or $GeR^{19}R^{20}R^{21}$;

$R^9$ is H; 1–2 halogen; $C_1$–$C_6$ alkyl; $C_1$–$C_6$ haloalkyl; $C_1$–$C_6$ alkoxy; $C_1$–$C_6$ haloalkoxy; $C_2$–$C_6$ alkenyl; $C_2$–$C_6$ haloalkenyl; $C_2$–$C_6$ alkynyl; $C_1$–$C_6$ alkylthio; $C_1$–$C_6$ haloalkylthio; $C_1$–$C_6$ alkylsulfinyl; $C_1$–$C_6$ alkylsulfonyl; $C_3$–$C_6$ cycloalkyl; $C_3$–$C_6$ alkenyloxy; $CO_2$ ($C_1$–$C_6$ alkyl); NH($C_1$–$C_6$ alkyl); N($C_1$–$C_6$ alkyl)$_2$; —C($R^{18}$)=$NOR^{17}$; cyano; nitro; $SiR^{22}R^{23}R^{24}$; or $GeR^{22}R^{23}R^{24}$; or $R^9$ is phenyl, benzyl, benzoyl, phenoxy, pyridinyl, pyridinyloxy, thienyl, thienyloxy, furanyl, pyrimidinyl, or pyrimidinyloxy each optionally substituted with one of $R^{11}$, $R^{12}$, or both $R^{11}$ and $R^{12}$;

each $R^{10}$ is independently halogen; $C_1$–$C_4$ alkyl; $C_1$–$C_4$ haloalkyl; $C_1$–$C_4$ alkoxy; nitro; or cyano; or when $R^9$ and an $R^{10}$ are attached to adjacent atoms on Z, $R^9$ and said adjacently attached $R^{10}$ can be taken together as —OCH$_2$O— or —OCH$_2$CH$_2$O—; each CH$_2$ group of said taken together R$^9$ and R$^{10}$ optionally substituted with 1–2 halogen; or when Y and an R$^{10}$ are attached to adjacent atoms on Z and Y is —CHR$^6$O—N=C(R$^7$)— or —O—N=C(R$^7$)—, R$^7$ and said adjacently attached R$^{10}$ can be taken together as —(CH$_2$)$_r$—J— such that J is attached to Z;

J is —CH$_2$—; —CH$_2$CH$_2$—; —OCH$_2$—; —CH$_2$O—; —SCH$_2$—; —CH$_2$S—; —N(R$^{16}$)CH$_2$—; or —CH$_2$N(R$^{16}$)—; each CH$_2$ group of said J optionally substituted with 1 to 2 CH$_3$;

R$^{11}$ and R$^{12}$ are each independently halogen; C$_1$–C$_4$ alkyl; C$_1$–C$_4$ haloalkyl; C$_1$–C$_4$ alkoxy; C$_1$–C$_4$ haloalkoxy; nitro; cyano; Si(R$^{25}$)$_3$; or Ge($^{25}$)$_3$;

each R$^{13}$ is independently H; C$_1$–C$_6$ alkyl; C$_1$–C$_6$ haloalkyl; or phenyl optionally substituted with halogen, C$_1$–C$_4$ alkyl, C$_1$–C$_4$ haloalkyl, C$_1$–C$_4$ alkoxy, C$_1$–C$_4$ haloalkoxy, nitro or cyano;

R$^{15}$, R$^{16}$, R$^{17}$, and R$^{18}$ are each independently H; C$_1$–C$_3$ alkyl; or phenyl optionally substituted with halogen, C$_1$–C$_4$ alkyl, C$_1$–C$_4$ haloalkyl, C$_1$–C$_4$ alkoxy, C$_1$–C$_4$ haloalkoxy, nitro or cyano;

R$^{19}$, R$^{20}$, R$^{21}$, R$^{22}$, R$^{23}$, and R$^{24}$ are each independently C$_1$–C$_6$ alkyl; C$_1$–C$_4$ alkoxy; or phenyl;

each R$^{25}$ is independently C$_1$–C$_4$ alkyl;

m, n and p are each independently 0, 1 or 2; and r is 0 or 1.

10. The compound of claim 6 which is selected from the group:

2,4-dihydro-5-methoxy-2-methyl-4-[2-[[[[1-(2-naphthalenyl)ethylidene]amino]oxy]methyl]phenyl]-3H-1,2,4-triazol-3-one;

2,4-dihydro-5-methoxy-2-methyl-4-[2-[[[[1-(5,6,7,8-tetrahydro-2-naphthalenyl)ethylidene]amino]oxy]methyl]phenyl]-3H-1,2,4-triazol-3-one; and 2,4-dihydro-5-methoxy-2-methyl4-[2-methyl-6-[[[[1-(2-naphthalenyl)ethylidene]amino]oxy]methyl]phenyl]-3H-1,2,4-triazol-3-one.

* * * * *